United States Patent
Marasco et al.

(10) Patent No.: US 8,329,178 B2
(45) Date of Patent: Dec. 11, 2012

(54) ANTIBODIES AGAINST CXCR4 AND METHODS OF USE THEREOF

(75) Inventors: Wayne A. Marasco, Wellesley, MA (US); Jianhua Sui, Boston, MA (US); Chen Xu, Beijing (CN)

(73) Assignee: Dana-Farber Cancer Institute, Inc., Boston, MA (US)

( * ) Notice: Subject to any disclaimer, the term of this patent is extended or adjusted under 35 U.S.C. 154(b) by 1107 days.

(21) Appl. No.: 11/883,258

(22) PCT Filed: Feb. 15, 2006

(86) PCT No.: PCT/US2006/005691
§ 371 (c)(1),
(2), (4) Date: Aug. 29, 2008

(87) PCT Pub. No.: WO2006/089141
PCT Pub. Date: Aug. 24, 2006

(65) Prior Publication Data
US 2011/0250165 A1 Oct. 13, 2011

Related U.S. Application Data

(60) Provisional application No. 60/654,377, filed on Feb. 18, 2005.

(51) Int. Cl.
*A61K 39/395* (2006.01)
*C07K 16/28* (2006.01)
*C07K 14/47* (2006.01)
*C07K 16/46* (2006.01)
*C07K 14/715* (2006.01)

(52) U.S. Cl. .............. 424/143.1; 424/133.1; 424/135.1; 530/350; 530/387.3; 530/388.22; 530/324; 530/402

(58) Field of Classification Search .................. None
See application file for complete search history.

(56) References Cited

U.S. PATENT DOCUMENTS
3,773,919 A 11/1973 Boswell et al.
(Continued)

FOREIGN PATENT DOCUMENTS
EP 1 449 850 8/2004
(Continued)

OTHER PUBLICATIONS

Baribaud et al., Antigenically distinct conformations of CXCR4, J. Virol. 75(19):8957-8967, Oct. 2001.*

(Continued)

*Primary Examiner* — Claire Kaufman
(74) *Attorney, Agent, or Firm* — Mintz Levin Cohn Ferris Glovsky and Popeo, P.C.; Ivor R. Elrifi; Cynthia A. Kozakiewicz

(57) ABSTRACT

The invention provides human monoclonal antibodies or fragments thereof, that specifically bind to CXCR4. Disclosed are methods of use of such antibodies for the treatment and/or prevention of a CXCR4 disease or disorder such as cancer and X4-tropic HIV-1 infection Also provided are methods of use of such antibodies and antibody fragments for the treatment or prevention of cancer metastasis. The invention provides methods of mobilizing CD34+ stem cells from the bone marrow and methods of blocking chemotaxis of CXCR4-expressing cells in response to SDF-1. Also provided are methods of use of the antibodies and fragments thereof for the prevention or treatment of graft-versus-host disease. Finally, the invention provides methods of inhibiting new tumor blood vessel formation and/or tumor cell angiogenesis.

8 Claims, 28 Drawing Sheets

U.S. PATENT DOCUMENTS

| | | | |
|---|---|---|---|
| 4,485,045 | A | 11/1984 | Regen |
| 4,522,811 | A | 6/1985 | Eppstein et al. |
| 4,544,545 | A | 10/1985 | Ryan et al. |
| 4,676,980 | A | 6/1987 | Segal et al. |
| 4,816,567 | A | 3/1989 | Cabilly et al. |
| 4,946,778 | A | 8/1990 | Ladner et al. |
| 5,013,556 | A | 5/1991 | Woodle et al. |
| 5,030,719 | A | 7/1991 | Umemoto et al. |
| 5,091,513 | A | 2/1992 | Huston et al. |
| 5,132,405 | A | 7/1992 | Huston et al. |
| 5,233,409 | A | 8/1993 | Schwab |
| 5,545,806 | A | 8/1996 | Lonberg et al. |
| 5,545,807 | A | 8/1996 | Surani et al. |
| 5,569,825 | A | 10/1996 | Lonberg et al. |
| 5,625,126 | A | 4/1997 | Lonberg et al. |
| 5,633,425 | A | 5/1997 | Lonberg et al. |
| 5,661,016 | A | 8/1997 | Lonberg et al. |
| 5,916,771 | A | 6/1999 | Hori et al. |
| 5,939,598 | A | 8/1999 | Kucherlapati et al. |
| 6,761,902 | B2 | 7/2004 | Sodroski et al. |
| 7,138,496 | B2 * | 11/2006 | Hua et al. .................. 530/387.1 |

FOREIGN PATENT DOCUMENTS

| | | |
|---|---|---|
| WO | WO 91/00360 | 1/1991 |
| WO | WO 92/20373 | 11/1992 |
| WO | WO 93/08829 | 5/1993 |
| WO | WO 94/02602 | 2/1994 |
| WO | WO 94/11026 | 5/1994 |
| WO | WO 95/22618 | 8/1995 |
| WO | WO 96/27011 | 9/1996 |
| WO | WO 96/33735 | 10/1996 |
| WO | WO 96/34096 | 10/1996 |
| WO | WO 99/53049 | 10/1999 |
| WO | WO 00/42074 A1 | 7/2000 |
| WO | WO 01/423082 A2 | 6/2001 |
| WO | WO 03/066830 A2 | 8/2003 |
| WO | WO 2004/059285 A2 | 7/2004 |
| WO | WO 2006/089141 A3 | 8/2006 |

OTHER PUBLICATIONS

MacCallum et al.,Antibody-antigen interactions: contact analysis and binding site topography, J. Mol. Biol. 262:732-745, 1996.*
Lamminmaki et al., Chrystal structure of a recombinant anti-estradiol Fab fragment in complex with the 17beta-estradiol, J. Blol. Chem. 276:36687-94, 2001.*
Rudikoff et al., Single amino acid substitution altering antigen-binding specificity, Proc. Nat. Acad. Sci. USA, 79:1979-1983, Mar. 1982.*
Carnec et al., Anti-CXCR4 monoclonal antibodies recognizing overlapping epitopes differ significantly in their ability to inhibit entry ot human immunodeficiency virus type 1, J. Virol. 79(3):1930-1933, Feb. 2005.*
Bleul et al., The HIV coreceptors CXCR4 and CCR5 are differentially expressed and regulated on human T lymphocytes, Proc. Nat. Acad. Sci. USA, 94:1925-1930, Mar. 1997.*
S.A. Karim, Salim Abdool Karim's game changers in HIV prevention 2011: Broadly neutralizing antibodies and HIV vaccines, Medscape HIV/AIDS [online] [retrieved Dec. 14, 2011]. Retrieved from: WebMD 2011.*
BouHamdan et al., Inhibition of HIV-1 infection by down-regulation of the CXCR4 co-receptor using an intracellular single chain variable fragment against CXCR4, Gene Therapy, 8:408-418, 2001.*
Skerlj et al., Design of novel CXCR4 antagonists that are potent inhibitors of T-tropic (X4) HIV-1 replication, Bioorganic Med. Chem. Lett. 21:1414-1418, 2011.*
Moyle et al., Proof of activity with AMD11070, an orally bioavailable inhibitor of CXCR4-tropic HIV type 1, Clin. Infect. Diseases, 48:798-805, 2009.*
Alkahatib et al., "CC CKR5: A Rantes, MIP-1α, MIP-1β Receptor as a Fusion Cofactor for Macrophage-Tropic HIV-1", *Science*, 272:1955-1958 (1996).
Argiris et al., "Synergistic Interactions Between Tamoxifen and Herceptin™", *Proc. Am. Assoc. Cancer Res.*, 41:718, #4565 (2000) (Abstract Only).
Bachelder et al., "Vascular Endothelial Growth Factor Promotes Breast Carcinoma Invasion in an Autocrine Manner by Regulating the Chemokine Receptor CXCR4", *Cancer Res.*, 62:7203-7206 (2002).
Baggiolini et al., "Human Chemokines: An Update", *Ann. Rev. Immunol.*, 15:675-705 (1997).
Barbas et al., "Recombinant human Fab fragments neutralize human type 1 immunodeficiency virus in vitro", *Proc. Nat'l. Acad. Sci. U.S.A.*, 89:9339-9343 (1992).
Baselga et al., "Recombinant Humanized Anti-HER2 Antibody (Herceptin™) Enhances the Antitumor Activity of Paclitaxel and Doxorubicin Against HER2/*neu* Overexpressing Human Breast Cancer Xenografts", *Cancer Res.*, 58:2825-2831 (1998).
Benovic et al., "A new key in breast cancer metastasis", *Cancer Cell*, 6:429-430 (2004).
Bernards, R., "Cues for migration", *Nature*, 425:247-248 (2003).
Berson et al., "A Seven-Transmembrane Domain Receptor Involved in Fusion and Entry of T-Cell-Tropic Human Immunodeficiency Virus Type 1 Strains", *J. Virol.*, 70(9):6288-6295 (1996).
Bleul et al., "The lymphocyte chemoattractant SDF-1 is a ligand for LESTR/fusin and blocks HIV-1 entry", *Nature*, 382:829-833 (1996).
Bobo et al., "Convection-enhanced delivery of macromolecules in the brain," *Proc. Nat'l. Acad. Sci. U.S.A.*, 91:2076-2080 (1994).
Brelot et al., "Role of the First and Third Extracellular Domains of CXCR-4 in Human Immunodeficiency Virus Coreceptor Activity", *J. Virol.*, 71(6):4744-4751 (1997).
Brennan et al., "Preparation of Bispecific Antibodies by Chemical Recombination of Monoclonal Immunoglobulin $G_1$ Fragments", *Science*, 229:81-83 (1985).
Broder et al., "Chemokine receptors and HIV", *J. Leukocyte Biol.*, 62:20-29 (1997).
Carell et al., "A Novel Procedure for the Synthesis of Libraries Containing Small Organic Molecules", *Angew. Chem. Int. Ed. Engl.*, 33(20):2059-2061 (1994).
Carell et al., "A Solution-Phase Screening Procedure for the Isolation of Active Compounds from a Library of Molecules", *Angew. Chem. Int. Ed. Engl.*, 33(20):2061-2064 (1994).
Carmeliet et al., "Angiogenesis in cancer and other diseases", *Nature*, 407:249-257 (2000).
Caron et al., "Engineered Humanized Dimeric Forms of IgG Are More Effective Antibodies", *J. Exp. Med.*, 176:1191-1195 (1992).
Ceradini et al., "Progenitor cell trafficking is regulated by hypoxic gradients through HIF-1 induction of SDF-1", *Nature Med.*, 10(8):858-864 (2004).
Cho et al., "An Unnatural Biopolymer", *Science*, 261:1303-1305 (1993).
Connor et al., "Change in Coreceptor Use Correlates with Disease Progression in HIV-1-Infected Individuals", *J. Exp. Med.*, 185:621-628 (1997.
Cote et al., "Generation of human monoclonal antibodies reactive with cellular antigens", *Proc. Nat'l. Acad. Sci. U.S.A.*, 80:2026-2030 (1983).
Cull et al., "Screening for receptor ligands using large libraries of peptides linked to the C terminus of the *lac* repressor", *Proc. Nat'l. Acad. Sci. U.S.A.*, 89:1865-1869 (1992).
Cwirla et al., "Peptides on phage: A vast library of peptides for identifying ligands", *Proc. Nat'l. Acad. Sci. U.S.A.*, 87:6378-6382 (1990).
Davidson et al., "A model system for in vivo gene transfer into the central nervous system using an adenoviral vector", *Nat. Genet.*, 3(3):219-223 (1993).
Davies et al., "Antibody-Antigen Complexes", *Ann. Rev. Biochem.*, 59:439-473 (1990).
Deng et al., "Identification of a major co-receptor for primary isolates of HIV-1", *Nature*, 381:661-666 (1996).
Devlin et al., "Random Peptide Libraries: A Source of Specific Protein Binding Molecules", *Science*, 249:404-406 (1990).
DeWitt et al., "'Diversomers': An approach to nonpeptide, nonoligomeric chemical diversity", *Proc. Nat'l. Acad. Sci. U.S.A.*, 90:6909-6913 (1993).
Doranz et al., "A Dual-Tropic Primary HIV-1 Isolate That Uses Fusin and the β-Chemokine Receptors CKR-5, CKR-3, and CKR-2b as Fusion Cofactors", *Cell*, 85:1149-1158 (1996).

Endres et al., "CD4-Independent Infection by HIV-2 Is Mediated by Fusin/CXCR4", *Cell*, 87:745-756 (1996).

Eppstein et al., "Biological activity of liposome-encapsulated murine interferon γ is mediated by a cell membrane receptor", *Proc. Nat'l. Acad. Sci. U.S.A.*, 82:3688-3692 (1985).

Erb et al., "Recursive deconvolution of combinatorial chemical libraries", *Proc. Nat'l. Acad. Sci, U.S.A.*, 91:11422-11426 (1994).

Felici et al., "Selection of Antibody Ligands from a Large Library of Oligopeptides Expressed on a Multivalent Exposition Vector", *J. Mol. Biol.*, 222(2):301-310 (1991).

Feng et al., "HIV-1 Entry Cofactor: Functional cDNA Cloning of a Seven-Transmembrane, G Protein-Coupled Receptor", *Science*, 272:872-877 (1996).

Fishwild et al., "High-avidity human $IgG_K$ monoclonal antibodies from a novel starin of minilocus transgenic mice", *Nature Biotech.*, 14(7):845-851 (1996).

Fodor et al., "Multiplexed biochemical assays with biological chips", *Nature*, 364:555-556 (1993).

Folkman et al., "Blood Vessel Formation: What Is Its Molecular Basis?", *Cell*, 87:1153-1155 (1996).

Gallop et al., "Applications of Combinatorial Technologies to Drug Discovery. 1. Background and Peptide Combinatorial Libraries", *J. Med. Chem.*, 37(9):1233-1251 (1994).

Geller et al., "An HSV-1 Vector Expressing Tyrosine Hydroxylase Causes Production and Release of L-DOPA from Cultured Rat Striatal Cells", *J. Neurochem.*, 64:487-496 (1995).

Geller et al., "Infection of cultured central nervous system neurons with a defective herpes simplex virus 1 vector results in stable expression of *Escherichia coil* β-galactosidase", *Proc. Nat'l. Acad. Sci. U.S.A.*, 87:1149-1153 (1990).

Geller et al., "Long-term increases in neurotransmitter release from neuronal cells expressing a constitutively active adenylate cyclase from a herpes simplex virus type 1 vector", *Proc. Nat'l. Acad. Sci. U.S.A.*, 90:7603-7607 (1993).

Gruber et al., "Efficient Tumor Cell Lysis Mediated by a Bispecific Single Chain Antibody Expressed in *Escherichia coli*", *J. Immunol.*, 152:5368-5374 (1994).

Hanahan et al., "Patterns and Emerging Mechanisms of the Angiogenic Switch during Tumorigenesis", *Cell*, 86:353-364 (1996).

Hernandez et al., "Mutations in the chemokine receptor gene CXCR4 are associated with WHIM syndrome, a combined immunodeficiency disease", *Nat. Genet.*, 34:70-74 (2003).

Hollinger et al., "'Diabodies': Small bivalent and bispecific antibody fragments", *Proc. Nat'l. Acad. Sci. U.S.A.*, 90:6444-6448(1993).

Hoogenboom et al., "By-passing Immunisation. Human Antibodies from Synthetic Repertoires of Germline $V_H$ Gene Segments Rearranged in Vitro", *J. Mol. Biol.*, 227:381-388 (1992).

Houghten et al., "The Use of Synthetic Peptide Combinatorial Libraries for the Identification of Bioactive Peptides", *Biotech.*, 13(3):412-421 (1992).

Huse et al., "Generation of a Large Combinatorial Library of the Immunoglobulin Repertoire in Phage Lambda", *Science*, 246:1275-1281 (1989).

Huston et al., "Protein engineering of antibody binding sites: Recovery of specific activity in an anti-digoxin single-chain Fv analogue produced in *Escherichia coli*", *Proc. Nat'l. Acad. Sci. U.S.A.*, 85(16):5879-5883 (1988).

Hwang et al., "Hepatic uptake and degradation of unilamellar sphingomyelin/cholesterol liposomes: A kinetic study", *Proc. Nat'l. Acad. Sci. U.S.A.*, 77(7):4030-4034 (1980).

Imitola et al., "Directed migration of neural stem cells to sites of CNS injury by the stromal cell-derived factor 1α/CXC chemokine receptor 4 pathway", *Proc. Nat'l. Acad. Sci. U.S.A.*, 101(52):18117-18122 (2004).

Jansen et al., "Immunotoxins: Hybrid Molecules Combining High Specificity and Potent Cytotoxicity", *Immunol. Rev.*, 62:185-216 (1982).

Kaplitt et al., "Long-term gene expression and phenotypic correction using adeno-associated virus vectors in the mammalian brain", *Nat. Genet.*, 8:148-154 (1994).

Killen et al., "Specific Killing of Lymphocytes That Cause Experimental Autoimmune Myasthenia Gravis by Ricin Toxin-Acetylcholine Receptor Conjugates" *J. Immunol.*, 133(5):2549-2553 (1984).

Knaut et al., "A zebrafish homologue of the chemokine receptor Cxcr4 is a germ-cell guidance receptor", *Nature*, 421:279-282 (2003).

Kohler et al., "Continuous cultures of fused cells secreting antibody of predefined specificity", *Nature*, 256:495-497 (1975).

Kostelny et al., "Formation of a Bispecific Antibody by the Use of Leucine Zippers", *J. Immunol.*, 148(5):1547-1553 (1992).

Kozbor et al., "A Human Hybrid Myeloma for Production of Human Monoclonal Antibodies", *J. Immunol.*, 133(6):3001-3005 (1984).

Kozbor et al., "The production of monoclonal antibodies from human lymphocytes", *Immunol. Today*, 4(3):72-(1983).

Kryczek et al., "CXCL12 and Vascular Endothelial Growth Factor Synergistically Induce Neoangiogenesis in Human Ovarian Cancers", *Cancer Res.*, 65(2):465-472 (2005).

Kunwar et al., "Germ-cell attraction", *Nature*, 421:226-227 (2003).

Lam et al., "A new type of synthetic peptide library for identifying ligand-binding activity", *Nature*, 354:82-84 (1991).

Lam, K.S., "Application of combinatorial library methods in cancer research and drug discovery", *Anti-Cancer Drug Des.*, 12(3):145-167 (1997).

Lapteva et al., "CXCR4 knockdown by small interfering RNA abrogates breast tumor growth in vivo", *Cancer Gene Ther.*, 12(1):84-89 (2005).

LeGal et al., "An Adenovirus Vector for Gene Transfer into Neurons and Glia in the Brain", *Science*, 259:988-990 (1993).

Levesque et al., Disruption of the CXCR4/CXCL12 chemotactic interaction during hematopoietic stem cell mobilization induced by GCSF or cyclophosphamide, *J. Clin. Investig.*, 111(2):187-196 (2003).

Lewis et al., "Differential responses of human tumor cell lines to anti-p185$^{HER2}$ monoclonal antibodies", *Cancer Immunol. Immunother.*, 37:255-263 (1993).

Li et al., "Upregulation of CXCR4 is essential for HER2-mediated tumor metastasis", *Cancer Cell*, 6:459-469 (2004).

Liotta, L., "An attractive force in metastasis", *Nature*, 410:24-25 (2001).

Lonberg et al., "Antigen-specific human antibodies from mice comprising four distinct genetic modifications", *Nature*, 368:856-859 (1994).

Lonberg et al., "Human Antibodies from Transgenic Mice", *Intern. Rev. Immunol.*, 13(1):65-93 (1995).

Lu et al., "Abnormal development of the hippocampal dentate gyrus in mice lacking the CXCR4 chemokine receptor", *Proc. Nat'l. Acad. Sci. U.S.A.*, 99(10):7090-7095 (2002).

Lu et al., "Evolution of HIV-1 coreceptor usage through interactions with distinct CCR5 and CXCR4 domains", *Proc. Nat'l. Acad. Sci. U.S.A.*, 94(12):6426-6431 (1997).

Malmqvist, M., "Biospecific interaction analysis using biosensor technology", *Nature*, 361:186-187 (1993).

Marasco et al., "Design, intracellular expression, and activity of a human anti-human immunodeficiency virus type 1 gp120 single-chain antibody", *Proc. Nat'l. Acad. Sci. U.S.A.*, 90:7889-7893 (1993).

Marks et al., "By-passing Immunization Human Antibodies from V-gene Libraries Displayed on Phage", *J. Mol. Biol.*, 222:581-597 (1991).

Marks et al., "By-Passing Immunization: Building High Affinity Human Antibodies by Chain Shuffling", *Bio/Tech.*, 10:779-783 (1992).

Martin et al., "Irreversible Coupling of Immunoglobulin Fragments to Preformed Vesicles", *J. Biol. Chem.*, 257(1):286-288 (1982).

Milstein et al., "Hybrid hybridomas and their use in immunohistochemistry", *Nature*, 305:537-540 (1983).

Morrison et al., "High-flow microinfusion: Tissue penetration and pharmacodynamics", *Am. J. Physiol.*, 266(1):R292-R305 (1994).

Morrison, S., "Success in specification", *Nature*, 368:812-813 (1994).

Muller et al., "Involvement of chemokine receptors in breast cancer metastasis", *Nature*, 410:50-56 (2001).

Murphy, P., "The Molecular Biology of Leukocyte Chemoattractant Receptors", *Annu. Rev. Immunol.*, 12:593-633 (1994).

Nagasawa et al., "Defects of B-cell lymphopoiesis and bone-marrow myelopoiesis in mice lacking the CXC chemokine PBSF/SDF-1", *Nature*, 382:635-638 (1996).

Neuberger, M., "Generating high-avidity human Mabs in mice", *Nature Biotech.*, 14(7):826 (1996).

Oberlin et al., "The CXC chemokine SDF-1 is the ligand for LESTR/fusin and prevents infection by T-cell-line-adapted HIV-1", *Nature*, 382:833-835 (1996).

Ottaiano et al., "Inhibitory effects of anti-CXCR4 antibodies on human colon cancer cells", *Cancer Immunol. Immunother.*, 54:781-791 (2004).

Pegram et al., "Antibody dependent cell-mediated cytotoxicity in breast cancer patients in Phase III clinical trials of a humanized anti-HER2 antibody", *Proc. Am. Assoc. Cancer Res.*, 38:602, #4044 (1997), (Abstract Only).

Pegram et al., "Inhibitory effects of combinations of HER-2/*neu* antibody and chemotherapeutic agents used for treatment of human breast cancers", *Oncogene*, 18:2241-2251 (1999).

Petit et al., "G-CSF induces stem cell mobilization by decreasing bone marrow SDF-1 and up-regulating CXCR4", *Nature Immunol.*, 3(7):687-694 (2002).

Phillips et al., "Epidermal Growth Factor and Hypoxia-induced Expression of CXC Chemokine Receptor 4 on Non-small Cell Lung Cancer Cells Is Regulated by the Phosphatidylinositol 3-Kinase/PTEN/AKT/Mammalian Target of Rapamycin Signaling Pathway and Activation of Hypoxia Inducible Factor-1α", *J. Biol. Chem.*, 280(23):22473-22481 (2005).

Pietras et al., "Antibody to HER-2/*neu* receptor blocks DNA repair after cisplatin in human breast and ovarian cancer cells", *Oncogene*, 9:1829-1838 (1994).

Porcile et al., "CXCR4 Activation Induces Epidermal Growth Factor Receptor Transactivation in an Ovarian Cancer Cell Line", *Ann. N.Y. Acad. Sci.*, 1030:162-169 (2004).

Porcile et al., "Stromal cell-derived factor-1α (SDF-1α/CXCL12) stimulates ovarian cancer cell growth through the EGF receptor transactivation", *Exp. Cell Res.*, 308:241-253 (2005).

Ramakrishnan et al., "Comparison of the Selective Cytotoxic Effects of Immunotoxins Containing Ricin A Chain or Pokeweed Antiviral Protein and Anti-Thy 1.1 Monoclonal Antibodies", *Cancer Res.*, 44:201-208 (1984).

Scarlatti et al., "In vivo evolution of HIV-1 co-receptor usage and sensitivity to chemokine-mediated suppression", *Nat. Med.*, 3(11):1259-1265 (1997).

Schall, T., "The Chemokines", in *The Cytokine Handbook*, 2nd Ed., Thomson, A. Editor, Academic Press, New York, NY, Chapter 22, pp. 418-460 (1994).

Schols et al., "HIV Co-receptors as Targets for Antiviral Therapy", *Curr. Top. Med. Chem.*, 4(9):883-893 (2004).

Scott et al., "Searching for Peptide Ligands with an Epitope Library", *Science*, 249:386-390 (1990).

Shaheen et al., "Antiangiogenic Therapy Targeting the Tyrosine Kinase Receptor for Vascular Endothelial Growth Factor Receptor Inhibits the Growth of Colon Cancer Liver Metastasis and Induces Tumor and Endothelial Cell Apoptosis", *Cancer Res.*, 59:5412-5416 (1999).

Shalaby et al., "Development of Humanized Bispecific Antibodies Reactive with Cytotoxic Lymphocytes and Tumor Cells Overexpressing the HER2 Protooncogene", *J. Exp. Med.*, 175:217-225 (1992).

Shopes, B., "A Genetically Engineered Human IgG Mutant With Enhanced Cytolytic Activity", *J. Immunol.*, 148(9):2918-2922 (1992).

Slamon et al., "Studies of the HER-2/*neu* Proto-oncogene in Human Breast and Ovarian Cancer", *Science*, 244:707-712 (1989).

Sliwkowski et al., "Nonclinical Studies Addressing the mechanism of Action of Trastuzumab (Herceptin)", *Semin. Oncol.*, 26(4 Suppl. 12):60-70 (1999).

Staller et al., "Chemokine receptor CXCR4 downregulated by von Hippel-Lindau tumour suppressor pVHL", *Nature*, 425:307-311 (2003).

Stevenson et al., "A chimeric antibody with dual Fc regions (*bis*FabFc) prepared by manipulations at the IgG hinge", *Anti-Cancer Drug Des.*, 3:219-230 (1989).

Suresh et al., "Bispecific Monoclonal Antibodies from Hybrid Hybridomas", *Meth. Enzymol.*, 121:210-228 (1986).

Taichman et al., "Use of the Stromal Cell-derived Factor-1/CXCR4 Pathway in Prostate Cancer Metastasis to Bone", *Cancer Res.*, 62:1832-1837 (2002).

Tan et al., "Overexpression of the c-erbB-2 Gene Enhanced Intrinsic Metastasis Potential in Human Breast Cancer Cells without Increasing Their Transformation Abilities", *Cancer Res.*, 57:1199-1205 (1997).

Tashiro et al., "Signal Sequence Trap: A Cloning Strategy for Secreted Proteins and Type 1 Membrane Proteins", *Science*, 261:600-603 (1993).

Taylor et al., "$CD4^{+CD25+}$ Immune Regulatory Cells Are Required for Induction of Tolerance to Alloantigen via Costimulatory Blockade", *J. Exp. Med.*, 193(11):1311-1318 (2001).

Taylor et al., "The infusion of ex vivo activated and expanded $CD4^{+CD25+}$ immune regulatory cells inhibits graft-versus-host disease lethality", *Blood*, 99(10):3493-3499 (2002).

Traunecker et al., "Bispecific single chain molecules (janusins) target cytotoxic lymphocytes on HIV infected cells", *EMBO J.*, 10(12):3655-3659 (1991).

Tutt et al., "Trispecific F(ab')$_3$ Derivatives That Use Cooperative Signaling via the TCR/CD3 Complex and CD2 to Activate and Redirect Resting Cytotoxic T Cells", *J. Immunol.*, 147(1):60-69 (1991).

Vaday et al., "CXCR4 and CXCL12 (SDF-1) in prostate cancer: inhibitory effects of human single chain FV antibodies", *Clin. Cancer Res.*, 10(16):5630-5639 (2004).

Vitetta et al., "Redesigning Nature's Poisons to Create Anti-Tumor Reagents", *Science*, 238:1098-1104 (1987).

Warren et al., "Regulation by Vascular Endothelial Growth Factor of Human Colon Cancer Tumorigenesis in a Mouse Model of Experimental Liver Metastasis", *J. Clin. Invest.*, 95:1789-1797 (1995).

Wilkinson, D., "Ultimate Abs", *Scientist*, 14(8):25-28 (2000).

Yang et al., "Cellular and Humoral Immune Responses to Viral Antigens Create Barriers to Lung-Directed Gene Therapy with Recombinant Adenoviruses", *J. Virol.*, 69(4):2004-2015 (1995).

Yarden et al., "Untangling the ErbB Signalling Network", *Mol. Cell Biol.*, 2:127-137 (2001).

Yu et al., "Overexpression of ErbB2 in cancer and ErbB2-targeting strategies", *Oncogene*, 19:6115-6121 (2000).

Zebedee et al., "Human combinatorial antibody libraries to hepatitis B surface antigen", *Proc. Nat'l. Acad. Sci. U.S.A.*, 89:3175-3179 (1992).

Zeelenberg et al., "The Chemokine Receptor CXCR4 Is Required for Outgrowth of Colon Carcinoma Micrometastases", *Cancer Res.*, 63:3833-3839 (2003).

Zhou et al., "Structural and Functional Characterization of Human CXCR4 as a Chemokine Receptor and HIV-1 Co-Receptor by Mutagenesis and Molecular Modeling Studies", 9th *Conference on Retroviruses and Opportunistic Infections*, 189-M, Session 39 Poster Session, (2002), (Abstract Only).

Zou et al., "Bone Marrow Is a Reservoir for $CD4^{+CD25+}$ Regulatory T Cells that Traffic through CXCL12/CXCR4 Signals", *Cancer Res.*, 64:8451-8455 (2004).

Zuckermann et al., "Discovery of Nanomolar Ligands for 7-Transmembrane G-Protein-Coupled Receptors from a Diverse N-(Substituted)glycine Peptoid Library", *J. Med. Chem.*, 37:2678-2685 (1994).

Kucia, Magda et al. "CXCR4-SDF-1 signalling, locomotion, chemotaxis and adhesion." *Journal of Molecular Histology*. 35.3(2004):233-245.

\* cited by examiner

Fig. 1

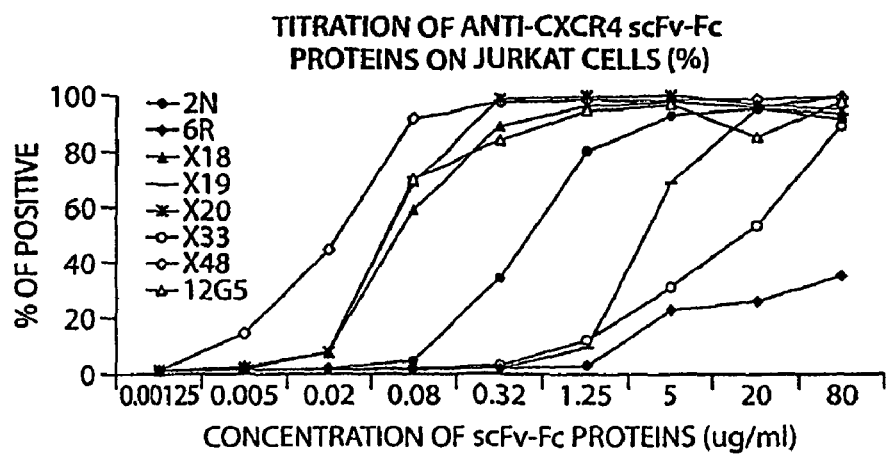
Fig. 9C
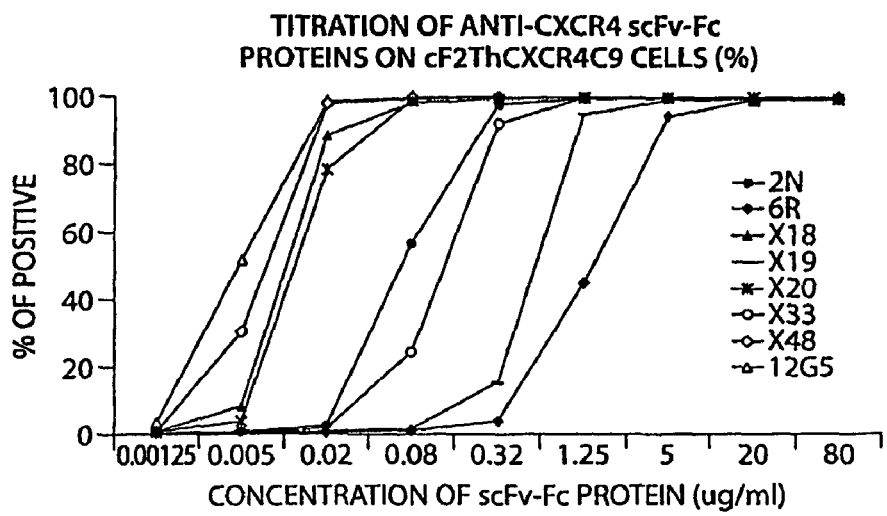
Fig. 9D
EC50 OF ANTI-CXCR4 scFv-Fc FUSION PROTEINS (MFI, ug/ml)
| μg/ml | 2N | 6R | X18 | X19 | X20 | X33 | X48 | 12G5 |
|---|---|---|---|---|---|---|---|---|
| JURKAT | 2.69 | 7.28 | 5.07 | 16.24 | 0.7 | 18.45 | 0.09 | 16.95 |
| CF2ThCXCR4 | 9.68 | 26.15 | 0.92 | 16.03 | 1.18 | 7.73 | 0.49 | 0.70 |
Fig. 9E
EC50 OF ANTI-CXCR4 scFv-Fc FUSION PROTEINS (%, ug/ml)
| μg/ml | 2N | 6R | X18 | X19 | X20 | X33 | X48 | 12G5 |
|---|---|---|---|---|---|---|---|---|
| JURKAT | 0.60 | 4.09 | 0.07 | 3.65 | 0.06 | 14.05 | 0.03 | 0.06 |
| CF2ThCXCR4 | 0.07 | 1.60 | 0.01 | 0.72 | 0.01 | 0.17 | 0.009 | 0.005 |
Fig. 9F

BENOVIC & MARCHESE, CANCER CELL 6;429, 2004

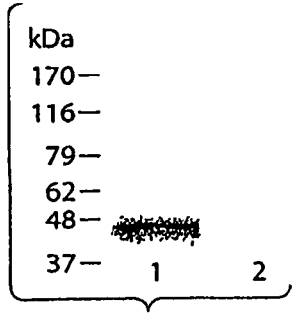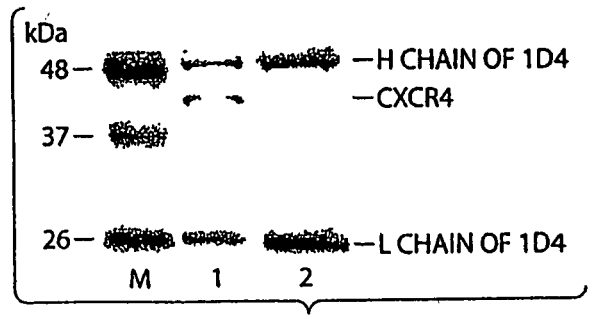
Fig. 16A          Fig. 16B
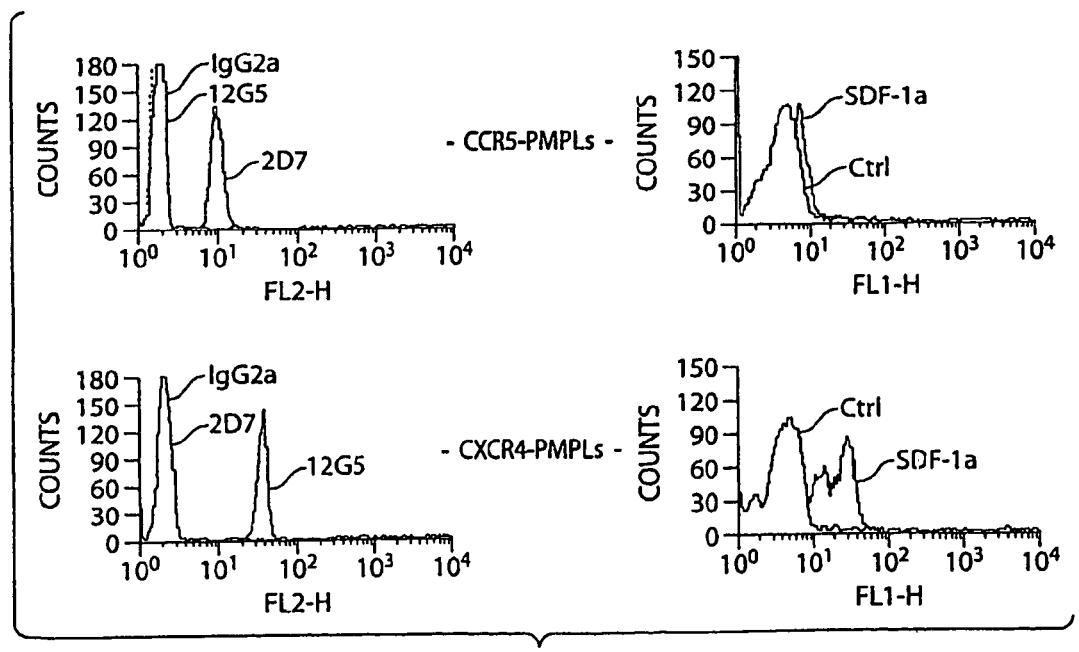
Fig. 16C

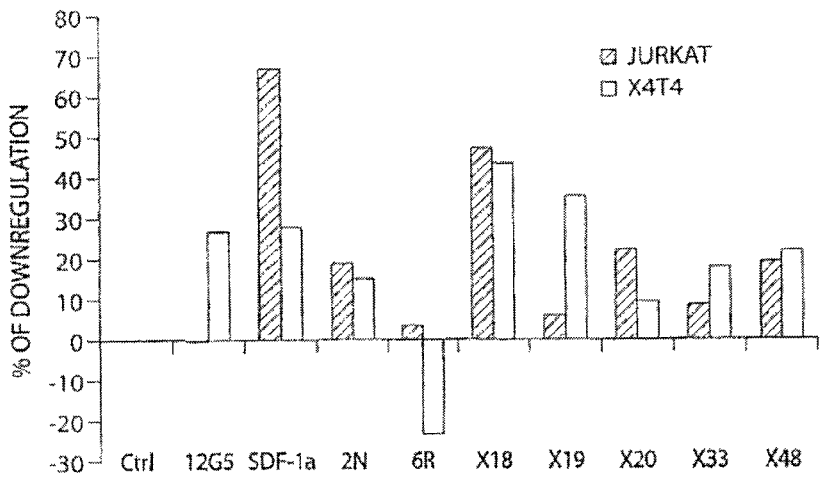

Fig. 19

```
N-term.

1                                      38
Human:      MEGISIYTSDNYTEEMGSGDYDSMKEPCFREENANFNK    (SEQ ID NO:60)
Macaque:    ----------------------I--------------R    (SEQ ID NO:61)
Mouse:      --P---------S--V-------N-----D---VH--R    (SEQ ID NO:62)

ECL1

97         110
Human:      DAVANWYFGNFLCK    (SEQ ID NO:63)
Macaque:    -------------     (SEQ ID NO:64)
Mouse:      --M-D---K-----    (SEQ ID NO:65)

ECL2

176                         202
Human:      NV...SEADDRYICDRFYPNDLWVVVFQFQ    (SEQ ID NO:66)
Macaque:    S-...------------------------    (SEQ ID NO:67)
Mouse:      D-SQGDI-QG------L--DS--M-----    (SEQ ID NO:68)

ECL3

262                282
Human:      DSFILLEIIKQGCEFENTVHK    (SEQ ID NO:69)
Macaque:    --------------------    (SEQ ID NO:70)
Mouse:      ------GV------D--SI---   (SEQ ID NO:71)
```

Fig 20

```
Wild-type CXCR4   1:MEGISIYTSDNYTEEMGSGDYDSMKEPCFREENANFNKIFLPTTYSIIFLTGIVGNLVILVMGY  80
Delta-N25-CXCR4   1:M-------------------------------------***********************  47
Delta-N31-CXCR4   1:M-------------------------------------------------**********  41

Wild-type CXCR4  81:QKKLRSMTDKYRLHLSVADLLFVITLPFWAVDAVANWYFGNFLCKAVHVIYTVNLYSSVLILAFISLDRYLAIVHATNSQ 160
Delta-N25-CXCR4  48:********************************************************************************* 127
Delta-N31-CXCR4  42:********************************************************************************* 121

Wild-type CXCR4 161:RPRKLLAEKVVYGVWIPALLLTIPDFIFANVSEADDRYICDRFYPNDLWVVFQFQHIMVGLILPGIVILSCYCIIISK 240
Delta-N25-CXCR4 128:********************************************************************************* 206
Delta-N31-CXCR4 122:********************************************************************************* 201

Wild-type CXCR4 241:LSHSKGHQKRKALKTTVILILAFFACWLPYYIGISIDSFILLEIIKQGCEFENTVHKWISITEALAFFHCCLNPILYAFL 320
Delta-N25-CXCR4 207:********************************************************************************* 286
Delta-N31-CXCR4 202:********************************************************************************* 281

Wild-type CXCR4 321:GAKFKTSAQHALTSVSRGSSLKILSKGKRGGHSSVSTESESSSFHSSGTETSQVAPALES-380 (SEQ ID NO:72)
Delta-N25-CXCR4 287:******************************************************-346 (SEQ ID NO:73)
Delta-N31-CXCR4 282:**************************************************-342 (SEQ ID NO:74)
```

FIGURE 21

A3-2mets x 400 (UNTREATED)

A11-INTRAVASC. met x 200 (UNTREATED)

A11-SMALL met x 40 (UNTREATED)

D33-NO met x 40 (48Fc TREATED)

ANTIBODIES AGAINST CXCR4 AND METHODS OF USE THEREOF

RELATED APPLICATIONS

This application is a national stage application, filed under 35 U.S.C. §371, of International Application No. PCT/US2006/005691, filed on Feb. 15, 2006 which claims the benefit of U.S. Ser. No. 60/654,377, filed Feb. 18, 2005.

STATEMENT AS TO FEDERALLY SPONSORED RESEARCH

This invention was funded in part by the U.S. Government under grant numbers AI052829 and AI061318, awarded by the National Institutes of Health, and grant number W8IXWH-05-1-0417, awarded by the U.S. Army Medical Research and Materiel Command (USAMRMC). The Government has certain rights in the invention.

INCORPORATION OF SEQUENCE LISTING

The contents of the text file named "20363_033NATL_ST25.txt", which was created on Apr. 18, 2012 and is 35.9 KB in size, are hereby incorporated by reference in their entireties.

FIELD OF THE INVENTION

This invention relates generally to anti-CXCR4 antibodies as well as to methods of use thereof.

BACKGROUND

Chemokines are a superfamily of mostly small, secreted proteins that function in leukocyte trafficking, recruiting, and recirculation. These proteins also play an important role in many pathophysiological processes, including allergic responses, chemotaxis, infectious and autoimmune diseases, angiogenesis, inflammation, tumor growth, tumor metastasis, and hematopoietic development. All chemokines signal through seven transmembrane domain G-protein coupled receptors ("GPCRs"). (See Baggiolini et al., Ann. Rev. Immunol. 15:675 (1997); Schall, in *The Cytokine Handbook*, $2^{nd}$ ed. Thomson, A. editor, Academic Press, New York, pages 418-60 (1994); Murphy et al., Annu. Rev. Immunol. 12:593 (1994)). The various chemokine receptors are known to have overlapping chemokine ligand specificities. At least seventeen chemokine receptors are known. For many of these receptors, several different chemokines can signal through the same receptor. The finding that HIV viruses use some chemokine receptors as co-receptors for entry into cells has generated an increased interest in chemokine receptor research. (See, Deng et al., Nature 381:661 (1996); Alkahatib et al., Science 272:955 (1996); Broder, J. Leukocyte Biol. 62:20 (1997)).

Chemokines are divided into subfamilies based on conserved amino acid sequence motifs. Most chemokine family members have at least four conserved cysteine residues that form two intramolecular disulfide bonds. The chemokine subfamilies can be defined by the position of the first two of these cysteine residues.

The alpha ($\alpha$) subfamily is also known as the CXC chemokines because they have one amino acid separating these first two cysteine residues. This group can be further subdivided based on the presence or absence of a glu-leu-arg (ELR) (SEQ ID NO:59) amino acid motif immediately preceding the first cysteine residue. There are currently at least five CXC-specific receptors, which are designated CXCR1 to CXCR5. The $ELR^+$ chemokines bind to CXCR2 and generally act as neutrophil chemoattractants and activators, whereas the $ELR^-$ chemokines bind CXCR3 to CXCR5 and act primarily on lymphocytes.

In the beta ($\beta$) subfamily, which is also referred to as the CC chemokines, the first two cysteines are adjacent to one another and there are no intervening amino acids. There are currently 24 distinct human $\beta$ subfamily members. The receptors for this group are designated CCR1 to CCR11. Target cells for various CC chemokine family members include most types of leukocytes, including monocytes, T lymphocytes, B lymphocytes, dendritic cells, natural killer cells, eosinophils and basophils.

There are also two known proteins having chemokine homology that fall outside of the $\alpha$ and $\beta$ subfamilies. Specifically, lymphotactin is the lone member of the gamma ($\gamma$) class. It is also known as a C chemokine. This class of chemokines has lost the first and third cysteines. Thus, the lymphotactin receptor is designated XCR1.

Additionally, fractalkine, the only known member of the delta ($\delta$) class, which is also known as a $CX_3C$ chemokine, has three intervening amino acids between the first two cysteine residues. Fractalkine is unique among chemokines because it is a transmembrane protein whose N-terminal chemokine domain is fused to a long mucin-like stalk. The fractalkine receptor is referred to as $CX_3CR1$.

SUMMARY OF THE INVENTION

The invention encompasses antibodies (or fragments thereof) that specifically bind to the chemokine receptor CXCR4. For example, the antibody may be a monoclonal antibody, an scFv antibody, an scFv-Fc fusion, a dAb (domain antibody), $F_{ab}$, $F_{ab'}$ and $F_{(ab')2}$ fragments, a single chain antibody, a minibody, and/or a diabody. Antibodies of the invention are identified by panning two human non-immune scFv libraries having a total of $2.7 \times 10^{10}$ members with CXCR4 proteoliposomes. While 7 antibodies that were found to specifically bind to the CXCR4 proteoliposomes are described in detail herein, those skilled in the art will recognize that any CXCR4-specific antibodies identified according to the methods described herein are also encompassed by the instant invention.

For example, the invention provides a human monoclonal antibody which binds to the chemokine receptor CXCR4, wherein the monoclonal antibody is selected from the group consisting of mAb 2N, mAb 6R, mAb 18, mAb 19, mAb 20, mAb 33 and mAb 48. mAb 2N contains one or more sequences selected from the group consisting of SEQ ID NOS: 2 and 10; mAb 6R contains one or more sequences selected from the group consisting of SEQ ID NOS: 3 and 11; mAb 18 contains one or more sequences selected from the group consisting of SEQ ID NOS: 4 and 12; mAb 19 contains one or more sequences selected from the group consisting of SEQ ID NOS: 5 and 13; mAb 20 contains one or more sequences selected, from the group consisting of SEQ ID NOS: 6 and 14; mAb 33 contains one or more sequences selected from the group consisting of SEQ ID NOS: 7 and 15; and mAb 48 contains one or more sequences selected from the group consisting of SEQ ID NOS: 8 and 16.

The invention provides an anti-CXCR4 antibody having a heavy chain with three CDRs comprising an amino acid sequence selected from the group consisting of the amino acid sequences SYGMH (SEQ ID NO:17), VISYDGSNKYYADSVKG (SEQ ID NO:18), and DLVAAAGTAFDI (SEQ ID NO:19) and/or an anti-CXCR4 antibody having a light chain with three CDRs comprising an amino acid sequence selected from the group consisting of the amino acid sequences TGTISDVGGHNFVS (SEQ ID NO:20), EVTKRPA (SEQ ID NO:21), and SSYGGSNDVI (SEQ ID NO:22).

Also provided is an anti-CXCR4 antibody having a heavy chain with three CDRs comprising an amino acid sequence selected from the group consisting of the amino acid sequences SNFVAWN (SEQ ID NO:23), RTYYRSRW-YNDYAVSVQS (SEQ ID NO:24), and GQHSGFDF (SEQ ID NO:25) and/or an anti-CXCR4 antibody having a light chain with three CDRs comprising an amino acid sequence selected from the group consisting of the amino acid sequences TGNSNNVGNQGAA (SEQ ID NO:26), RNNNRPS (SEQ ID NO:27), and SAWDNRLKTYV (SEQ ID NO:28).

The invention further provides an anti-CXCR4 antibody having a heavy chain with three CDRs comprising an amino acid sequence selected from the group consisting of the amino acid sequences SYGIS (SEQ ID NO:29), WISAYN-GNTNYAQKLQG (SEQ ID NO:30), and DTPGIAAR-RYYYYGMDV (SEQ ID NO:31) and/or an anti-CXCR4 antibody having a light chain with three CDRs comprising an amino acid sequence selected from the group consisting of the amino acid sequences QGDSLRKFFAS (SEQ ID NO:32), GKNSRPS (SEQ ID NO:33), and NSRDSRDN-HQV (SEQ ID NO:34).

The invention also provides an anti-CXCR4 antibody having a heavy chain with three CDRs comprising an amino acid sequence selected from the group consisting of the amino acid sequences SYPMH (SEQ ID NO:35), VISSDGRNI-CYYPDSVKG (SEQ ID NO:36), and GGYHDFWSGPDY (SEQ ID NO:37) and/or an anti-CXCR4 antibody having a light chain with three CDRs comprising an amino acid sequence selected from the group consisting of the amino acid sequences RASQSVNTNLA (SEQ ID NO:38), GAS-SRAT (SEQ ID NO:39), and QHYGSSPLT (SEQ ID NO:40).

Further, the invention also provides an anti-CXCR4 antibody having a heavy chain with three CDRs comprising an amino acid sequence selected from the group consisting of the amino acid sequences SYAMS (SEQ ID NO:41), NIKQDGSEKYYVDSVKG (SEQ ID NO:42), and DQVS-GITIFGGKWRSPDV (SEQ ID NO:43) and/or an anti-CXCR4 antibody having a light chain with three CDRs comprising an amino acid sequence selected from the group consisting of the amino acid sequences QGDSLRSYYAS (SEQ ID NO:44), GKNNRPS (SEQ ID NO:45), and NSRSGSQRV (SEQ ID NO:46).

Additionally, the invention provides an anti-CXCR4 antibody having a heavy chain with three CDRs comprising an amino acid sequence selected from the group consisting of the amino acid sequences NYGLH (SEQ ID NO:47), VISHDGTKKYYADSVKG (SEQ ID NO:48), and DGGYC-SGGRCYSYGMDV (SEQ ID NO:49) and/or an anti-CXCR4 antibody having a light chain with three CDRs comprising an amino acid sequence selected from the group consisting of the amino acid sequences SGSRSNIGSNTVN (SEQ ID NO:50), TNNQRPS (SEQ ID NO:51), and LSFDSSLTSYV (SEQ ID NO:52).

The invention also provides an anti-CXCR4 antibody having a heavy chain with three CDRs comprising an amino acid sequence selected from the group consisting of the amino acid sequences RYGMH (SEQ ID NO:53), LISYDGSKT-FYGESVKG (SEQ ID NO: 54), and ATVTTDGYYYMDV (SEQ ID NO: 55) and/or an anti-CXCR4 antibody having a light chain with three CDRs comprising an amino acid sequence selected from the group consisting of the amino acid sequences SGSRSNIGGNTVN (SEQ ID NO:56), ANNQRPS (SEQ ID NO: 57), and AAWDDNLSGHVV (SEQ ID NO: 58).

mAb 6R has been found to specifically bind to an epitope on CXCR4 that contains the N-terminal region and the extracellular loop 3 region of CXCR4. Likewise, mAbs 2N, 33, and 48 have been found to specifically bind to an epitope on CXCR4 that contains the N-terminal region of CXCR4.

In addition, the binding of the antibodies of the invention blocks the function of SDF-1, the natural ligand for CXCR4.

The invention also encompasses monoclonal antibodies capable of binding to CXCR4 that recognize the same epitope as mAb 2N, mAb 6R, mAb 18, mAb 19, mAb 20, mAb 33, or mAb 48. Such antibodies may have the same apparent binding affinity of mAb 2N, mAb 6R, mAb 18, mAb 19, mAb 20, mAb 33, or mAb 48 and may compete with the binding of mAb 2N, mAb 6R, mAb 18, mAb 19, in Ab 20, mAb 33, or mAb 48 to CXCR4.

Also provided herein are scFv antibodies which bind to the chemokine receptor CXCR4, wherein the scFv antibody is selected from the group consisting of scFv antibody 2N, scFv antibody 6R, scFv antibody 18, scFv antibody 19, scFv antibody 20, scFv antibody 33, and scFv antibody 48. scFv 6R binds to an epitope on CXCR4 comprising the N-terminal region and the extracellular loop 3 region of CXCR4, whereas scFvs 2N, 33, and 48 bind to an epitope on CXCR4 comprising the N-terminal region of CXCR4.

The binding of scFv antibody 2N, scFv antibody 6R, scFv antibody 18, scFv antibody 19, scFv antibody 20, scFv antibody 33, and/or scFv antibody 48 to CXCR4 blocks the function of SDF-1.

Also provided are scFv antibodies capable of binding to CXCR4, wherein said scFv antibody binds to the same epitope as scFv antibody 2N, scFv antibody 6R, scFv antibody 18, scFv antibody 19, scFv antibody 20, scFv antibody 33, or scFv antibody 48. Such scFvs may have the same apparent binding affinity of scFv antibody 2N, scFv antibody 6R, scFv antibody 18, scFv antibody 19, scFv antibody 20, scFv antibody 33, or scFv antibody 48 and may competes with the binding of scFv antibody 2N, scFv antibody 6R, scFv antibody 18, scFv antibody 19, scFv antibody 20, scFv antibody 33, or scFv antibody 48 to CXCR4.

The binding of any of the scFvs of the invention to CXCR4 blocks the function of SDF-1, the natural ligand for CXCR4.

In addition, the invention also encompasses diabodies which recognize the chemokine receptor CXCR4. For example, the diabody may contain two binding sites that bind to an epitope on CXCR4 comprising amino acids 2-25 of the N-terminal region of CXCR4. Alternatively, the diabody may contain two binding sites that bind to an epitope on CXCR4 comprising the N-terminal region of CXCR4. The diabodies disclosed herein block the function of SDF-1, the natural ligand of CXCR4.

The invention also includes scFv-Fc fusions, dAbs (domain antibody), $F_{ab}$, $F_{ab'}$ and $F_{(ab')2}$ fragments, single chain antibodies and/or minibodies prepared from any of the scFv antibodies discovered according to the methods described herein.

Also provided are compositions containing any of the human monoclonal antibodies, scFv antibodies, scFv-Fc fusions, dAbs (domain antibodies), $F_{ab}$, $F_{ab'}$ and $F_{(ab')2}$ fragments, single chain antibodies and/or minibodies disclosed herein along with a carrier. Likewise, the invention further provides kits containing, in one or more containers, the compositions disclosed herein.

The invention also encompasses methods of preventing X4-tropic HIV-1 infection comprising administering a therapeutically or prophylactically effective amount of any of the human monoclonal antibodies, scFv antibodies, scFv-Fc fusions, dAbs (domain antibodies), $F_{ab}$, $F_{ab'}$ and $F_{(ab')2}$ fragments, single chain antibodies and/or minibodies disclosed herein to a patient susceptible to X4-tropic HIV-1 infection. The invention further encompasses the sue of a therapeutically or prophylactically effective amount of the human monoclonal antibodies, scFv antibodies, scFv-Fc fusions, dAbs (domain antibodies), $F_{ab}$, $F_{ab'}$ and $F_{(ab')2}$ fragments, single chain antibodies and/or minibodies of the invention in the manufacture of a medicament for the prevention of X4-tropic. HIV-1 infection.

Moreover, the invention also provides methods for preventing a disease or disorder associated with CXCR4 function or expression comprising administering a therapeutically effective amount of any of the human monoclonal antibodies, scFv antibodies, scFv-Fc fusions, dAbs (domain antibodies), $F_{ab}$, $F_{ab'}$ and $F_{(ab')2}$ fragments, single chain antibodies and/or minibodies disclosed herein to a person at risk of suffering from said disease or disorder. Also provided is the use of a therapeutically effective amount of the human monoclonal antibodies, scFv antibodies, scFv-Fc fusions, dAbs (domain antibodies), $F_{ab}$, $F_{ab'}$ and $F_{(ab')2}$ fragments, single chain antibodies and/or minibodies in the manufacture of a medicament for the prevention of a disease or disorder associated with CXCR4 function or expression. For example, the disease or disorder may be selected from the group consisting of X4-tropic HIV infection, cancer, and acute graft-versus-host disease.

Methods for treating or preventing cancer metastasis by administering a therapeutically effective amount of any of the human monoclonal antibodies, scFv antibodies, scFv-Fc fusions, dAbs (domain antibodies), $F_{ab}$, $F_{ab'}$ and $F_{(ab')2}$ fragments, single chain antibodies and/or minibodies disclosed herein to a patient suffering from a cancer involving tumor cells that express CXCR4 are also provided. The invention also provides for the use of a therapeutically effective amount of the human monoclonal antibodies, scFv antibodies, scFv-Fc fusions, dAbs (domain antibodies), $F_{ab}$, $F_{ab'}$ and $F_{(ab')2}$ fragments, single chain antibodies and/or minibodies of the invention in the manufacture of a medicament for the treatment or prevention of metastasis of a cancer involving tumor cells that express CXCR4. For example, tumor cells that express CXCR4 include, but are not limited to breast cancer, renal cell carcinoma, non-small cell lung cancer, prostate cancer, and glioblastoma. In some embodiments, this method also involves the co-administration of a therapeutically effective amount of an EGFR family antagonist. For example, the EGFR family antagonist may be a HER2 antagonist, such as Herceptin®, an EGFR antagonist, and/or a VEGFR antagonist.

Other methods for treating or preventing cancer metastasis according to the invention involve the administration of a therapeutically effective amount of any of the human monoclonal antibodies, scFv antibodies, scFv-Fc fusions, dAbs (domain antibodies), $F_{ab}$, $F_{ab'}$ and $F_{(ab')2}$ fragments, single chain antibodies and/or minibodies disclosed herein to a patient suffering from a hypoxic tumor, wherein said human monoclonal antibodies, scFv antibodies, scFv-Fc fusions, dAbs (domain antibodies), $F_{ab}$, $F_{ab'}$ and $F_{(ab')2}$ fragments, single chain antibodies and/or minibodies block or neutralize increased CXCR4 activity resulting from HIF induction in said hypoxic tumor. Similarly, a therapeutically effective amount of the human monoclonal antibodies, scFv antibodies, scFv-Fc fusions, dAbs (domain antibodies), $F_{ab}$, $F_{ab'}$ and $F_{(ab')2}$ fragments, single chain antibodies and/or minibodies of the invention can be used in the manufacture of a medicament for the treatment or prevention of metastasis of a hypoxic tumor, wherein the human monoclonal antibodies, scFv antibodies, scFv-Fc fusions, dAbs (domain antibodies), $F_{ab}$, $F_{ab'}$ and $F_{(ab')2}$ fragments, single chain antibodies and/or minibodies block or neutralize increased CXCR4 activity resulting from HIF induction in the hypoxic tumors. Examples of hypoxic tumors include, e.g., any solid tumor characterized by HIF-dependent CXCR4 activation. For example, the hypoxic tumor may be renal cell carcinoma, breast cancer, non-small cell lung cancer, prostate cancer, and glioblastoma.

Also encompassed by the invention are methods of mobilizing $CD34^+$ stem cells from the bone marrow by an effective amount of any of the human monoclonal antibodies, scFv antibodies, scFv-Fc fusions, dAbs (domain antibodies), $F_{ab}$, $F_{ab'}$ and $F_{(ab')2}$ fragments, single chain antibodies and/or minibodies disclosed herein to a patient in need of such treatment. Likewise, an effective amount of the human monoclonal antibodies, scFv antibodies, scFv-Fc fusions, dAbs (domain antibodies), $F_{ab}$, $F_{ab'}$ and $F_{(ab')2}$ fragments, single chain antibodies and/or minibodies disclosed herein can be used in the manufacture of a medicament for the mobilization of $CD34^+$ stem cells from the bone marrow. Such methods and uses may also include the co-administration of one or more second mobilizing agents such as G-CSF, GM-CSF, AMD3100, AMD070, and/or structural analogues thereof to the patient. Preferred second mobilizing agents may include AMD3100 and/or AMD070.

The invention also provides for the use of an effective amount of an antibody fragment comprising an amino acid sequence selected from the group consisting of SEQ ID NOS: 2-8 and 10-58 in the manufacture of a medicament for the mobilization of $CD34^+$ stem cells from the bone marrow. Such uses may also include the co-administration of one or more second mobilizing agents such as G-CSF, GM-CSF, AMD3100, AMD070, and/or structural analogues thereof to the patient. Preferred second mobilizing agents may include AMD3100 and/or AMD070. Those skilled in the art will recognize that suitable antibody fragments include, for example, human monoclonal antibodies, scFv antibodies, scFv-Fc fusions, dAbs (domain antibodies), $F_{ab}$, $F_{ab'}$ and $F_{(ab')2}$ fragments, single chain antibodies and/or minibodies.

Any of the human monoclonal antibodies, scFv antibodies, scFv-Fc fusions, dAbs (domain antibodies), $F_{ab}$, $F_{ab'}$ and $F_{(ab')2}$ fragments, single chain antibodies and/or minibodies of the invention can be used treat graft-versus-host disease by administering therapeutically effective amounts to a patient suffering from or at risk of suffering from graft-versus-host disease. For example, the therapeutically effective amount of the human monoclonal antibodies, scFv antibodies, scFv-Fc fusions, dAbs (domain antibodies), $F_{ab}$, $F_{ab'}$ and $F_{(ab')2}$ fragments, single chain antibodies and/or minibodies disclosed herein may be used in the manufacture of a medicament for the treatment or prevention of graft-versus-host disease. Such methods and uses may also include the co-administration of one or more mobilizing agents to the patient. For example, one or more of G-CSF, GM-CSF, AMD3100, AMD070, and/or structural analogues thereof may be co-administered.

The invention also provides methods of blocking chemotaxis of CXCR4-expressing cells in response to the chemokine SDF-1 by administering an effective amount of any of human monoclonal antibodies, scFv antibodies, scFv-Fc fusions, dAbs (domain antibodies), $F_{ab}$, $F_{ab'}$ and $F_{(ab')2}$ fragments, single chain antibodies and/or minibodies disclosed herein, or a combination thereof, to a subject in which blocking the chemotaxis of CXCR4-expressing cells is desired. For example, any of the human monoclonal antibodies, scFv antibodies, scFv-Fc fusions, dAbs (domain antibodies), $F_{ab}$, $F_{ab'}$ and $F_{(ab')2}$ fragments, single chain antibodies and/or minibodies described herein (or any combination thereof) can be used in the manufacture of a medicament for blocking chemotaxis of CXCR4-expressing cells in response to the chemokine SDF-1. Examples of suitable CXCR4-expressing cells include, but are not limited to Jurkat T-cells, T-cells, breast cancer cells, and tumor cells.

The invention also describes methods of inhibiting the formation of new tumor blood vessels in cancer therapy by administering an effective amount of any of the human monoclonal antibodies, scFv antibodies, scFv-Fc fusions, dAbs (domain antibodies), $F_{ab}$, $F_{ab'}$ and $F_{(ab')2}$ fragments, single chain antibodies and/or minibodies disclosed herein, or a combination thereof, to a patient suffering from a cancer in which hypoxia leads to local secretion of SDF-1, thereby blocking the interaction of SDF-1 and CXCR4, wherein blocking the interaction of SDF-1 and CXCR4 inhibits recruitment of endothelial cell precursors to aid in the formation of new tumor blood vessels. Specifically, any of the human monoclonal antibodies, scFv antibodies, scFv-Fc fusions, dAbs (domain antibodies), $F_{ab}$, $F_{ab'}$ and $F_{(ab')2}$ fragments, single chain antibodies and/or minibodies of the invention (or any combination thereof) can be used in the manufacture of a medicament for inhibiting the formation of new tumor blood vessels in cancer therapy by blocking the interaction of SDF-1 and CXCR4 in a cancer in which hypoxia leads to the local secretion of SDF-1, wherein blocking the interaction of SDF-1 and CXCR4 inhibits recruitment of endothelial cell precursors to aid in the formation of new tumor blood vessels. By way of non-limiting example, the cancer in which hypoxia leads to local secretion of SDF-1 may be renal cell carcinoma.

Finally, the invention also encompasses methods of inhibiting tumor cell angiogenesis in a patient suffering from cancer by administering an effective amount of any of the human monoclonal antibodies, scFv antibodies, scFv-Fc fusions, minibodies, and/or diabodies disclosed herein in combination with an anti-VEGF antibody or agent (e.g. Avastin™) to the patient, thereby blocking the synergistic effect of VEGF and SDF-1 on tumor cell angiogenesis. Any of the human monoclonal antibodies, scFv antibodies, scFv-Fc fusions, dAbs (domain antibodies), $F_{ab}$, $F_{ab'}$ and $F_{(ab')2}$ fragments, single chain antibodies and/or minibodies described herein can be used in combination with an anti-VEGF antibody or agent in the manufacture of a medicament for inhibiting tumor cell angiogenesis in a cancer by blocking the synergistic effect of VEGF and SDF-1 on tumor cell angiogenesis. For example, the cancer may be ovarian carcinoma or glioma.

The invention also encompasses nucleic acid delivery systems comprising a fusion protein, wherein the fusion proteins are prepared by recombinant techniques and contain a cell targeting moiety that specifically binds to a site on a target cell and a binding moiety that specifically binds to a nucleic acid segment and a nucleic acid segment containing a nucleic acid sequence of interest.

For example, suitable fusion proteins may contain an anti-CXCR4 antibody fragment fused to a human protamine protein or a fragment thereof. (See Song et al., Nature Biotechnology, 23(6):709-17 (2005), incorporated herein by reference in its entirety). Specifically, the anti-CXCR4 antibody fragment contains an amino acid sequence selected from the group consisting of SEQ ID NOS: 2-8 and 10-58 and specifically binds to a site on a CXCR4-expressing cells, while the human protamine protein (or fragment thereof) binds to a nucleic acid segment of interest. In one preferred embodiment, the nucleic acid segment of interest is an siRNA molecule. The instant invention also provides for the use of such fusion proteins in the manufacture of a medicament for the delivery of siRNA into said CXCR4-expressing cells.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features and advantages of the invention will be apparent from the following detailed description and claims.

BRIEF DESCRIPTION OF THE DRAWINGS

FIG. 1 shows the amino acid sequences of the following clones: 2N, 6R, X18, X19, X20, X33, and X48. The residues shown in bold represent the consensus amino acid sequence. In the consensus sequence, four or more clones having the same amino acid at a given position are designated as that amino acid. Framework Regions 1-4 (FW1-4), and Complementarity Determining Regions 1-3 (CDR1-3) for both the variable region of heavy chain ("VH") and the variable region of light chain ("VL") are shown for each clone. The VH and VL family designations are also provided.

FIG. 16 shows the results of the characterization of CXCR4 paramagnetic proteoliposomes (CXCR4-PMPLs). In FIG. 16A, [$^{35}$S] methionine and [$^{35}$S] cysteine labeled Cf2ThCXCR4C9 cells (lane 1) or CF2Th cells (lane 2) were lysed and conjugated with M280 Dynal beads coated with 1D4 mAb. After treatment with 2×SDS buffer, beads were pelletted, and supernatant was applied for autography analysis to test the purity of PMPLs. In FIG. 16B, 5×10$^7$ CXCR4-PMPLs (lane 1) or M280 Dynal beads coated with 1D4 mAb without CXCR4 protein (lane 2) were treated with 2×SDS-buffer for 1 hr at 55° C. followed by boiling for 5 min. The supernatant was used for SDS-PAGE analysis. In FIG. 16C, CXCR4-PMPLs (lower graphs) were stained with the CXCR4 conformation-dependent mAb 12G5-PE or its natural ligand SDF-1-Fc fusion protein followed by FITC-anti-mouse IgG. CCR5-PMPLs (upper graphs) and IgG2a-PE and CCR5 specific mAb 2D7-PE were used as negative controls.

FIG. 19 is a histogram showing the down regulation of CXCR4 protein expressed on cell surface. 1×10$^6$ Jurkat cells or cF2THCD4CXCR4 (X4T4) cells were incubated with 2 μg anti-CXCR4 scFv-Fc proteins or SDF-1a for 40 min at 37° C. Those proteins were acid stripped by Glycine-Hcl buffer (pH 2.3) and the presence of CXCR4 on cell surface was detected by staining with 12G5-PE followed by FACS analysis. % of down regulation=(1-MFI of samples treated with antibody or SDF-1a/MFI of samples treated with PBS (ctrl))*100%.

FIG. 20 is a sequence alignment showing the amino acid differences present among the human, rhesus macaque, and mouse CXCR4 extracellular domains.

FIG. 21 is a sequence alignment showing the amino acid sequences of wild-type CXCR4, ΔN25-CXCR4, and ΔN31-CXCR4. The shaded area shows the location of the C9 tag.

DETAILED DESCRIPTION OF THE INVENTION

Figure 2A:
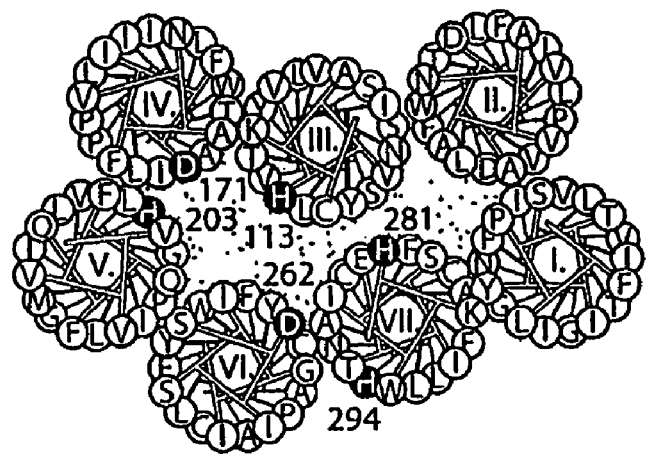
FIG. 2 is a schematic showing the amino acid sequence of the human CXCR4 receptor. Also provided are helical wheel (FIG. 2A) and serpentine diagrams (FIG. 2B) of the human CXCR4 receptor.
Figure 2B:
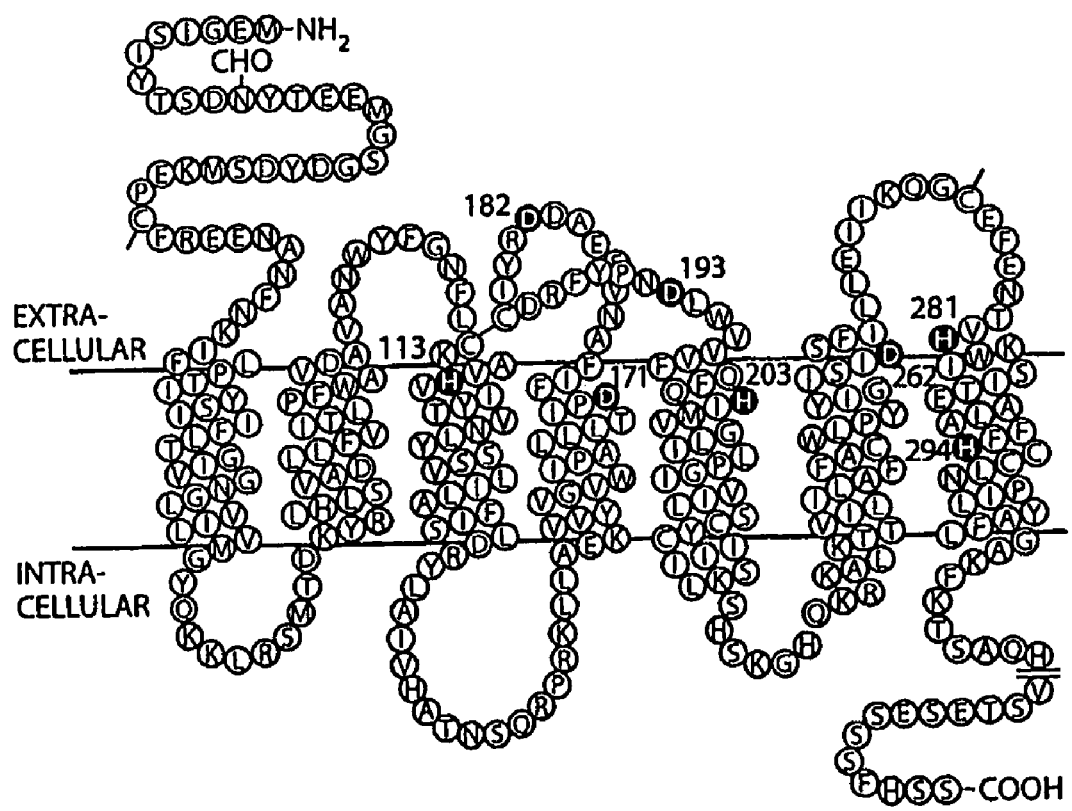

Chemokine (C-X-C motif) receptor 4 ("CXCR4") (also known as fusin, LESTR, or HUMSTR) is a G protein-coupled, 7-transmembrane domain chemokine receptor that is normally embedded within the membrane of a cell. CXCR4 is one of the best-characterized chemokine receptors. The 352 amino acid sequence (along with helical wheel and serpentine diagrams) of the human CXCR4 receptor is shown in FIGS. 2A and 2B. As shown in FIG. 2B, CXCR4 is characterized by four different extracellular regions: the N terminal domain, ECL1, ECL2, and ECL3.

CXCR4 is expressed at least in dendritic cells; naïve, non-memory T-cells; regulatory T cells; neurons and microglia; fresh primary monocytes; endothelial cells; neutrophils and B-cells; tumor cells, including but not limited to breast cancer cells, renal cell carcinoma cells, non-small cell lung cancer cells, prostate cancer cells, and glioblastoma cells; and CD34$^+$ hematopoietic stem cells. CXCR4 is essential for leukocyte trafficking; chemotaxis; B cell lymphopoiesis and myelopoiesis; stem cell migration; tumor or cancer cell metastasis; tumor cell angiogenesis; gastrointestinal tract vascularization; neuronal and germ cell migration; and X4-tropic HIV invasion of host cells. (See Li et al., Cancer Cell 6:459-69 (2004); Hernandez et al., Nat. Genet. 34:70-74 (2003); Nagasawa et al., Nature 382:635-38 (1996); Knaut et al., Nature 421:279-82 (2003); Kunwar et al., Nature 421: 226-27 (2003); Connor et al., J. Exp. Med. 185:621-28 (1997); and Scarlatti et al., Nat. Med. 3:1259-65 (1997)).

The alpha-chemokine stromal cell-derived factor (SDF-1) (also known as CXCL12) is the natural ligand for CXCR4. SDF-1α is the only chemokine that has just one chemokine receptor. (See Imitola et al., Proc. Natl. Acad. Sci. USA 101(52):18117-22 (2004); Lu et al., Proc. Natl. Acad. Sci. USA 99:2090-95 (2002). SDF-1 binding to CXCR4 activates multiple pathways that function to regulate cell invasion and migration. (See Benovic et al., Cancer Cell 6:429-30 (2004)). For example, in response to binding its ligand, CXCR4 triggers the migration and recruitment of immune cells. Additionally, this ligand-receptor pair may also play a role in the development of the nervous system. SDF-1 binding to CXCR4 also plays an important role in hematopoiesis and organogenesis. (See Nagasawi et al., Nature 382:635 (1996)). CXCR4 is also recognized by an antagonistic chemokine, the viral macrophage inflammatory protein II (vMIP-II) encoded by human herpesvirus type III. (See, Zhou et al., $9^{th}$ Conference on Retroviruses and Opportunistic Infections, Session 39 Poster Session, Abstract 189-M (2002)).

In addition, CXCR4 is a principal co-receptor for T-cell tropic strains of HIV-1 (commonly referred to as X4 viruses) fusion and entry of human white blood cells. CXCR4 is also required for infection by dual-tropic strains of HIV-1, which use both CXCR4 and CCR5 as its co-receptors. Moreover, CXCR4 also mediates CD4-independent infection by HIV-2. Specifically, CXCR4 associates with the surface CD4-gp120 complex before HIV enters target cells. X4-tropic HIV-1 strains tend to be more pathogenic and emerge later in infection than R5-tropic HIV strains, which use CCR5 as its co-receptor through a process referred to as M-tropic virus transmission.

Several compounds having anti-HIV-1 activity are believed to function through disruption of the envelope: CXCR4 interaction, including, for example, AMD3100. In addition, the CXCR4-specific monoclonal antibody, 12G5, as well as the CXCR4 ligands SDF-1 and SDF-1α have also been shown to have anti-HIV-1 activity in vitro. (See, e.g., Lu et al., Proc Natl Acad Sci USA 94(12):646-6431 (1997); Bluel et al., Nature 382(6594):829-33 (1996); Oberlin et al., Nature 382(6594):833-35 (1996)).

Proteoliposomes Containing CXCR4

Using the methods and techniques disclosed in U.S. Pat. No. 6,761,902, which is incorporated herein by reference in its entirety, it is possible to express integral membrane proteins (such as CXCR4) in large amounts, while maintaining such proteins in a wild-type conformation for extended periods of time. (See, Example 1, infra).

Specifically, a gene encoding the integral membrane protein in question can be introduced into a cell for the expression by any known means. An antigenic tag may also be inserted in the protein to assist in its purification and in the orientation of the protein on the solid surface. The cell expressing the integral membrane is then lysed in a buffer containing the appropriate detergent and protease inhibitors. The protein can be separated from other cellular debris by conventional means without harming the protein.

Next, the surface of paramagnetic beads is coated with streptavidin and a monoclonal antibody (e.g., the 1D4 antibody, which recognizes that C9 tag) directed against the antigenic tag found on the recombinant protein. The lysate containing the tagged protein is then incubated with these beads, and any unbound proteins are removed. The beads are then mixed with detergent-solubilized lipid containing Biotinyl-DOPE. In general, due to their amphipathic properties, transmembrane proteins can be solubilized only by agents that disrupt hydrophobic associations and destroy the membrane's lipid bilayer. Agents that are typically used are small amphipathic molecules which tend to form micelles in water, such as detergents. When mixed with membranes, the hydrophobic regions of the detergent bind to the transmembrane domain of proteins, thereby displacing the lipid molecules. The polar ends of detergents can either be charged (ionic) or uncharged (non-ionic). Although integral membrane proteins can be maintained in a native conformation in a detergent solution, over time many such solubilized proteins will undergo denaturation and aggregation.

When a detergent is removed from a transmembrane protein-detergent complex in the absence of phospholipids, the membrane protein molecules usually denature, aggregate, and precipitate out of solution. If, however, the purified protein is mixed with phospholipids prior to removal of the detergent, the active protein can insert into the lipid bilayer formed by these phospholipids. In this manner, functionally active integral membrane proteins can be reconstituted from purified components. Integral membrane proteins, which are properly reconstituted into its native lipid environment are stable for extended periods of time.

A critical factor for maintaining a functional conformation of a membrane protein during its purification is the choice of detergent used to solubilize the protein. The detergent that is best suited for a given membrane protein can typically determined empirically. Detergents recommended for gentle solubilization of membrane proteins include, for example, alkyl glucopyranosides (such as C8-GP and C9-GP), alkyl thioglucopyranosides (such as C8-tGP, C10-M, C12-M, Cymal-5, Cymal-6, and Cymal-7), alkyl sucroses (such as HECAMEG), digitonin, CHAPSO, hydroxyethylglucamides (such as HEGA-10), oligoethyleneglycol derivatives (such as C8E5, C8En, and C12E8), dodecylmaltopyranoside, and phenyl polyoxyethylenes (such as Triton X-100).

Typically, proteoliposomes have a spherical or ellipsoid shape, such as that of a bead or other pellet. A preferred shape is three-dimensional so that it can be coated on all sides. However, there can be substantial variability in the exact shape used, which will depend upon the way the proteoliposome is being used.

Proteoliposomes prepared in this way will typically contain only the integral membrane protein of interest. Stabilized proteoliposomes can be used in a variety of different methods. For example, because of the homogeneity of the reconstituted protein, the proteoliposomes can be used for structural characterization of the reconstituted protein. In addition, high concentrations of the protein on the bead can be obtained. In this manner, the proteoliposome can be used as an immunogen to obtain antibodies to the native conformation of the protein.

Proteoliposomes can also be used to generate and to identify a range of antibodies. For example, antibodies that affect the interaction with the receptor binding sites can be directly screened for, for instance by using a direct binding assay. The antibody of interest can be added before or after the addition of the labeled proteoliposome, and the effect of the antibody on binding can be determined by comparing the degree of binding in that situation against a base line standard with that proteoliposome in the absence of the antibody.

Likewise, as described in detail Example 2, infra, a phage display library can be screened using the resulting proteoliposomes in order to find antibodies to a given protein or to find ligands that will bind to the protein. Specifically, the resulting beads can be incubated with a phage library to select the phage(s) that bind to the protein of interest. These phage can be easily isolated by magnetic separation of the beads from the library supernatant.

Moreover, proteoliposomes can also be used to screen libraries for a desired compound. For example, proteoliposomes can be used to screen complex chemical libraries of small molecular weight (<1000 daltons) compounds in order to identify high-affinity ligands. Such compounds could serve as lead compounds for the discovery of agonistic and antagonistic drugs.

Identification and Characterization of scFvs and Monoclonal Antibodies

Figure 3:
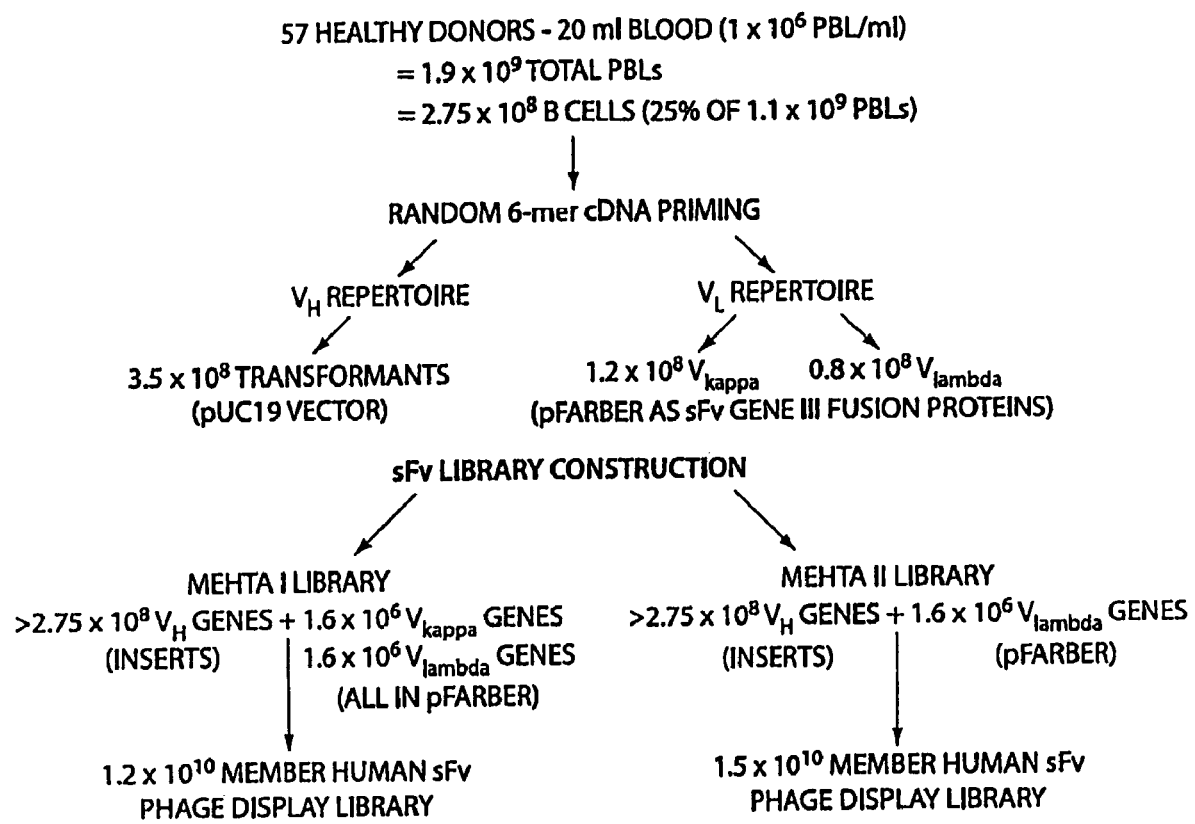
FIG. 3 is a diagram describing the genetic complexity of the Mehta I and II human scFv-Phage display libraries.

Following three rounds of panning of two human non-immune scFv libraries (having a total of $2.7\times10^{10}$ members) (see FIG. 3 and Example 2, supra) with wildtype CXCR4 proteoliposomes, five clones (scFvs 18, 19, 20, 33, and 48) were identified that specifically bind to CXCR4. A summary of the results of three rounds of panning against CXCR4-PMPLs is provided in Table 1. Individual clones were picked up from second and third round and phage scFv antibodies were applied for cell based ELISA. Those clones which bound to both CXCR4 positive and CXCR4 negative cells were identified as non-specific positive. Those clones which bound only to CXCR4 positive cells but not to parental cells were identified as CXCR4 specific positive. Unique clones were confirmed by sequence analysis. Five unique clones were identified among the 23 binders identified from the second round.

TABLE 1

Summary of Three Rounds of Antibody-Phage Panning on Human-CXCR4 Paramagnetic Proteoliposomes

|  | Input Number | Out Number | Non-Specific Positive | CXCR4-Specific Positive | Unique Clone |
|---|---|---|---|---|---|
| $1^{st}$ | $5 \times 10^{12}$ | $2.28 \times 10^6$ | NT | NT | NT |
| $2^{nd}$ | $5 \times 10^{12}$ | $9.35 \times 10^6$ | 433/768 | 23 | 5 |
| $3^{rd}$ | $5 \times 10^{12}$ | $5.67 \times 10^8$ | 90/96 | 1 | 1 |

NT, Not Tested

The N terminal region of CXCR4 has previously been reported to be sufficient for efficient binding of the functional ligand of CXCR4, SDF-1. (See Doranz et al., J. Virol. 7; 2752-61 (1999); Dragic, J. Gen Virol 82:1807-14 (2001)). Moreover, CXCR4 signaling involves other extracellular loops of CXCR4. Accordingly, antibodies against other CXCR4 domains are also desired. In order to obtain such antibodies, N terminal truncations of CXCR4 (ΔNT-CXCR4) were presented on paramagnetic proteoliposomes. These truncated paramagnetic proteoliposomes were used to select two human non-immune scFv libraries (having a total of $2.7\times10^{10}$ members) (see FIG. 3) according to the modified selection methods set forth in Example 2, supra. Two clones (2N and 6R) were identified according to this method.

Figure 4:
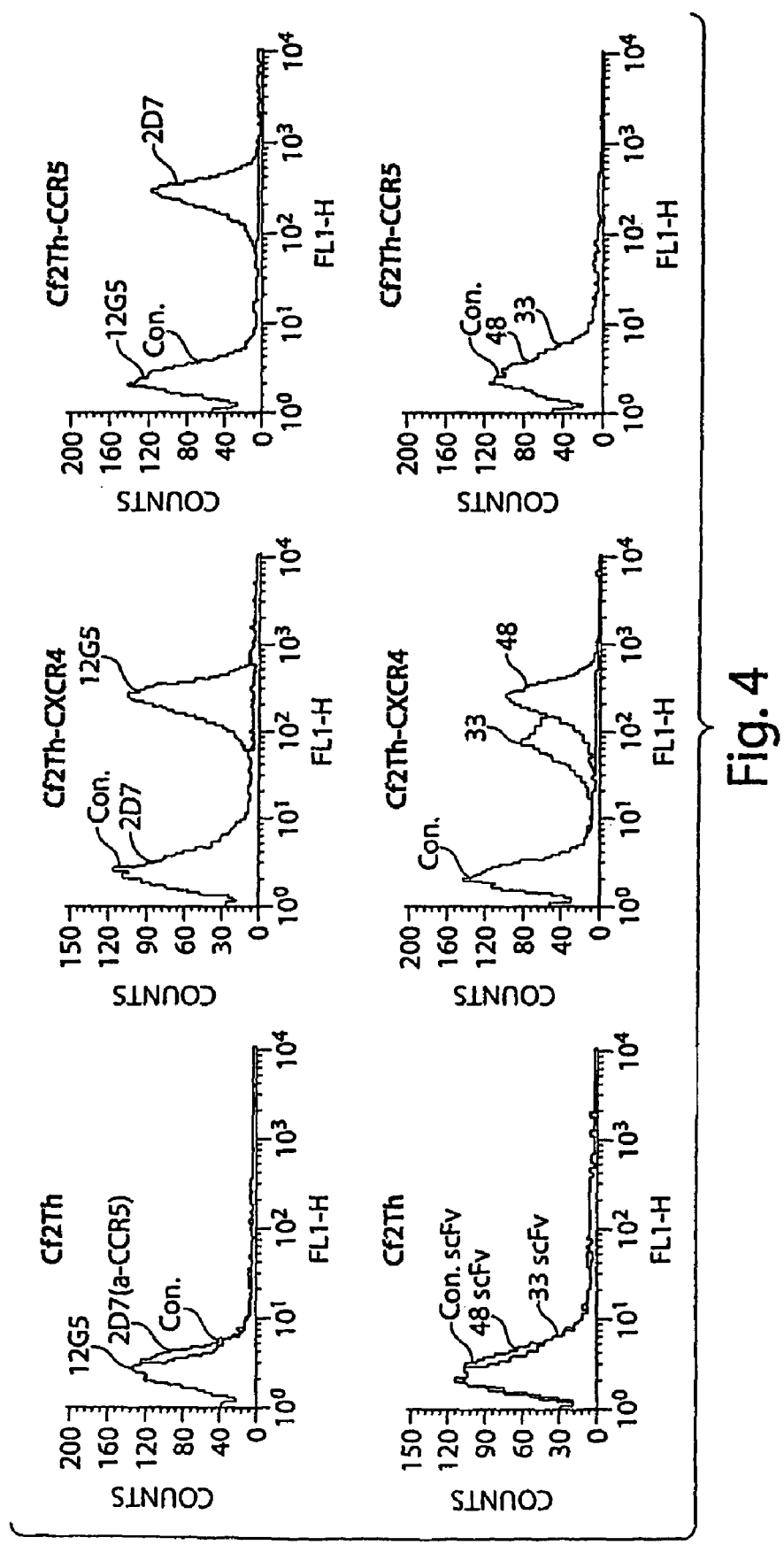
FIG. 4 is a series of FACS analysis graphs demonstrating that anti-CXCR4 scFvs 33 and 48 specifically bind to CXCR4. However, these scFvs do not bind to the closely related chemokine receptor CCR5.
Figure 5:
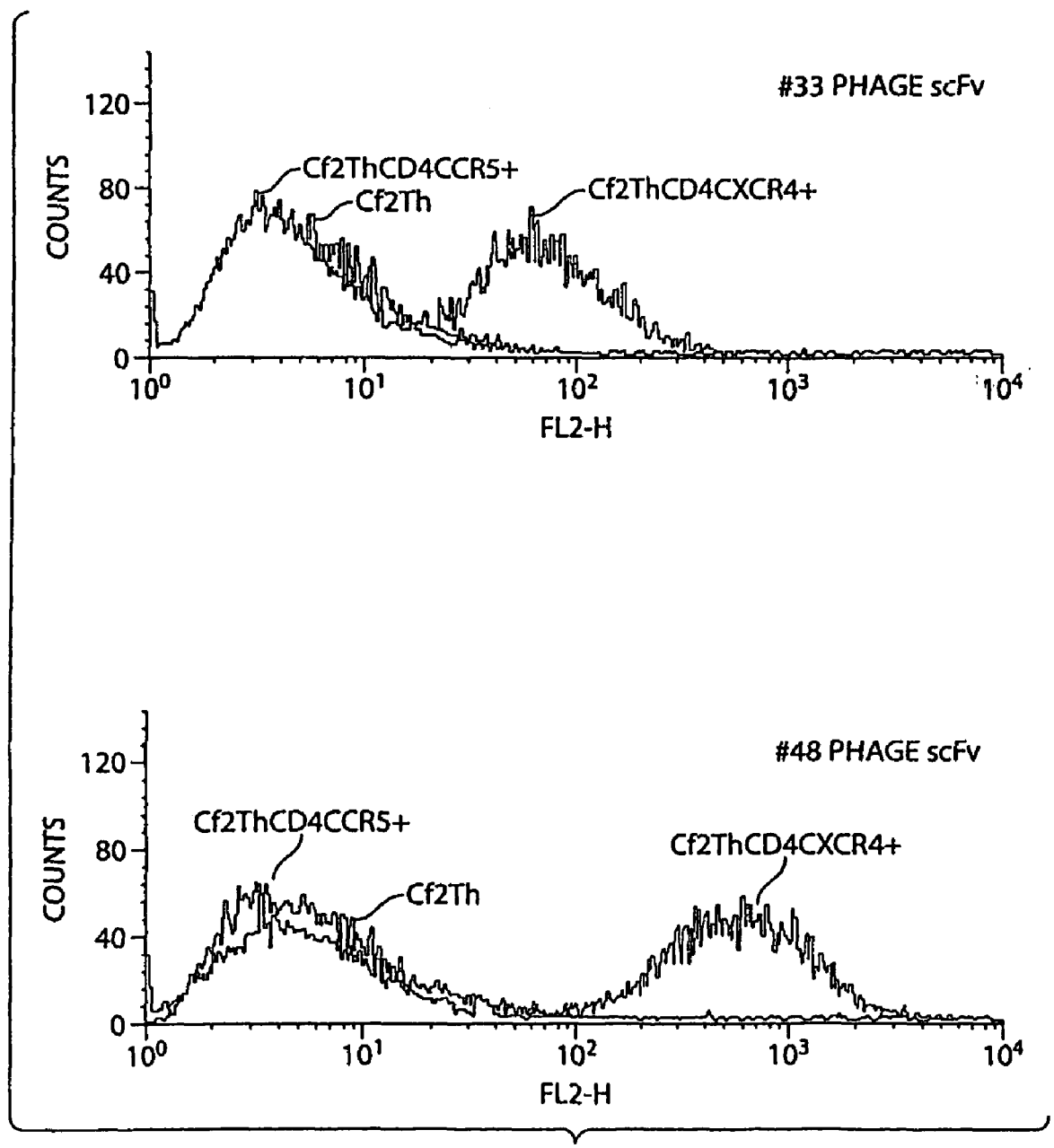
FIG. 5 is a series of FACS analysis graphs demonstrating that scFvs 33 and 48 bind to Cf2ThCD4$^+$CXCR4$^+$ cells but not to parental Cf2Th or Cf2ThCD4$^+$CCR5$^+$ cells.
Figure 6:
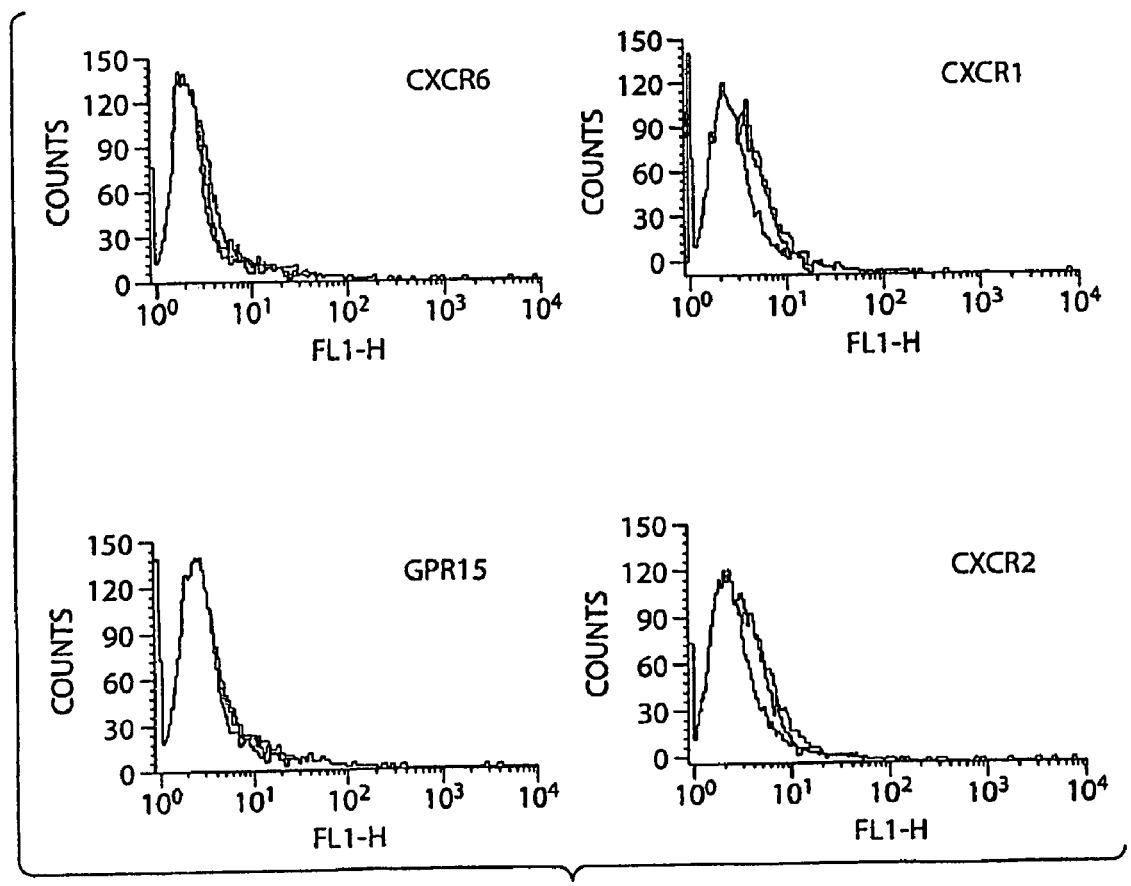
FIG. 6 is a series of FACS scan analysis graphs demonstrating that scFvs 33 and 48 do not cross react with other chemokine receptors such as CXCR6, CXCR1, GPR15, and CXCR2.
Figure 24:
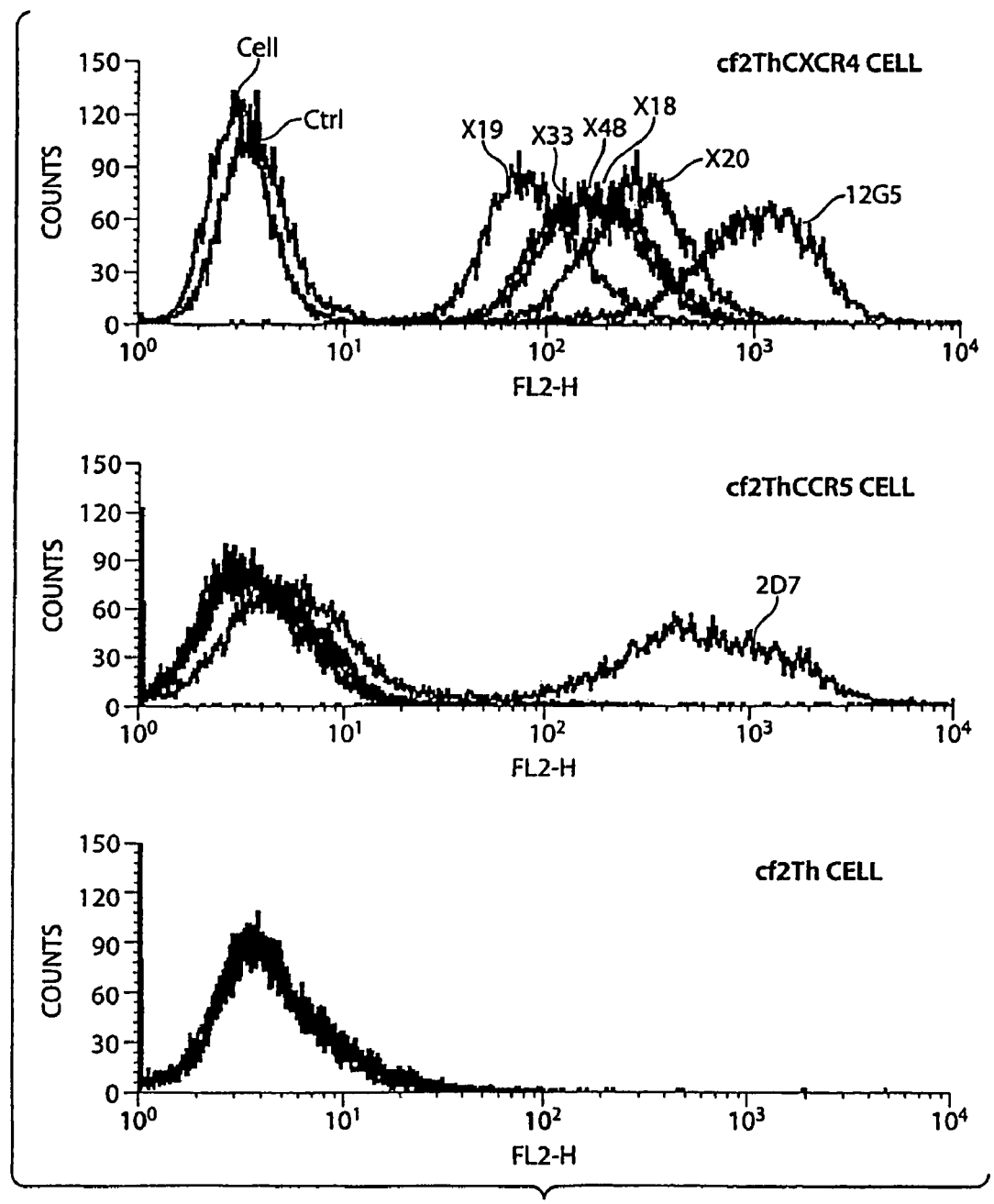
FIG. 24 is a series of FACS analysis graphs showing that X33, X48, X18, X19, and X20 specifically bind to CXCR4 cells.

As shown in FIGS. 4 and 5, two of the scFvs identified according to the methods disclosed herein (scFvs 33 and 48) are able to specifically bind to CXCR4, but do not bind to the related chemokine receptor CCR5. Similarly, FIG. 24 shows that clones X33, X48, X18, X19, and X20 specifically bind to CXCR4 cells. Likewise, the results presented in FIG. 6 demonstrate that scFvs 33 and 48 do not cross react with other chemokine receptors, including CXCR6, CXCR1, GPR15, and CXCR2.

Those skilled in the art will recognize that other scFvs that specifically bind to CXCR4 may also be identified according to the methods described herein.

Figure 25:
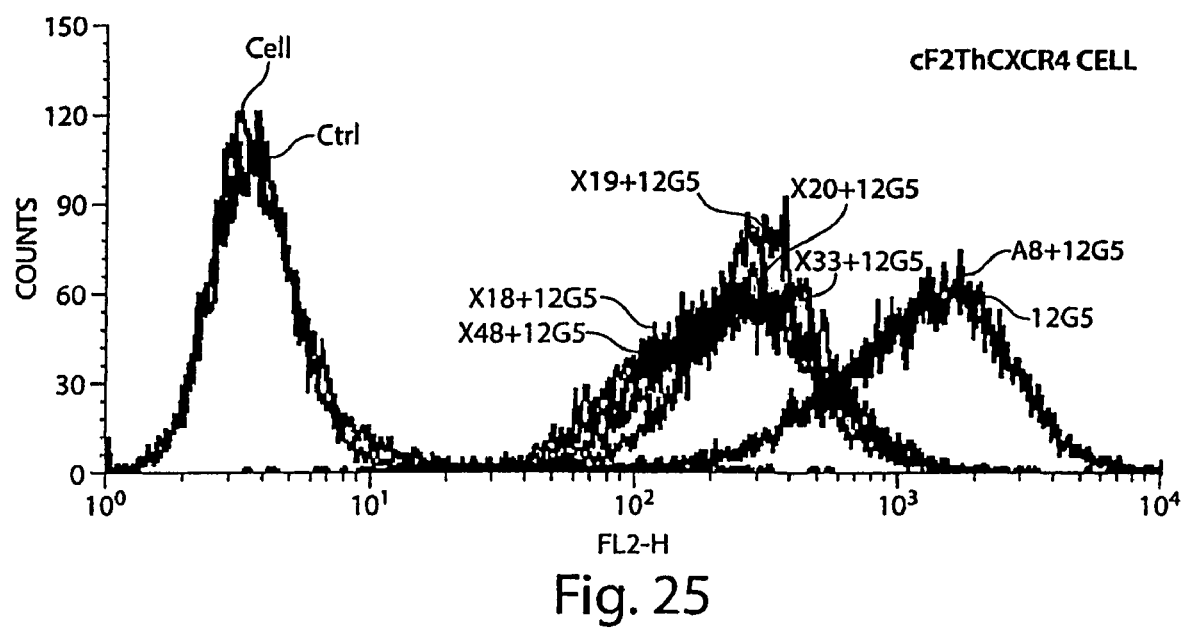
FIG. 25 is a FACS analysis graph demonstrating that X18, X19, and X20 (in addition to X33 and X48) compete with 12G5 for binding to CXCR4.
Figure 26A:
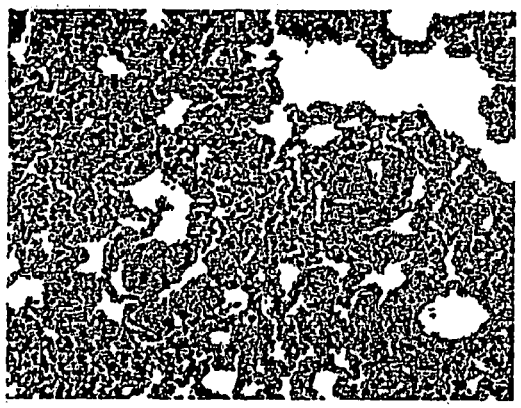
FIG. 26 is a series of photomicrographs showing the results of animals studies showing that the 48-Fc treated group (FIG. 26D) had less lung metastasis then the non-treated mice (FIGS. 26A, 26B, and 26C).
Figure 26B:
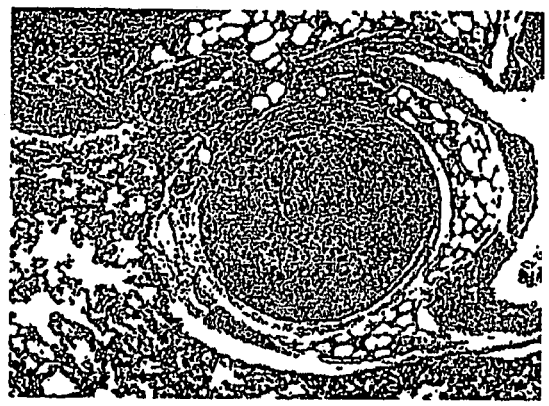
Figure 26C:
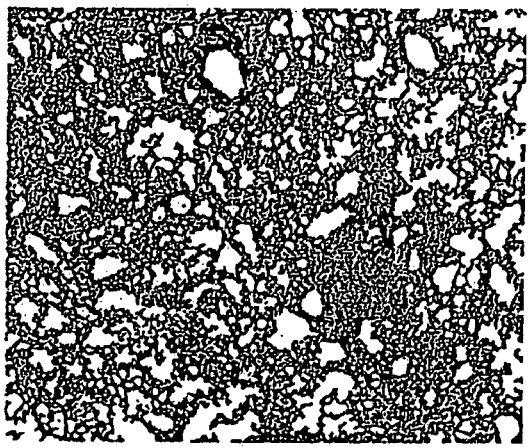
Figure 26D:
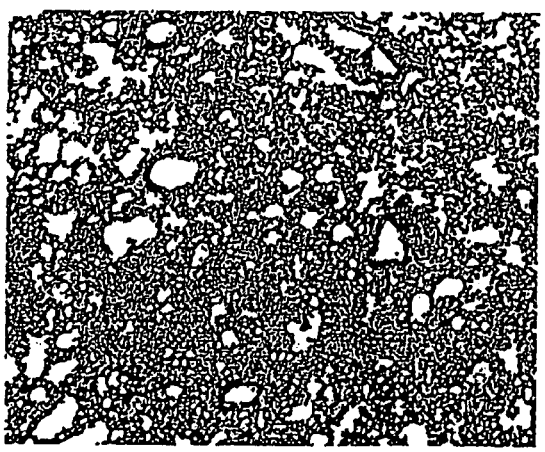
Figure 27:
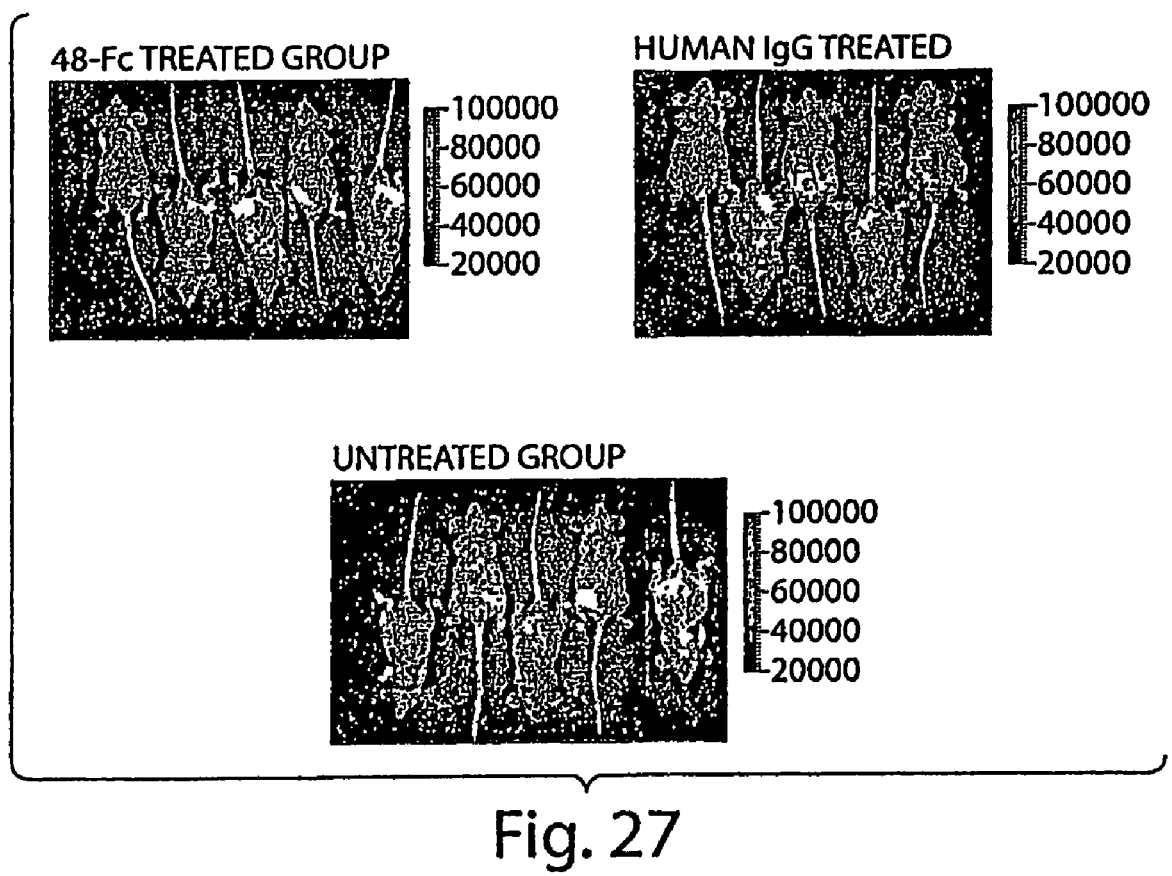
FIG. 27 is a series of photomicrographs showing that the 48-Fc treated group (FIG. 27A) has less lung metastasis than the non-treatment (FIG. 27C) and control-treated groups (FIG. 27B). The results for all three groups (five mice per group) tested are shown. The dots in each figure show the metastasis found in each mouse.

Moreover, scFv clones 33 and 48 compete with the neutralizing anti-CXCR4 monoclonal antibody 12G5 for binding to CXCR4. (See FIG. 7). FIG. 25 demonstrates that clones X18, X19, and X20 (in addition to X33 and X48) compete with 12G5 for binding to CXCR4.

As described in Example 3, infra, the scFvs of the invention were subsequently converted to scFv-Fc fusions (e.g., 18-Fc, 19-Fc, 20-Fc, 33-Fc, 48-Fc, 2N-Fc, 6R-Fc, etc.). Converting the scFvs to scFv-Fc fusion molecules increases the half life of the antibody. Alternatively (or in addition), the scFvs identified herein can also be converted into bivalent human whole IgG1 (e.g., mAb 18, mAb 19, mAb 20, mAb 33, mAb 48, mAb 2N, or mAb 6R, etc.), which also increases the half life of the antibody, as the half life of hIgG1 is approximately 21 days. Moreover, monoclonal antibodies prepared in this way include various effector functions attributable to the immunoglobulin, including, for example antibody-dependent cell-mediated cytotoxicity, which relies on the Fc portion of immunoglobulin. As described herein, the monoclonal antibodies as well as the scFv fusions of the invention are human antibodies having a high affinity to CXCR4.

Figure 8:
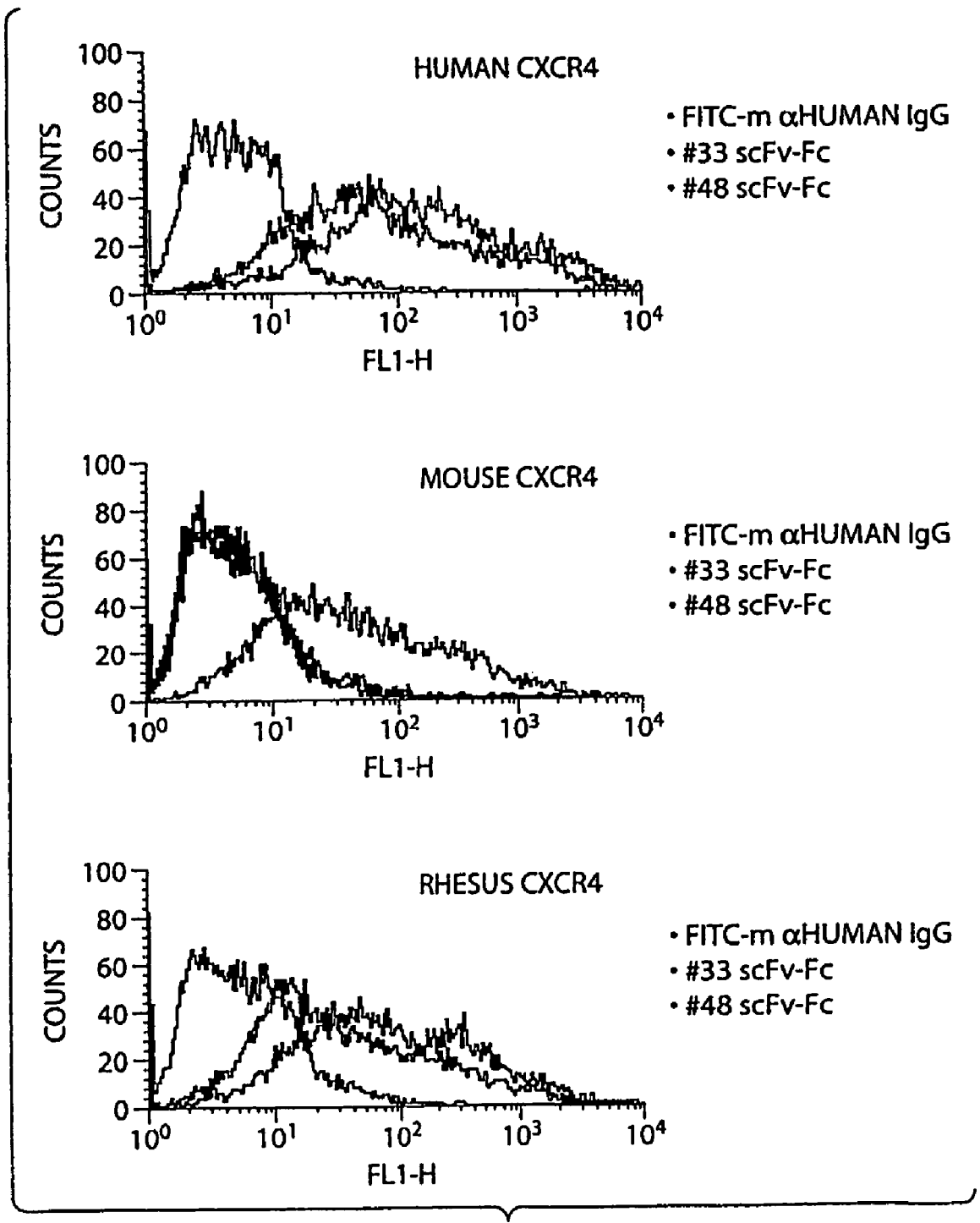
FIG. 8 shows the results of FACS analyses of the binding of 33 scFv-Fc and 48 scFv-Fc to 293T cells expressing human, mouse and rhesus macaque monkey CXCR4.
Figure 9A:
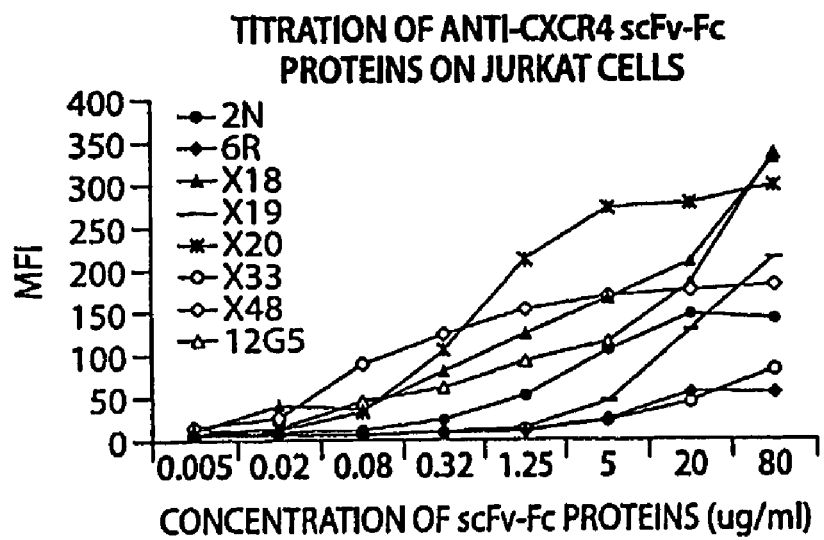
FIG. 9 is a series of graphs showing the titration of anti-CXCR4 scFv-Fc fusion proteins with the Jurkat (FIGS. 9A and 9C) and cF2ThCXCR4C9 (FIGS. 9B and 9D) cell lines. Anti-CXCR4 scFv-Fc fusion proteins or CXCR4 specific mAb 12G5 at the concentrations indicated on the X-axis were incubated with $5\times10^5$ cells for 50 min at 4° C. followed by treatment with anti-human Fc IgG-FITC for scFv-Fc fusion protein or anti-mouse Fc-FITC for 12G5 for an additional 40 minutes. Cells stained with the second antibody only were used as negative controls. Analysis was performed using flow cytometry, and MFI of total cells was used to measure the binding abilities of each clone. The EC50 values for both cell types are summarized in FIGS. 9E and 9F.
Figure 9B:
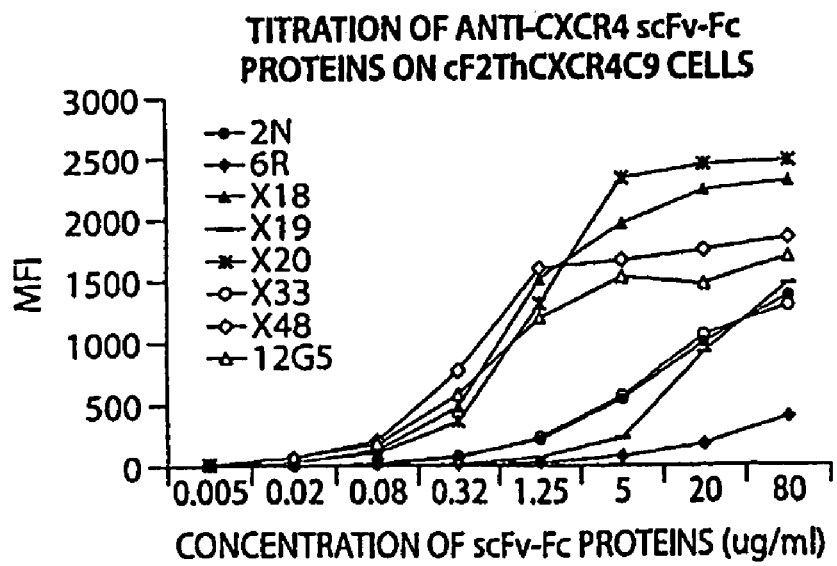

As shown in FIG. 8, scFv-Fc 48 was shown to cross react with mouse and rhesus macaque monkey CXCR4 receptors present on 293T cells. Moreover, scFv-Fc 33 was shown to cross react on rhesus macaque monkey (but not mouse) CXCR4 receptors present on 293T cells. As shown in Tables 2 and 3 infra, all seven clones are shown to bind to macaque monkey CXCR4 (Rh-4444) and mouse CXCR4 (Mu-4444). As shown, the binding of 6R AND X19 to monkey CXCR4 decreased by about 60% as compared to that to human CXCR4. However, the binding of the other clones did not change a lot. While none of the seven clones bind to mouse CXCR4 well, X48 and X18 are the two best binders. Amino acid differences present among the human, rhesus macaque, and mouse CXCR4 extracellular domains are shown in FIG. 20

In addition to binding CXCR4, the antibodies and antibody fragments of the invention are also able to block SDF-1 function.

As used herein, the terms monoclonal antibody X" and "mAb X" and "X mAb" and "X monoclonal antibody" are used interchangeably to refer to the bivalent full-length immunoglobulin prepared from a given scFv, where "X" refers to a particular clone number of the scFv identified according to the methods described herein (e.g., 18, 19, 20, 33, 48, 2N, or 6R).

Figure 1:
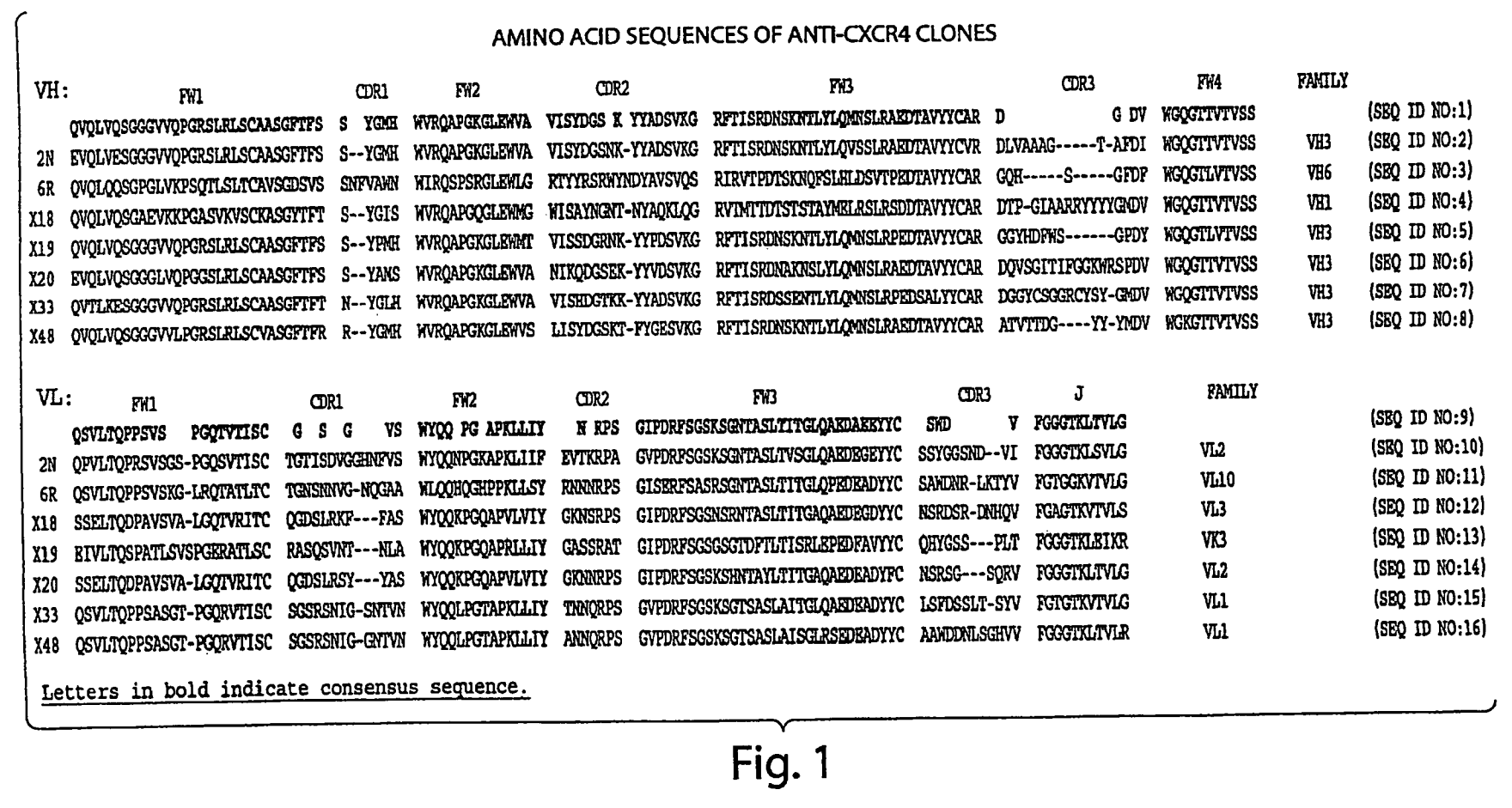

The amino acid sequences of the VH and VL regions of mAb 18, mAb 19, mAb 20, mAb 33, mAb 48, mAb 2N, and mAb 6R are provided in FIG. 1. FIG. 1 also provides a consensus sequence. In this consensus, when four or more clones have the same amino acid at a given position, that position in the consensus is designated by that amino acid.

The invention also encompasses single chain antibodies. For example, the invention encompasses scFvs 18, 19, 20, 33, 48, 2N, and 6R as well as any other scFvs identified according to the methods disclosed herein. As used herein, the term "scFv X" refers to a given single chain antibody identified according to the methods described herein, wherein "X" refers to a particular clone number (e.g., 18, 19, 20, 33, 48, 2N, or 6R).

In addition, the invention also provides diabodies formed by taking any of the scFvs of the invention and shortening the fifteen amino acid linker found between the $V_H$ and $V_L$ chains. (See Hollinger et al., Proc. Natl. Acad. Sci. USA 90:6444-6448 (1993)). This shortening causes "head-to-head" dimerization of the scFvs resulting in a bivalent molecule having an increasing binding affinity.

Also encompassed by the invention are any single chain-Fc fusions (e.g. 18-Fc, 19-Fc, 20-Fc, 33-Fc, 48-Fc, 2N-Fc, and 6R-Fc) and "minibodies" (e.g. 18-CH3, 19-CH3, 20-CH3, 33-CH3, 48-CH3, 2N—CH3, 6R—CH3) that specifically bind to the CXCR4 receptor. As used herein, the term "X-Fc" refers to a single chain antibody-Fc fusion prepared from a given scFv, wherein "X" refers to a particular clone number (e.g., 18, 19, 20, 33, 48, 2N, or 6R). Moreover, as used herein, the term "X—CH3" refers to a minibody prepared from a given scFv, wherein "X" refers to a particular clone number (e.g., 18, 19, 20, 33, 48, 2N, or 6R).

Saturation binding curves for all clones as well as murine monoclonal antibody 12G5 in both Jurkat cells and Cf2ThCXCR4 cells are shown in FIGS. 9A-D. By incubating these cells with varying concentration of scFv-Fc fusions and measuring the mean fluorescence at each concentration, the relative binding affinity of each scFv-Fc fusion can be determined. (See, Example 4, infra. See also FIG. 9E and FIG. 9F). The results shown in FIGS. 9A-F indicate that 48-Fc binds more strongly to CXCR4 than does 33-Fc. The EC50 values (e.g., 50% effective binding values) for each clone are shown in FIGS. 9E and 9F.

Those skilled in the art will recognize that additional scFvs, scFv-Fc fusions, and/or monoclonal antibodies having different binding affinities may also be therapeutically effective. For example, scFvs, scFv-Fc fusions, and/or monoclonal antibodies having binding affinities ranging from about $10^{-6}$ M to about $10^{-12}$ M may also be therapeutically effective. Thus, the present invention also encompasses scFvs, scFv-Fc fusions, and/or monoclonal antibodies that have the same apparent binding affinity as any of the scFvs, scFv-Fc fusions and/or monoclonal antibodies described herein. Such scFvs, scFv-Fc fusions, and/or monoclonal antibodies may compete with any of the scFvs, scFv-Fc fusions, and/or monoclonal antibodies described herein for binding to CXCR4.

Epitope Characterization

Epitope mapping experiments were performed to determine the binding sites for the anti-CXCR4 antibodies of the invention. (See Example 5. infra). Table 2 shows the results of epitope mapping of anti-CXCR4 mAbs with chimeric receptors composed of CXCR4 and CXCR2. 293T cells were transfected with CXCR4 and CXCR2 chimeric gene product, as well as macaque monkey CXCR4 or mice CXCR4 and then subsequently stained with anti-CXCR4 scFv-Fc fusion proteins followed by treatment with FITC-goat anti human IgG. Analysis was performed using a flow cytometer. Binding activity was measured by MFI on total cells gated. The following formula was used to calculate the reactivity:reactivity to each clone=(MFI of chimeric receptor/MFI of wild type CXCR4)×100%. The binding activities of each clone to wtCXCR4 are definitely 100%.

TABLE 2

Epitope Mapping of Anti-CXCR4 scFv-Fc Proteins (%)

| CXCR2/CXCR4 Chimeric Mutants | 2N | 6R | X18 | X19 | X20 | X33 | X48 |
|---|---|---|---|---|---|---|---|
| 4444 | 100 | 100 | 100 | 100 | 100 | 100 | 100 |
| 2222 | 4.7 | −0.3 | 2 | 7.5 | 4.1 | −0.52 | −0.2 |
| Δ-X4 | −1.6 | 16.6 | 48.1 | 11 | 9.6 | 3.1 | 5.3 |
| 2444b | 8.3 | 4.7 | 28.5 | 8.5 | 12.9 | 0.7 | 7.4 |
| 4442 | 61 | 1.4 | 35.2 | 5.3 | 27.9 | 15.5 | 41 |
| 2442 | 4.5 | 3.7 | 37.8 | 7.1 | 7.6 | 0.7 | 4.5 |
| 2242 | 1.2 | 1 | 10.1 | 5.2 | 11.6 | 0.3 | 3.5 |
| Rh-4444 | 98.3 | 41.9 | 89.1 | 35.1 | 77.5 | 102.6 | 93.6 |
| Mu-4444 | 3.6 | 4.5 | 13.1 | 5.6 | 6.6 | 2.1 | 14.8 |

Thus, the epitope mapping results presented in Table 2 demonstrate that antibodies 33 and 48 mainly recognized the N-terminal ("NT") region of CXCR4. The NT of CXCR4 was reported to be sufficient for efficient binding of SDF-1, the functional ligand of CXCR4, while signaling involved other extracellular loops ("ECLs") of CXCR4. (See Doranz et al., J. Virol. 7; 2752-61 (1999); Dragic, J. Gen Virol 82:1807-14 (2001)). Thus, anti-CXCR4 antibodies that can recognize other CXCR4 domains are desirable. To obtain such antibodies, NT truncations of CXCR4 (ΔNT-CXCR4) were presented on paramagnetic proteoliposomes ("PMPLs"), and these PMPLs were used to select the a human antibody library according to the methods of Example 2, infra.

Additional epitope mapping of 2N-Fc, 6R-Fc, 33-IgG1, 48-IgG1 Abs on CXCR4 was also done using FACS analysis with various of NT truncations of CXCR4 and CXCR2/CXCR4 chimeras. These results are shown in Table 3.

TABLE 3

FACS analysis on the binding of CXCR4 Abs to cells expressing CXCR4 and its variants (+%)

| CXCR4 variants expressed on 293T cell surface | Abs isolated by | | | | |
|---|---|---|---|---|---|
| | Wild-type CXCR4-PMPLs | | | ΔN25-CXCR4-PMPLs | Commercial mAb |
| | 33-IgG | 48-IgG | 2N-Fc | 6R-Fc | 12G5 |
| — | 0.0 | 0.0 | 0.0 | 0.0 | 0.0 |
| ΔN25 | 13.0 | 11.0 | −6.3 | 60.0 | 69.2 |
| ΔN31 | 9.0 | 4.0 | −7.0 | 12.8 | 55.4 |
| 2442* | 1.5 | −2.9 | −1.2 | −3.4 | 85.8 |
| 4442* | 99.5 | 91.9 | 89.1 | −0.4 | 102.9 |
| 2444b* (Entire NT deletion) | 1.0 | −2.3 | −6.2 | 2.2 | 70.1 |
| 4444* | 100.0 | 100.0 | 100.0 | 100.0 | 100.0 |

*2442, NT(aa1-27)and ECL3 of CXCR4 were replaced by CXCR2.
4442, ECL3 of CXCR4 was replaced by CXCR2.
2444b, NT(aa 1-38) of CXCR4 was replaced by CXCR2.
4444, wild-type CXCR4.

Based on this epitope mapping data, it was discovered that 33, 48, 2N recognize the NT of CXCR4 and that their binding to CXCR4 does not depend on the ECL3 of CXCR4. Clone 6R requires both NT (especially the NT25-38) and ECL3 of CXCR4 for binding, which indicated that 6R recognize an epitope formed by NT and ECL3 domains, thereby suggesting that clone 6R may have different function than 33, 48 and 2N.

Antibodies

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically binds" or "immunoreacts with" is meant that the antibody reacts with one or more antigenic determinants of the desired antigen and does not react with other polypeptides. Antibodies of the invention include, but are not limited to, polyclonal, monoclonal, chimeric, dAb (domain antibody), single chain antibodies, $F_{ab}$, $F_{ab'}$ and $F_{(ab')2}$ fragments, scFvs, diabodies, minibodies, scFv-Fc fusions, and $F_{ab}$ expression libraries. Unless specified to the contrary, any reference to "antibody" or "antibodies" made herein is meant to encompass any (or all) of these molecules.

A single chain Fv ("scFv") polypeptide molecule is a covalently linked $V_H$::$V_L$ heterodimer, which can be expressed from a gene fusion including $V_H$- and $V_L$-encoding genes linked by a peptide-encoding linker. (See Huston et al. (1988) Proc Nat Acad Sci USA 85(16):5879-5883). A number of methods have been described to discern chemical structures for converting the naturally aggregated, but chemically separated, light and heavy polypeptide chains from an antibody V region into an scFv molecule, which will fold into a three dimensional structure substantially similar to the structure of an antigen-binding site. See, e.g., U.S. Pat. Nos. 5,091, 513; 5,132,405; and 4,946,778.

Very large naïve human scFv libraries have been and can be created to offer a large source of rearranged antibody genes against a plethora of target molecules. For example, as described in Example 2, infra, two human non-immune scFv libraries having a total of $2.7 \times 10^{10}$ members have been constructed from B-cells of 57 un-immunized donors. Smaller libraries can be constructed from individuals with infectious diseases in order to isolate disease-specific antibodies. (See Barbas et al., Proc. Natl. Acad. Sci. USA 89:9339-43 (1992); Zebedee et al., Proc. Natl. Acad. Sci. USA 89:3175-79 (1992)).

In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "antigen-binding site," or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

As shown in FIG. 1, CDR1 of the VH region of the mAb 2N heavy chain has the sequence: SYGMH (SEQ ID NO:17); CDR2 of the VH region of the mAb 2N heavy chain has the sequence: VISYDGSNKYYADSVKG (SEQ ID NO:18); CDR3 of the VH region of the mAb 2N heavy chain has the sequence: DLVAAAGTAFDI (SEQ ID NO:19); CDR1 of the VL region of the mAb 2N light chain has the sequence TGTISDVGGHNFVS (SEQ ID NO:20); CDR2 of the VL region of the mAb 2N light chain has the sequence: EVTKRPA (SEQ ID NO:21); and CDR3 of the VL region of the mAb 2N light chain has the sequence: SSYGGSNDVI (SEQ ID NO:22).

Moreover, as shown in FIG. 1, CDR1 of the VII region of the mAb 6R heavy chain has the sequence: SNFVAWN (SEQ ID NO:23); CDR2 of the VH region of the mAb 6R heavy chain has the sequence: RTYYRSRWYNDYAVSVQS (SEQ ID NO:24); CDR3 of the VH region of the mAb 6R heavy chain has the sequence: GQHSGFDF (SEQ ID NO:25); CDR1 of the VL region of the mAb 6R light chain has the sequence TGNSNNVGNQGAA (SEQ ID NO:26); CDR2 of the VL region of the mAb 6R light chain has the sequence: RNNNRPS (SEQ ID NO:27); and CDR3 of the VL region of the mAb 6R light chain has the sequence: SAWDNRLKTYV (SEQ ID NO:28).

As also shown in FIG. 1, CDR1 of the VH region of the mAb 18 heavy chain has the sequence: SYGIS (SEQ ID NO:29); CDR2 of the VH region of the mAb 18 heavy chain has the sequence: WISAYNGNTNYAQKLQG (SEQ ID NO:30); CDR3 of the VH region of the mAb 18 heavy chain has the sequence: DTPGIAARRYYYYGMDV (SEQ ID NO:31); CDR1 of the VL region of the mAb 18 light chain has the sequence QGDSLRKFFAS (SEQ ID NO:32); CDR2 of the VL region of the mAb 18 light chain has the sequence: GKNSRPS (SEQ ID NO:33); and CDR3 of the VL region of the mAb 18 light chain has the sequence: NSRDSRDNHQV (SEQ ID NO:34).

Similarly, as shown in FIG. 1, CDR1 of the VH region of the mAb 19 heavy chain has the sequence: SYPMH (SEQ ID NO:35); CDR2 of the VH region of the mAb 19 heavy chain has the sequence: VISSDGRNKYYPDSVKG (SEQ ID NO:36); CDR3 of the VH region of the mAb 19 heavy chain has the sequence: GGYHDFWSGPDY (SEQ ID NO:37); CDR1 of the VL region of the mAb 19 light chain has the sequence RASQSVNTNLA (SEQ ID NO:38); CDR2 of the VL region of the mAb 19 light chain has the sequence: GASSRAT (SEQ ID NO:39); and CDR3 of the VL region of the mAb 19 light chain has the sequence: QHYGSSPLT (SEQ ID NO:40).

As shown in FIG. 1, CDR1 of the VH region of the mAb 20 heavy chain has the sequence: SYAMS (SEQ ID NO:41); CDR2 of the VH region of the mAb 20 heavy chain has the sequence: NIKQDGSEKYYVDSVKG (SEQ ID NO:42); CDR3 of the VH region of the mAb 20 heavy chain has the sequence: DQVSGITIFGGKWRSPDV (SEQ ID NO:43); CDR1 of the VL region of the mAb 20 light chain has the sequence QGDSLRSYYAS (SEQ ID NO:44); CDR2 of the VL region of the mAb 20 light chain has the sequence: GKNNRPS (SEQ ID NO:45); and CDR3 of the VL region of the mAb 20 light chain has the sequence: NSRSGSQRV (SEQ ID NO:46).

Moreover, CDR1 of the VII region of the mAb 33 heavy chain has the sequence: NYGLH (SEQ ID NO:47); CDR2 of the VH region of the mAb 33 heavy chain has the sequence: VISHDGTKKYYADSVKG (SEQ ID NO:48); CDR3 of the VH region of the mAb 33 heavy chain has the sequence: DGGYCSGGRCYSYGMDV (SEQ ID NO:49); CDR1 of the VL region of the mAb 33 light chain has the sequence SGSRSNIGSNTVN (SEQ ID NO:50); CDR2 of the VL region of the mAb 33 light chain has the sequence: TNNQRPS (SEQ ID NO:51); and CDR3 of the VL region of the mAb 33 light chain has the sequence: LSFDSSLTSYV (SEQ ID NO:52).

Likewise, as also shown in FIG. 1, CDR1 of the VII region of the mAb 48 heavy chain has the sequence: RYGMH (SEQ ID NO:53); CDR2 of the VII region of the mAb 48 heavy chain has the sequence: LISYDGSKTFYGESVKG (SEQ ID NO: 54); CDR3 of the VH region of the mAb 48 heavy chain has the sequence: ATVTTDGYYYMDV (SEQ ID NO: 55); CDR1 of the VL region of the mAb 48 light chain has the sequence SGSRSNIGGNTVN (SEQ ID NO:56); CDR2 of the VL region of the mAb 48 light chain has the sequence: ANNQRPS (SEQ ID NO: 57); and CDR3 of the VL region of the mAb 48 light chain has the sequence: AAWDDNLSGHVV (SEQ ID NO: 58).

As used herein, the term "epitope" includes any protein determinant capable of specific binding to an immunoglobulin, an scFv, an scFv-Fc fusion, a diabody, a minibody, and/or a T-cell receptor. Epitopic determinants usually consist of chemically active surface groupings of molecules such as amino acids or sugar side chains and usually have specific three-dimensional structural characteristics, as well as specific charge characteristics. For example, antibodies may be raised against N-terminal or C-terminal peptides of a polypeptide.

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present invention is said to specifically bind to a CXCR4 epitope when the equilibrium binding constant ($K_d$) is $\leq 1$ µM, preferably $\leq 100$ nM, more preferably $\leq 10$ nM, and most preferably $\leq 100$ pM to about 1 pM, as measured by assays such as radioligand binding assays or similar assays known to those skilled in the art.

CXCR4, or a derivative, fragment, analog, homolog or ortholog thereof, may be utilized as an immunogen in the generation of antibodies that immunospecifically bind these protein components.

Those skilled in the art will recognize that it is possible to determine, without undue experimentation, if an antibody has the same specificity as an antibody of the invention by ascertaining whether the former prevents the latter from binding to CXCR4. If the antibody being tested competes with the antibody of the invention, as shown by a decrease in binding by the antibody of the invention, then it is likely that the two antibodies bind to the same, or to a closely related, epitope.

Another way to determine whether an antibody has the specificity of an antibody of the invention is to pre-incubate the antibody of the invention with CXCR4, with which it is normally reactive, and then add the antibody being tested to determine if the antibody being tested is inhibited in its ability to bind CXCR4. If the antibody being tested is inhibited then, in all likelihood, it has the same, or functionally equivalent, epitopic specificity as the antibody of the invention. Screening of the antibodies of the invention, can be also carried out by utilizing CXCR4 and determining whether the test antibody is able to block the binding of SDF-1 to CXCR4.

Various procedures known within the art may be used for the production of polyclonal or monoclonal antibodies directed against a protein of the invention, or against derivatives, fragments, analogs homologs or orthologs thereof. (See, for example, Antibodies: A Laboratory Manual, Harlow E, and Lane D, 1988, Cold Spring Harbor Laboratory Press, Cold Spring Harbor, N.Y., incorporated herein by reference).

Antibodies can be purified by well-known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

The term "monoclonal antibody" or "mAb" or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. mAbs contain an antigen binding site capable of immunoreacting with a particular epitope of the antigen characterized by a unique binding affinity for it.

Monoclonal antibodies can be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human Mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies. (See Kozbor, J. Immunol., 133:3001 (1984); Brodeur et al., Monoclonal Antibody Production Techniques and Applications, Marcel Dekker, Inc., New York, (1987) pp. 51-63)).

The culture medium in which the hybridoma cells is cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980). Moreover, in therapeutic applications of monoclonal antibodies, it is important to identify antibodies having a high degree of specificity and a high binding affinity for the target antigen.

After the desired hybridoma cells are identified, the clones can be subcloned by limiting dilution procedures and grown by standard methods. (See Goding, *Monoclonal Antibodies: Principles and Practice*, Academic Press, (1986) pp. 59-103). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

Monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). Hybridoma cells serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (see U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Fully human antibodies are antibody molecules in which the entire sequence of both the light chain and the heavy chain, including the CDRs, arise from human genes. Such antibodies are termed "human antibodies", or "fully human antibodies" herein. Human monoclonal antibodies can be prepared by using trioma technique; the human B-cell hybridoma technique (see Kozbor, et al., 1983 Immunol Today 4: 72); and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

In addition, human antibodies can also be produced using additional techniques, including phage display libraries. (See Hoogenboom and Winter, J. Mol. Biol., 227:381 (1991); Marks et al., J. Mol. Biol., 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al., Bio/Technology 10, 779-783 (1992); Lonberg et al., Nature 368 856-859 (1994); Morrison, Nature 368, 812-13 (1994); Fishwild et al, Nature Biotechnology 14, 845-51 (1996); Neuberger, Nature Biotechnology 14, 826 (1996); and Lonberg and Huszar, Intern. Rev. Immunol. 13 65-93 (1995).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv (scFv) molecules.

An example of a method of producing a nonhuman host, exemplified as a mouse, lacking expression of an endogenous immunoglobulin heavy chain is disclosed in U.S. Pat. No. 5,939,598. It can be obtained by a method, which includes deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

One method for producing an antibody of interest, such as a human antibody, is disclosed in U.S. Pat. No. 5,916,771. This method includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen, and a correlative method for selecting an antibody that binds immunospecifically to the relevant epitope with high affinity, are disclosed in PCT publication WO 99/53049.

According to the invention, techniques can be adapted for the production of single-chain antibodies specific to an antigenic protein of the invention (see e.g., U.S. Pat. No. 4,946, 778). In addition, methods can be adapted for the construction of $F_{ab}$ expression libraries (see e.g., Huse, et al., 1989 Science 246: 1275-1281) to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

Bispecific antibodies are monoclonal, preferably human or humanized, antibodies that have binding specificities for at least two different antigens. In the present case, one of the binding specificities is for an antigenic protein of the invention. The second binding target is any other antigen, and advantageously is a cell-surfaceprotein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared using chemical linkage. Brennan et al., Science 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Additionally, Fab' fragments can be directly recovered from E. coli and chemically coupled to form bispecific antibodies. Shalaby et al., J. Exp. Med. 175:217-225 (1992) describe the production of a fully humanized bispecific antibody F(ab')$_2$ molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described.

For example, bispecific antibodies have been produced using leucine zippers. Kostelny et al., J. Immunol. 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers.

The "diabody" technology described by Hollinger et al., Proc. Natl. Acad. Sci. USA 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites.

Another strategy for making bispecific antibody fragments by the use of single-chain Fv (sFv) dimers has also been reported. See, Gruber et al., J. Immunol. 152:5368 (1994). Antibodies with more than two valencies are contemplated. For example, trispecific antibodies can be prepared. Tutt et al., J. Immunol. 147:60 (1991). Exemplary bispecific antibodies can bind to two different epitopes, at least one of which originates in the protein antigen of the invention. Alternatively, an anti-antigenic arm of an immunoglobulin molecule can be combined with an arm which binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Another bispecific antibody of interest binds the protein antigen described herein and further binds tissue factor (TF).

In addition, an antibody fragment called a 'minibody' can be engineered from an scFv. Such single chain variable fragments (scFv-CH3) will subsequently dimerize after formation, thereby producing an engineered, bivalent antibody fragment. Minibodies can be further modified to attach radioisotopes or other imaging agents without interfering with the ability of the minibodies to bind to target cells. Therefore, minibodies can be useful for diagnosis, staging, and therapeutic monitoring of diseases.

Any of the antibodies (or fragments thereof) of the invention can be expressed by a vector containing a DNA segment encoding the single chain antibody described above. These can include vectors, liposomes, naked DNA, adjuvant-assisted DNA, gene gun, catheters, etc. Vectors include chemical conjugates such as described in WO 93/64701, which has targeting moiety (e.g. a ligand to a cellular surface receptor), and a nucleic acid binding moiety (e.g. polylysine), viral vector (e.g. a DNA or RNA viral vector), fusion proteins such as described in PCT/US 95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses. DNA viral vectors are preferred. These vectors include pox vectors such as *orthopox* or avipox vectors, herpesvirus vectors such as a herpes simplex I virus (HSV) vector (see Geller, A. I. et al., J. Neurochem, 64:487 (1995); Lim, F., et al., in DNA Cloning: Mammalian Systems, D. Glover, Ed. (Oxford Univ. Press; Oxford England) (1995); Geller, A. I. et al., Proc Natl. Acad. Sci.: U.S.A. 90:7603 (1993); Geller, A. I., et al., Proc Natl. Acad. Sci. USA 87:1149 (1990), Adenovirus Vectors (see LeGal LaSalle et al., Science, 259:988 (1993); Davidson, et al., Nat. Genet. 3:219 (1993); Yang, et al., J. Virol. 69:2004 (1995) and Adeno-associated Virus Vectors (see Kaplitt, M. G. et al., Nat. Genet. 8:148 (1994).

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors are preferred for introducing the nucleic acid into neural cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g. infection, transfection, transduction or transformation. Examples of modes of gene transfer include e.g., naked DNA, $CaPO_4$ precipitation, DEAE dextran, electroporation, protoplast fusion, lipofection, cell microinjection, and viral vectors.

The vector can be employed to target essentially any desired target cell. For example, stereotaxic injection can be used to direct the vectors (e.g. adenovirus, HSV) to a desired location. Additionally, the particles can be delivered by intracerebroventricular (icv) infusion using a minipump infusion system, such as a SynchroMed Infusion System. A method based on bulk flow, termed convection, has also proven effective at delivering large molecules to extended areas of the brain and may be useful in delivering the vector to the target cell. (See Bobo et al., Proc. Natl. Acad. Sci. USA 91:2076-2080 (1994); Morrison et al., Am. J. Physiol. 266: 292-305 (1994)). Other methods that can be used include catheters, intravenous, parenteral, intraperitoneal and subcutaneous injection, and oral or other known routes of administration.

These vectors can be used to express large quantities of antibodies or antibody fragments that can be used in a variety of ways. For example, they can be used to detect the presence of CXCR4 in a sample. The antibody or antibody fragment can also be used to try to bind to and disrupt SDF-1 interaction with the CXCR4 receptor.

Heteroconjugate antibodies are also within the scope of the present invention. Heteroconjugate antibodies are composed of two covalently joined antibodies. Such antibodies have, for example, been proposed to target immune system cells to unwanted cells (see U.S. Pat. No. 4,676,980), and for treatment of HIV infection (see WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

It can be desirable to modify the antibody (or antibody fragment) of the invention with respect to effector function, so as to enhance, e.g., the effectiveness of the antibody (or antibody fragment). For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). (See Caron et al., J. Exp Med., 176: 1191-1195 (1992) and Shopes, J. Immunol., 148: 2918-2922 (1992)). Alternatively, an antibody can be engineered that has dual Fc regions and can thereby have enhanced complement lysis and ADCC capabilities. (See Stevenson et al., Anti-Cancer Drug Design, 3: 219-230 (1989)).

The invention also pertains to immunoconjugates comprising an antibody (or antibody fragment) conjugated to a cytotoxic agent such as a toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAPS), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}Bi$, $^{131}I$, $^{131}In$, $^{90}Y$, and $^{186}Re$.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaredehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Those of ordinary skill in the art will recognize that a large variety of possible moieties can be coupled to the resultant antibodies or to other molecules of the invention. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238:1098 (1987)). Preferred linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat #21651G); (iv) Sulfo-LC-SPDP (sulfosuccinimidyl 6 [3-(2-pyridyldithio)-propionamide] hexanoate (Pierce Chem. Co. Cat. #2165-G); and (v) sulfo-NHS (N-hydroxysulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem., 257: 286-288 (1982) via a disulfide-interchange reaction.

Use of Antibodies Against CXCR4

Methods for the screening of antibodies (or fragments thereof) that possess the desired specificity include, but are not limited to, enzyme linked immunosorbent assay (ELISA) and other immunologically mediated techniques known within the art.

Antibodies directed against CXCR4 (or any fragments thereof) may be used in methods known within the art relating to the localization and/or quantitation of CXCR4 (e.g., for use in measuring levels of CXCR4 within appropriate physiological samples, for use in diagnostic methods, for use in imaging the protein; and the like). In a given embodiment, antibodies specific to CXCR4, or a derivative, fragment, analog or homolog thereof, that contain the antibody-derived antigen-binding domain, are utilized as pharmacologically active compounds (referred to hereinafter as "Therapeutics").

An antibody of the invention specific for CXCR4 (or a fragment thereof) can be used to isolate a CXCR4 polypeptide by standard techniques, such as immunoaffinity, chromatography or immunoprecipitation. Antibodies directed against CXCR4 (or any fragments thereof) can be used diagnostically to monitor protein levels in tissue as part of a clinical testing procedure, e.g., to, for example, determine the efficacy of a given treatment regimen. Detection can be facilitated by coupling (i.e., physically linking) the antibody or antibody fragment to a detectable substance. Examples of detectable substances include, for example, various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibodies of the invention, including, for example, polyclonal, monoclonal, scFv, diabodies, minibodies, scFv-Fc fusions, humanized, and/or fully human antibodies, may be used as therapeutic agents. Such agents will generally be employed to treat or prevent a CXCR4-associated diseases or disorders or pathologies (e.g., HIV, cancer, or acute graft-versus-host disease) in a subject. An antibody preparation, preferably one having high specificity and high affinity for its target antigen, is administered to the subject and will generally have an effect due to its binding with the target. Administration of the antibody (or fragment thereof) may abrogate or inhibit or interfere with the binding of the target (e.g., CXCR4) with an endogenous ligand (e.g., SDF-1 or SDF-1α) to which it naturally binds. In this case, the antibody or antibody fragment binds to the target and masks a binding site of the naturally occurring ligand, thereby inhibiting binding of SDF-1 to CXCR4.

A therapeutically effective amount of an antibody of the invention (or a fragment thereof) relates generally to the amount needed to achieve a therapeutic objective. As noted above, this may be a binding interaction between the antibody (or antibody fragment) and its target antigen that, in certain cases, interferes with the functioning of the target. The amount required to be administered will furthermore depend on the binding affinity of the antibody for its specific antigen, and will also depend on the rate at which an administered antibody (or antibody fragment) is depleted from the free volume other subject to which it is administered. Common ranges for therapeutically effective dosing of an antibody or antibody fragment of the invention may be, by way of non-limiting example, from about 0.1 mg/kg body weight to about 50 mg/kg body weight. Common dosing frequencies may range, for example, from twice daily to once a week. Determination of the therapeutically effective amount of the antibody or fragment thereof is within the routine skill level of those in the art.

Antibodies specifically binding to CXCR4 or fragments thereof, as well as other molecules identified by the screening assays disclosed herein, can be administered for the treatment or prevention of CXCR4-related diseases or disorders (or diseases or disorders characterized by abnormal or irregular CXCR4 function) in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa., 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. (See, e.g., Marasco et al., Proc. Natl. Acad. Sci. USA, 90: 7889-7893 (1993)). The formulation can also contain more than one active compound as necessary for the particular indication being treated, preferably those with complementary activities that do not adversely affect each other. Alternatively, or in addition, the composition can also comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

An antibody according to the invention can be used as an agent for detecting the presence of CXCR4 (or a protein or a protein fragment thereof) in a sample. Preferably, the antibody contains a detectable label. Antibodies can be polyclonal, or more preferably, monoclonal. An intact antibody, or a fragment thereof (e.g., $F_{ab}$, scFv, scFv-Fc fusion, or $F_{(ab)2}$) can be used. The term "labeled", with regard to the probe or antibody, is intended to encompass direct labeling of the probe or antibody by coupling physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin.

The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitation, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody or antibody fragment can be labeled with a radioactive marker whose presence and location in a subject can be detected by standard imaging techniques.

Pharmaceutical Compositions

The antibodies or agents of the invention can be incorporated into compositions containing the monoclonal antibodies, scFv antibodies, scFv-Fc fusions, minibodies, and/or diabodies of the invention together with a carrier.

Moreover, the antibodies or agents of the invention (also referred to herein as "active compounds"), and derivatives, fragments, analogs and homologs thereof, can be incorporated into pharmaceutical compositions suitable for administration. Such compositions typically comprise the antibody or agent and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration. Also contemplated are kits containing the compositions of the invention in one or more containers.

Screening Methods

The invention provides methods (also referred to herein as "screening assays") for identifying modulators, i.e., candidate or test compounds or agents (e.g., peptides, peptidomimetics, small molecules or other drugs) that modulate or otherwise interfere with the binding of SDF-1 to the CXCR4 receptor. Also provided are methods of identifying compounds useful to treat or prevent CXCR4-related diseases or disorders. The invention also encompasses compounds identified using the screening assays described herein.

For example, the invention provides assays for screening candidate or test compounds, which modulate the interaction between SDF-1 and its receptor, CXCR4. The test compounds of the invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. (See, e.g. Lam, 1997. Anticancer Drug Design 12: 145).

A "small molecule" as used herein, is meant to refer to a composition that has a molecular weight of less than about 5 kD and most preferably less than about 4 kD. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

Examples of methods for the synthesis of molecular libraries can be found in the art, for example in: DeWitt, et al., 1993. Proc. Natl. Acad. Sci. U.S.A. 90: 6909; Erb, et al., 1994. Proc. Natl. Acad. Sci. U.S.A. 91: 11422; Zuckermann, et al., 1994. J. Med. Chem. 37: 2678; Cho, et al., 1993. Science 261: 1303; Carrell, et al., 1994. Angew. Chem. Int. Ed. Engl. 33: 2059; Carell, et al., 1994. Angew. Chem. Int. Ed. Engl. 33: 2061; and Gallop, et al., 1994. J. Med. Chem. 37: 1233.

Libraries of compounds may be presented in solution (see e.g., Houghten, 1992. Biotechniques 13: 412-421), or on beads (see Lam, 1991. Nature 354: 82-84), on chips (see Fodor, 1993. Nature 364: 555-556), in bacteria (see U.S. Pat. No. 5,223,409), in spores (see U.S. Pat. No. 5,233,409), in plasmids (see Cull, et al., 1992. Proc. Natl. Acad. Sci. USA 89: 1865-1869) or on phage (see Scott and Smith, 1990. Science 249: 386-390; Devlin, 1990. Science 249: 404-406; Cwirla, et al., 1990. Proc. Natl. Acad. Sci. U.S.A. 87: 6378-6382; Felici, 1991. J. Mol. Biol. 222: 301-310; and U.S. Pat. No. 5,233,409).

In one embodiment, a candidate compound is introduced to an antibody-antigen complex and determining whether the candidate compound disrupts the antibody-antigen complex, wherein a disruption of this complex indicates that the candidate compound modulates the interaction between SDF-1 and CXCR4. For example, the antibody may be any one of monoclonal antibody X, X-Fc, or scFv X, and the antigen may be CXCR4. As discussed above, 33, 48, and 2N recognize the N terminal region of CXCR4 and their ability to bind to CXCR4 does not depend on the ECL3 of CXCR4. In contrast, 6R requires both the N terminal region (especially NT25-38) and ECL3 for binding to CXCR4. Thus, it is possible that 6R may have a different function than 33, 48, and 2N.

Determining the ability of the test compound to interfere with or disrupt the antibody-antigen complex can be accomplished, for example, by coupling the test compound with a radioisotope or enzymatic label such that binding of the test compound to the antigen or biologically-active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemission or by scintillation counting. Alternatively, test compounds can be enzymatically-labeled with, for example, horseradish peroxidase, alkaline phosphatase, or luciferase, and the enzymatic label detected by determination of conversion of an appropriate substrate to product.

In one embodiment, the assay comprises contacting an antibody-antigen complex with a test compound, and determining the ability of the test compound to interact with the antigen or otherwise disrupt the existing antibody-antigen complex. In this embodiment, determining the ability of the test compound to interact with the antigen and/or disrupt the antibody-antigen complex comprises determining the ability of the test compound to preferentially bind to the antigen or a biologically-active portion thereof, as compared to the antibody.

In another embodiment, the assay comprises contacting an antibody-antigen complex with a test compound and determining the ability of the test compound to modulate the antibody-antigen complex. Determining the ability of the test compound to modulate the antibody-antigen complex can be accomplished, for example, by determining the ability of the antigen to bind to or interact with the antibody, in the presence of the test compound.

Those skilled in the art will recognize that, in any of the screening methods disclosed herein, the antibody may be a CXCR4-binding antibody, such as monoclonal antibody X or scFv X or X-Fc. Additionally, the antigen may be CXCR4, or a portion thereof. In any of the assays described herein, the ability of a candidate compound to interfere with the binding between monoclonal antibody X or scFv X or X-Fc and CXCR4 indicates that the candidate compound will be able to interfere with or modulate the binding of SDF-1 to the CXCR4 receptor.

The screening methods disclosed herein may be performed as a cell-based assay or as a cell-free assay. In the case of cell-free assays, it may be desirable to utilize a solubilizing agent such that the membrane-bound form of the proteins are maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether). N-dodecyl-N,N-dimethyl-3-ammonio-1-propane sulfonate, 3-(3-cholamidopropyl) dimethylamminiol-1-propane sulfonate (CHAPS), or 3-(3-cholamidopropyl)dimethylamminiol-2-hydroxy-1-propane sulfonate (CHAPSO).

In more than one embodiment, it may be desirable to immobilize either the antibody or the antigen to facilitate separation of complexed from uncomplexed forms of one or both following introduction of the candidate compound, as well as to accommodate automation of the assay. Observation of the antibody-antigen complex in the presence and absence of a candidate compound can be accomplished in any vessel suitable for containing the reactants. Examples of such vessels include microtiter plates, test tubes, and micro-centrifuge tubes. In one embodiment, a fusion protein can be provided that adds a domain that allows one or both of the proteins to be bound to a matrix. For example, GST-antibody fusion proteins or GST-antigen fusion proteins can be adsorbed onto glutathione sepharose beads (Sigma Chemical, St. Louis, Mo.) or glutathione derivatized microtiter plates, that are then combined with the test compound, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly. Alternatively, the complexes can be dissociated from the matrix, and the level of antibody-antigen complex formation can be determined using standard techniques.

Other techniques for immobilizing proteins on matrices can also be used in the screening assays of the invention. For example, either the antibody (e.g. monoclonal antibody X or scFv X or X-Fc) or the antigen (e.g. CXCR4) can be immobilized utilizing conjugation of biotin and streptavidin. Biotinylated antibody or antigen molecules can be prepared from biotin-NHS (N-hydroxy-succinimide) using techniques well-known within the art (e.g., biotinylation kit, Pierce Chemicals, Rockford, Ill.), and immobilized in the wells of streptavidin-coated 96 well plates (Pierce Chemical). Alternatively, other antibodies reactive with the antibody or antigen of interest, but which do not interfere with the formation of the antibody-antigen complex of interest, can be derivatized to the wells of the plate, and unbound antibody or antigen trapped in the wells by antibody conjugation. Methods for detecting such complexes, in addition to those described above for the GST-immobilized complexes, include immunodetection of complexes using such other antibodies reactive with the antibody or antigen.

The invention further pertains to novel agents identified by any of the aforementioned screening assays and uses thereof for treatments as described herein.

Diagnostic Assays

Antibodies of the present invention (or fragments thereof) can be detected by appropriate assays, e.g., conventional types of immunoassays. For example, a sandwich assay can be performed in which CXCR4 or a fragment thereof is affixed to a solid phase. Incubation is maintained for a sufficient period of time to allow the antibody in the sample to bind to the immobilized polypeptide on the solid phase. After this first incubation, the solid phase is separated from the sample. The solid phase is washed to remove unbound materials and interfering substances such as non-specific proteins which may also be present in the sample. The solid phase containing the antibody of interest (e.g. monoclonal antibody X or scFv-X or X-Fc) bound to the immobilized polypeptide is subsequently incubated with a second, labeled antibody or antibody bound to a coupling agent such as biotin or avidin. This second antibody may be another anti-CXCR4 antibody or another antibody. Labels for antibodies are well-known in the art and include radionuclides, enzymes (e.g. maleate dehydrogenase, horseradish peroxidase, glucose oxidase, catalase), fluors (fluorescein isothiocyanate, rhodamine, phycocyanin, fluorescarmine), biotin, and the like. The labeled antibodies are incubated with the solid and the label bound to the solid phase is measured. These and other immunoassays can be easily performed by those of ordinary skill in the art An exemplary method for detecting the presence or absence of CXCR4 in a biological sample involves obtaining a biological sample from a test subject and contacting the biological sample with a labeled monoclonal or scFv antibody or diabody according to the invention such that the presence of CXCR4 is detected in the biological sample.

As used herein, the term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. That is, the detection method of the invention can be used to detect CXCR4 in a biological sample in vitro as well as in vivo. For example, in vitro techniques for detection of CXCR4 include enzyme linked immunosorbent assays (ELISAs), Western blots, immunoprecipitations, and immunofluorescence. Furthermore, in vivo techniques for detection of CXCR4 include introducing into a subject a labeled anti-CXCR4 antibody. For example, the antibody can be labeled with a radioactive marker whose presence and location in a subject can be detected by standard imaging techniques.

In one embodiment, the biological sample contains protein molecules from the test subject. One preferred biological sample is a peripheral blood leukocyte sample isolated by conventional means from a subject.

The invention also encompasses kits for detecting the presence of CXCR4 in a biological sample. For example, the kit can comprise in one or more containers: a labeled compound or agent capable of detecting CXCR4 (e.g., an anti-CXCR4 scFv antibody, monoclonal antibody, scFv-Fc fusion, minibody, and/or diabody) in a biological sample; means for determining the amount of CXCR4 in the sample; and means for comparing the amount of CXCR4 in the sample with a standard. The compound or agent can be packaged in a suitable container. The kit can further comprise instructions for using the kit to detect CXCR4 in a sample.

Methods of Treatment

The invention provides for both prophylactic and therapeutic methods of treating a subject at risk of developing (or susceptible to) a CXCR4-related disease or disorder. Such diseases or disorders include, but are not limited to, e.g., cancer, HIV, and acute graft-versus-host disease. The appropriate agent(s) to be used in the prophylactic and therapeutic methods of the invention can be determined based on screening assays described herein. Alternatively (or in addition) the agent to be administered is any scFv or a monoclonal antibody or a diabody that binds CXCR4 that has been identified according to the methods of the invention.

Prophylactic Methods

In one aspect, the invention provides methods for preventing a CXCR4-related disease or disorder or a disease or disorder associated with abnormal or irregular CXCR4 function in a subject by administering to the subject a monoclonal antibody, scFv-Fc fusion, or scFv antibody of the invention or an agent identified according to the methods of the invention. For example, scFv X and/or monoclonal antibody X and/or X-Fc may be administered in therapeutically effective amounts.

Prevention of T-tropic X4 HIV-1 Infection

HIV and related viruses require co-receptors, in addition to CD4, in order to infect target cells. HIV-1 is able to use either CXCR4 or CXCR5 as a co-receptor (where CD4 is the main receptor) to facilitate binding and entry into T cells. Those skilled in the art will recognize that the chemokine receptor CXCR4 is the main co-receptor used by T-tropic X4 HIV-1 strains to infect its target T cells. (See Feng et al., Science 272:872-77 (1996); Berson et al., J. Virol 70:6288-95 (1996)). CXCR4 is also required for the infection by dual-tropic strains of HIV-1 and mediates CD-4 independent infection by HIV-2. (See Doranz et al., Cell 85:1149-58 (1996); Endres et al., Cell 87:745-56 (1996)). In addition, the binding of the CXCR4 ligand, SDF-1, to CXCR4 has been shown to prevent infection by T-tropic HIV-1. (See Bleul et al., Nature 382:829-33 (1996); Oberlin et al., Nature 382:833-35 (1996)).

Subjects at risk for CXCR4-related diseases or disorders such as HIV include patients who have been exposed to HIV in some way. Administration of a prophylactic agent can occur prior to the manifestation of symptoms characteristic of the CXCR4-related disease or disorder, such that a disease or disorder is prevented or, alternatively, is delayed in its progression.

Figure 10:
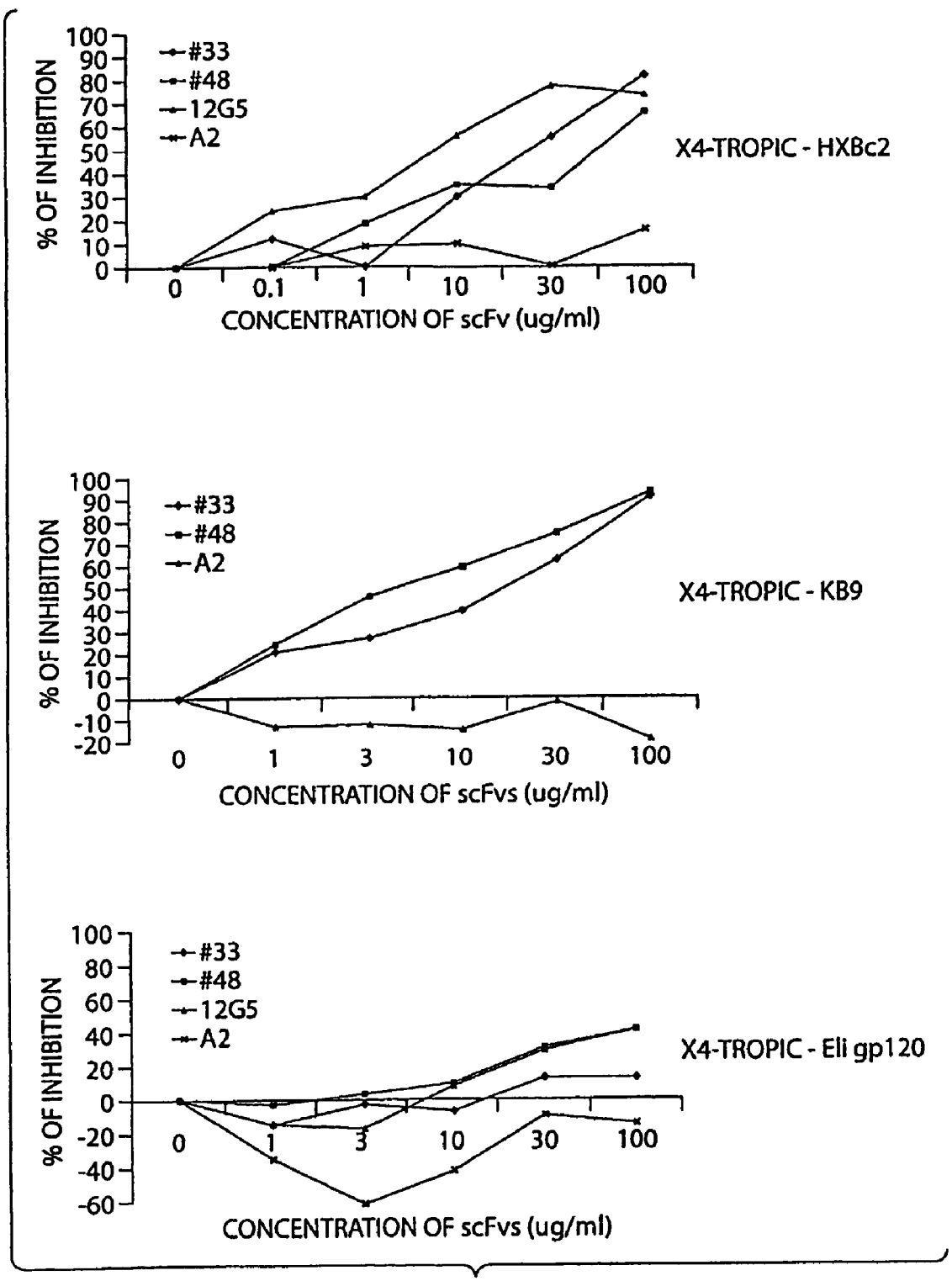
FIG. 10 is a series of graphs demonstrating the inhibition of HIV-1 reporter virus entry into Cf2ThCD4CXCR4 cells.
Figure 11A:
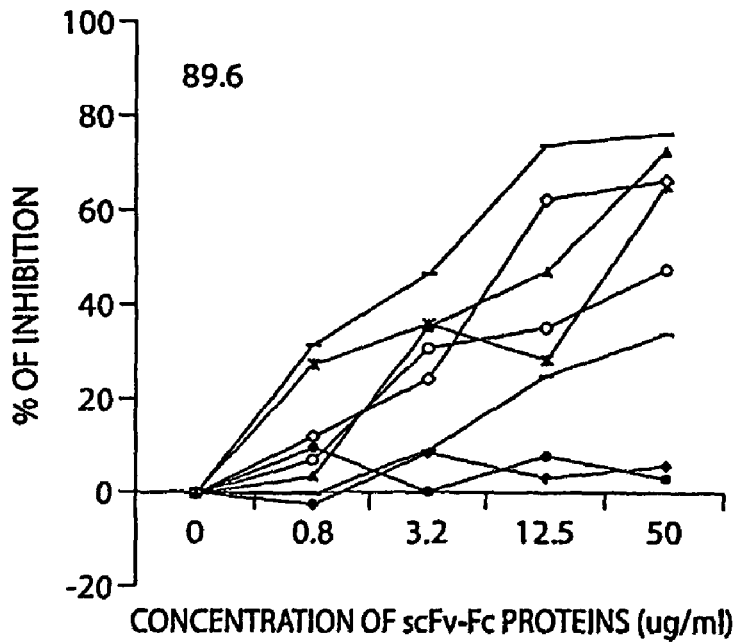
FIG. 11 is a series of graphs demonstrating the ability of scFv fusion proteins to block the entry of single-round pseudo type HIV-1 into target cells. 6000 cf2ThCD4CXCR4 cells were seeded in each well of an Opaque/Black Tissue Culture Plate. The following day, cells were treated with 50 ul DMEM medium with or without CXCR4 specific scFv-Fc proteins or control antibodies at the concentration indicated followed by infection with single round luciferase reporter pseudo type viruses for another 2 hrs. Luciferase activities (cpm) were measured 48 hrs later. The average of triplicate wells was used to calculate the inhibition ability: (average cpm of experimental wells/average cpm of wells without treatment with antibody before adding virus)×100%. X4 tropic HIV-1 pseudo viruses Hxbc-2 (FIG. 11C), KB-9 (FIG. 11B) and dual tropic 89.6 (FIG. 11A) were tested in this experiment.
Figure 11B:
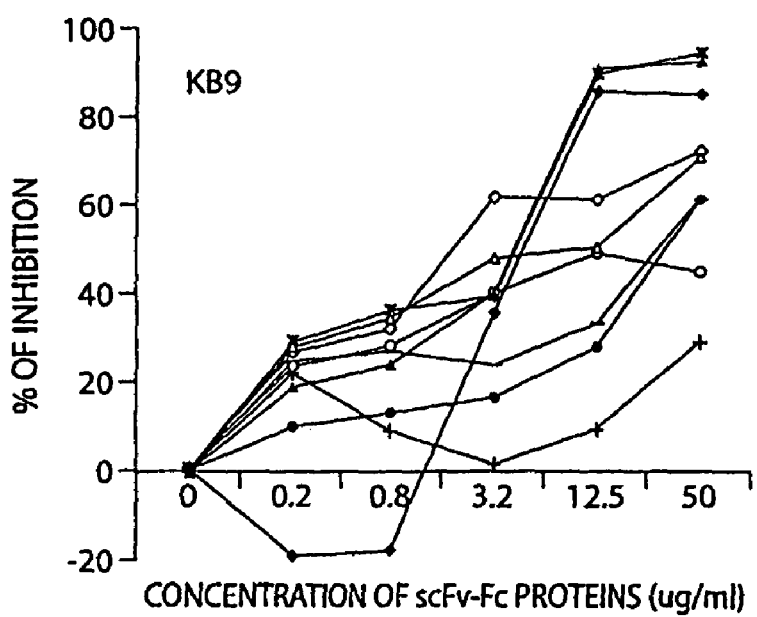
Figure 11C:
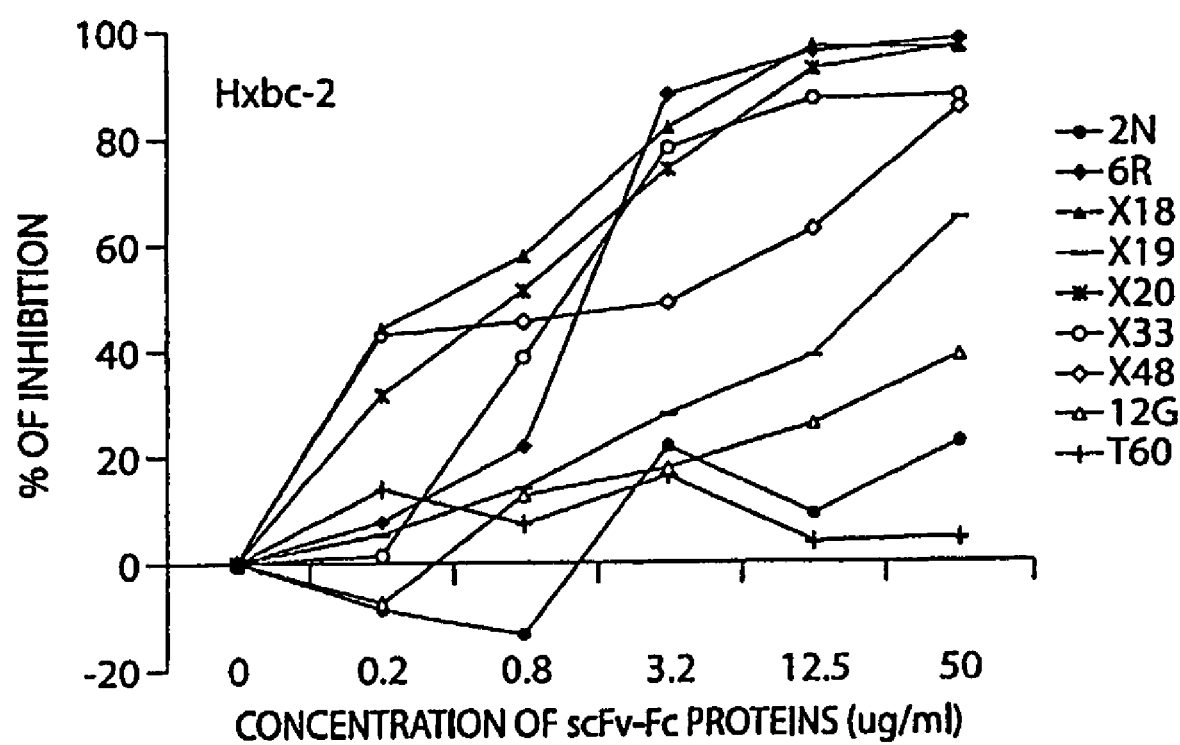
Figure 12:
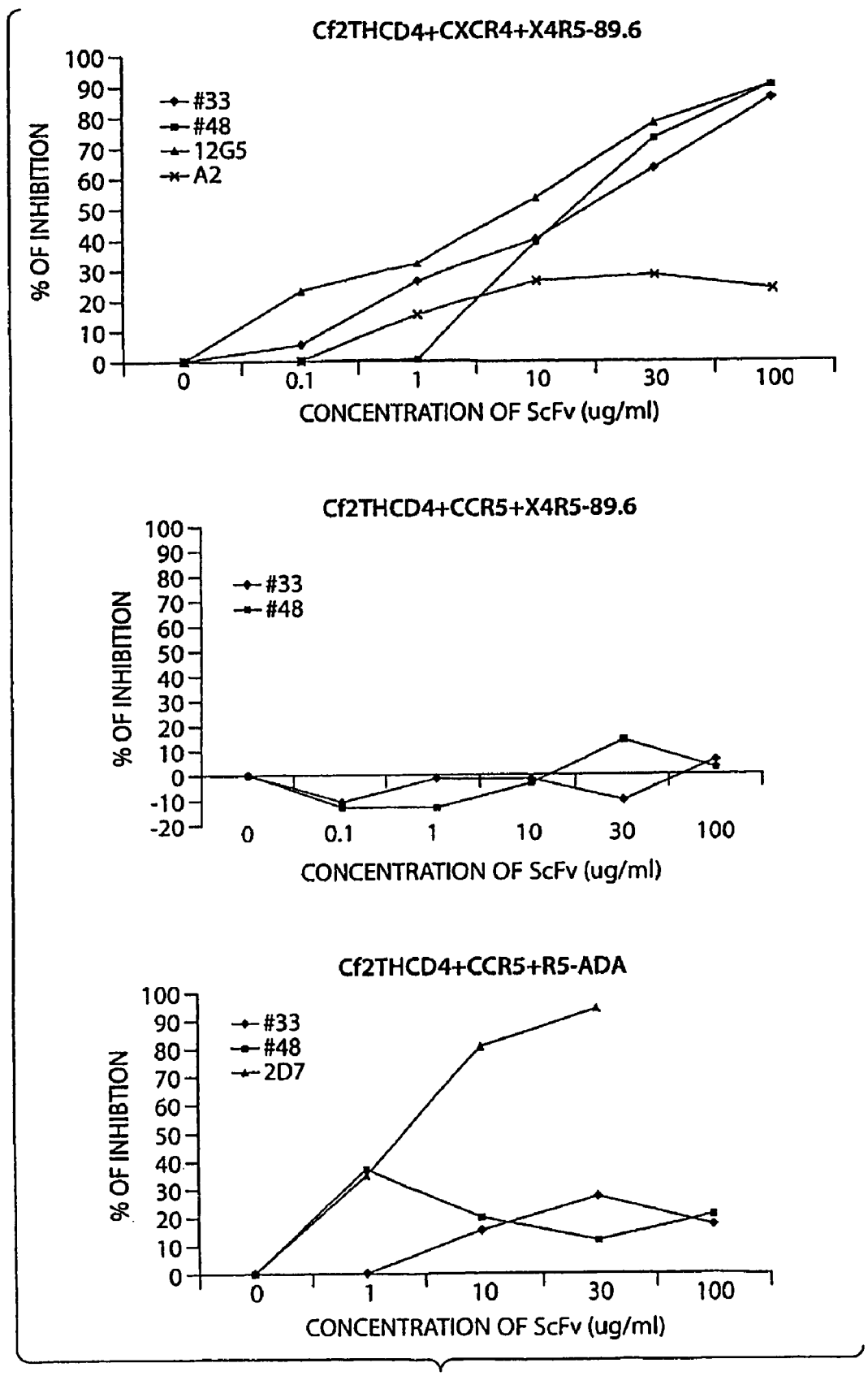
FIG. 12 is a series of graphs demonstrating the inhibition of HIV-1 reporter virus entry by scFvs 33 and 48.

Antibodies to CXCR4 have been shown to block HIV-1 and HIV-2 fusion and infection of human target cells. (See Feng et al., Science 272:872-77 (1996); Endres et al., Cell 87:745-56 (1996); and Brelot et al., J. Virol., 71:4744-51 (1997)). As shown in FIGS. 10 and 11A-C, the scFv fusion proteins of the invention are able to inhibit HIV-1 reporter virus entry into Cf2ThCD4CXCR4 cells. Moreover, FIG. 11A-C shows that all scFv-Fc fusions (with the exception of 2N-Fc) are able to inhibit HIV-1 reporter virus entry to different extents Likewise, the inhibition of scFv 33 and scFv 48 is specific to those cells expressing the CXCR4 receptor. (See FIG. 12). Thus, these results indicate that any of the antibodies of the invention can be used to prevent X4-tropic HIV-1 infection. Specifically, monoclonal antibody X (and/or scFv X) can be administered in a therapeutically or prophylactically effective amount to a patient susceptible to X4-tropic HIV-1 infection in order to prevent infection.

CXCR4 antagonists have been shown to have anti-HIV-1 activity. For example, AMD3100, a highly specific CXCR4 antagonist consistently blocks X4 viral replication in all target cell types. (See Schols et al., Curr Top Med Chem 4(9): 883-93 (2004)). AMD3100 has been shown to dose-dependently inhibit X4 viruses after 10 days of continuous infusion. Another CXCR4 antagonist, AMD070, is another candidate HIV drug. Other CXCR4 antagonists known in the art that have been shown to have anti-HIV activity include, but are not limited to peptidic compounds (e.g., T22 (an 18-mer), T134 (a 14-mer), ALX40-4C (a 9-mer), and CGP 64222 (a 9-mer), HIV-1 Tat protein, and bicyclam derivatives. (See, Schols, Curr Top Med. Chem. 4(9):883-93 (2004)). Thus, those skilled in the art will recognize that any of the antibodies or antibody fragments disclosed herein can be used alone or in conjunction with one or more known CXCR4 antagonist to inhibit HIV viral replication.

Prevention of CXCR4-Associated Diseases and Disorders

In addition, the antibodies of the invention can also be used for the prevention of a disease or disorder associated with CXCR4 function or expression by administering a therapeutically effective amount of the antibodies or antibody fragments of the invention (alone or in combination) to a person at risk of suffering from said disease or disorder. For example, the disease or disorder to be prevented may be characterized by abnormal or irregular CXCR4 expression or function. For example, the disease or disorder may be X4-tropic HIV infection, cancer (including, for example, breast cancer, renal cell carcinoma, non-small cell lung cancer, prostate cancer, glioblastoma, and/or any hypoxic tumor (e.g., any solid tumor)), and acute graft-versus-host disease.

Therapeutic Methods

Another aspect of the invention pertains to methods of treating CXCR4-related diseases or disorders in a patient. In one embodiment, the method involves administering an agent (e.g., an agent identified by a screening assay described herein alone or in combination with an scFv antibody, monoclonal antibody, scFv-Fc fusion, minibody, or diabody identified according to the methods of the invention), or combination of agents that bind to CXCR4 to a patient suffering from the disease or disorder.

Cancer Metastasis

There are at least three major theories to explain the basis of cancer metastasis toward certain tumors. (See Liotta, Nature 410:24 (2001)). First, it is possible that tumor cells leave the blood and lymphatic systems to the same extent at all organs but multiply only in those organs having the appropriate growth factors. Second, it is possible that the endothelial cells that line the blood vessels in target organs express adhesion molecules, which cause circulating tumor cells to stop in those organs. Third, it is possible that organ-specific attractant molecules enter the circulation, thereby stimulating the migrating tumor cells to invade the walls of blood vessels and enter the organs. Under such a "chemo-attraction" theory, organ-specific metastasis is governed, in part, by interactions between chemokine receptors on cancer cells and matching chemokines in target organs. (See Staller et al., Nature 425: 307-11 (2003)).

For example, malignant breast cancer cells express CXCR4 and commonly metastasize to organs that are an abundant source of SDF-1α. (See Muller et al., Nature 410: 50-56 (2001)). Thus, CXCR4 has been shown to play an important role in the targeted metastasis of breast cancer to the lungs, bones, and/or liver. Specifically, malignant breast cancer cells, which express CXCR4, invade the extracellular matrix and circulate in the blood and lymphatic vessels. (See Li et al., Cancer Cell 6:459-69 (2004)). The attraction between SDF-1α and CXCR4 causes breast cancer cells to leave the circulation and migrate into organs expressing large amounts of chemokines, where they proliferate, induce angiogenesis, and form metastatic tumor. (See id.). CXCR4 has also been shown to be involved in the metastasis of prostate cancer to bone marrow (see Taichman et al., Cancer Res. 62:1832-37 (2002)) and colon cancer to the liver (see Zeelenberg et al., Cancer Res. 63:3833-39 (2003)). Thus, agents that block the binding of SDF-1 or SDF-1α to CXCR4 may be able to prevent cancer metastasis.

Bachelder et al. have shown that VEGF is a requisite autocrine factor for breast carcinoma invasion (but not survival) in vitro. (See Bachelder et al., Cancer Research 62:7203-06 (2002)). Moreover, VEGF regulates the expression of CXCR4. This VEGF target is needed for invasion but not for cell survival. Likewise, CXCR4 mediates migration of breast carcinoma cells towards SDF-1. This migration is dependent on autocrine VEGF. CXCR4 inhibitory peptides have been shown to suppress this invasion. Therefore, as demonstrated by Bachelder et al., a VEGF autocrine pathway induces chemokine receptor expression in breast cancer cells, thereby promoting their directed migration toward specific chemokines.

Similarly, Hong et al., Cancer Letters xx:1-7 (2005), have shown that SDF-1 and CXCR4 are up-regulated by VEGF and contribute to glioma cell invasion. Specifically, Hong et al. demonstrated that VEGF not only stimulates angiogenic cells but also has a direct effect on glioma cell proliferation and invasion, possibly by increasing SDF-1 and CXCR4 levels.

The CXCR4 antagonist, CTCE-9908 (Chemokine Therapeutics, Vancouver) has been shown to reduce cancer metastasis by 50-70% and to have anti-angiogenic properties. CTCE-9908 is designed to block the receptor (CXCR4) that has been identified as critical in the process of tumor metastasis to other tissues in the body. The CXCR4 receptor is present on most human tumors cells, including lung, breast, prostate, colon, ovarian, bone, brain, and skin cancer. Those skilled in the art will recognize that a high level of CXCR4 expression in cancer cells is correlated to tumor progression, high metastasis rate and low patient survival rate.

Therefore, those skilled in the art will recognize that any of the antibodies or antibody fragments of the invention can be used to treat or prevent cancer metastasis by administering a therapeutically effective amount of the antibody (alone or in combination with one or more CXCR4 antagonists) to a patient suffering from a cancer involving tumor cells that express CXCR4. For example, those skilled in the art will recognize that the cancer may be, e.g., breast cancer, renal cell carcinoma, non-small cell lung cancer, prostate cancer, colon cancer, ovarian cancer, bone cancer, brain cancer, skin cancer, and/or glioblastoma. Determination of the effective amount of the antibody or fragments thereof to be administered is within the routine skill of those in the art.

In addition, it has also been demonstrated that tumor cells adapt to hypoxia by increasing their synthesis of hypoxia-inducible factor (HIF), which in turn, binds to and activates several genes. Specifically, Staller et al. have shown that the von Hippel-Lindau tumor suppressor protein (pVHL) negatively regulates CXCR4 expression by virtue of its ability to target the α-subunits of HIF (HIF-α) for degradation under normoxic conditions. (See Staller et al., Nature 425:307-11 (2003), incorporated herein by reference; Bernards, Nature 425:247-48 (2003), incorporated herein by reference). Under hypoxic conditions, this degradation process is suppressed, thereby resulting in HIF-dependent CXCR4 activation. (See Staller et al., Nature 425:307-11 (2003)). Therefore, it is possible that CXCR4 might be needed to promote the survival of tumor cells in hypoxic environments. (See Bernards, Nature 425:247-48 (2003); Zeelenberg et al., Cancer Res. 63:3833-39 (2003)). Moreover, by enhancing cell motility, CXCR4 may allow tumor cells to migrate away from areas of low oxygen towards specific organs. (See Bernards, Nature 425:247-48 (2003)).

Similarly, Phillips et al., have shown that activation of the EGF receptor ("EGFR") by EGF increases CXCR4 expression and the migratory capacity of non-small cell lung cancer ("NSCLC"). (See J. Biol. Chem. 280(23):22473-481 (2005)). Moreover, when NSCLC cells were cultured with EGF under hypoxic conditions, CXCR4 expression was dramatically enhanced. Thus, Phillips et al. hypothesizes that a combination of low oxygen tension and overexpression of EGFR within a primary tumor of NSCLC may provide the microenvironmental signals necessary to upregulate CXCR4 expression and promote metastasis.

In addition, the results presented by Staller et al. and Phillips et al. indicate that a high level of CXCR4 expression is a predictor of poor tumor-specific survival, which, in turn, suggests that monitoring CXCR4 expression in patients suffering from any solid tumor (including, but not limited to, renal cell carcinomas) may provide additional prognostic information. (See Staller et al., Nature 425:307-11 (2003)). Thus, those skilled in the art will recognize that any of the antibodies (or antibody fragments) disclosed herein can be used in order to monitor CXCR4 expression in such patients.

Moreover, those skilled in the art will also recognize that agents that block or neutralize the increased CXCR4 activity resulting from HIF induction in hypoxic tumors (e.g., any solid tumor) may be able to prevent cancer metastasis. For example, any of the antibodies or antibody fragments of the invention can be used to treat or prevent cancer metastasis by administering a therapeutically effective amount of the antibody to a patient suffering from a solid tumor characterized by HIF-dependent CXCR4 activation. Those skilled in the art will recognize that the solid tumor may be, for example, breast cancer, renal cell carcinoma, non-small cell lung cancer, prostate cancer, glioblastoma, and/or any other tumor that becomes hypoxic. Determination of the effective amount of the antibody is within the routine skill of those in the art.

In addition, any of the antibodies (or antibody fragments) of the invention can also be used in conjunction with one or more additional anti-metastatic agents (e.g., EGFR family antagonists) in order to treat or prevent cancer metastasis in patients suffering from a cancer involving tumor cells that express CXCR4.

For example, amplification of the human epidermal growth factor receptor 2 (HER2) gene results in overexpression of the HER2 protein, a condition that occurs in approximately 25% of all breast cancer patients. (See Slamon et al., Science 244:707-12 (1989)). HER2 enhances cancer invasion and lung metastasis. (See Tan et al., Cancer Res. 57:1199-205 (1997); Yarden et al., Mol. Cell. Biol. 2:127-37 (2001); and Yu et al., Oncogene 19:6115-21 (2000)). Moreover, HER2 may also be overexpressed in other cancers such as ovarian cancer, osteosarcoma, lung cancer, pancreatic cancer, salivary gland cancer, colon cancer, prostate cancer, endometrial cancer, and bladder cancer.

Figure 13:
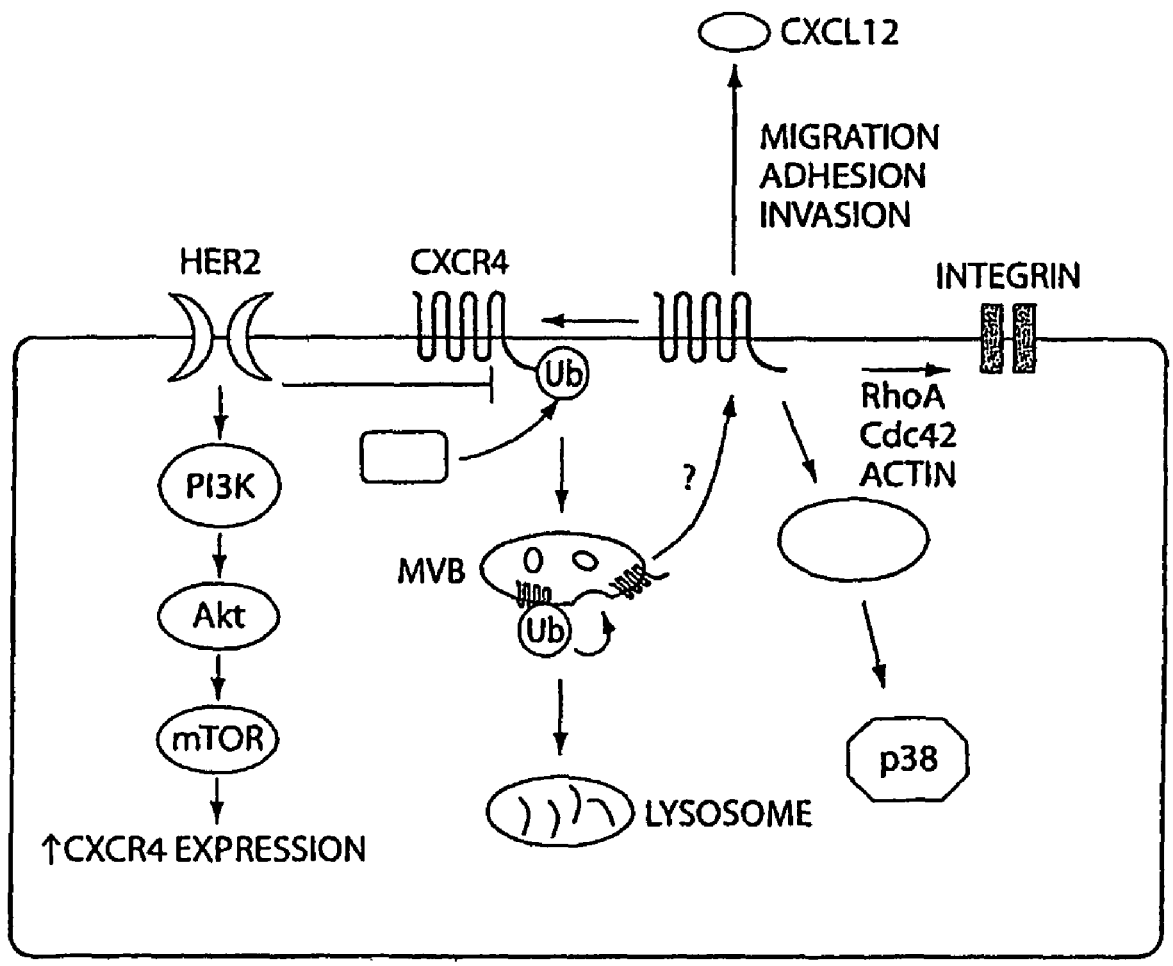
FIG. 13 is a schematic describing the role of HER2 and CXCR4 in cell migration, adhesion, and invasion.

Recently, Li et al. demonstrated that HER2 enhances CXCR4 expression and that CXCR4 is required for HER2-induced breast cancer invasion, migration, adhesion and metastasis to the lung. (See Li et al., Cancer Cell 6:459-69 (2004), which is herein incorporated by reference in its entirety). FIG. 13 is a schematic that describes the role of HER2 and CXCR4 in cell migration, adhesion, and invasion. (See Benovic et al., Cancer Cell 6:429 (2004)).

Herceptin® (trastuzumab) (Genentech, Inc., South San Francisco, Calif.) is a humanized antibody that is FDA-approved to treat HER2 positive metastatic breast cancer. Herceptin is designed to target and block the function of HER2 protein overexpression by potentiation of chemotherapy, inhibition of tumor cell proliferation, and facilitation of immune function. (See Pegram et al, Oncogene 18:2241-51 (1999); Argiris et al., Proc Am Assoc Cancer Res. 41:718. Abstract 4565 (2000); Pietras et al., Oncogene 9:1829-38 (1994); Baselga et al., Cancer Res. 58:2825-31 (1998); Sliwkowski et al., Semin Oncol. 26(suppl 12):60-70 (1999); Lewis et al., Cancer Immunol Immunother. 37:255-63

(1993); and Pegram et al., Proc Am Assoc Cancer Res. 38:602. Abstract 4044 (1997)).

Additionally, Porcile et al. have demonstrated CXCR4 and SDF-1α are expressed in ovarian cancer cell lines. SDF-1α induces a dose-dependent proliferation in ovarian cancer cells by the specific interaction with CXCR4 and a biphasic activation of ERK1/2 and Akt kineases. (See Porcile et al., Ann. N.Y. Acad. Sci. 1030:162-69 (2004), Porcile et al., Experimental Cell Research 308:241-53 (2005)). Porcile et al. further demonstrated that CXCR4 activation induced EGF receptor ("EGFR") phosphorylation, which, in turn, was linked to the downstream intracellular CXCR4-EGFR transactivation. Moreover, the mitogenic activity of SDF-1α was strongly inhibited by a specific inhibitor of EGFR (e.g., tyrphostin AG1478). Thus, an important "cross-talk" between CXCR4 and EGFR intracellular pathways may link different cell-proliferation-related pathways in ovarian cancer cells.

Accordingly, the invention also provides methods of treating or preventing tumor metastasis by administering a therapeutically effective amount of an antibody or antibody fragment of the invention in conjunction with a therapeutically effective amount of one or more EGFR family antagonists. For example, the antibodies of the invention may be co-administered with a therapeutically effective amount of Herceptin®, a VEGFR antagonist, an EGFR antagonist, and/or another HER2 antagonist. Such combination therapy (e.g., the use of one or more of mAb X, and/or scFv X in combination with Herceptin® (or another antagonist of the EGFR family) is expected to have an additive or synergistic effect on the prevention of tumor metastasis.

Determination of the effective amount of the antibody (or antibody fragment) and/or the EGFR family antagonist to be administered to the patient is within the routine skill of those in the art.

Stem Cell Mobilization

Transplantation of $CD34^+$ hematopoietic stem cells can be used to help restore the immune system of patients who have received chemotherapy to treat hematologic cancers such as non-Hodgkin's lymphoma and multiple myeloma. Those skilled in the art will recognize that the strongest predictor of success of such a procedure is the number of stem cells available for transplantation. Thus, it is beneficial (and often necessary) in order to optimize the number of cells available for transplant by using one or more agents that increase the number of stem cells mobilized from the bone marrow into the bloodstream.

Commonly used mobilization agents include, but are not limited to, GM-CSF, G-CSF, AMD3100 (Anormed, Inc., British Columbia, Canada), AMD070 (Anormed, Inc., British Columbia, Canada), CS-3955 (Sankyo Co. Ltd., Tokyo) and/or any structural analogues thereof. G-CSF has been shown control stem cell mobilization through the manipulation of the SDF-1/CXCR4 interaction. (See Petit et al., Nature Immunology 3(7):687-94 (2002)). AMD3100 and AMD070 (an orally bioavailable CXCR4 antagonist) act as stem cell mobilization agents by blocking CXCR4, thereby triggering the rapid movement of stem cells out of the bone marrow and into the circulating blood, where they can be collected for use in stem cell transplantation.

Thus, any of the antibodies or antibody fragments described herein can also be used in a method of mobilizing $CD34^+$ stem cells (e.g., hematopoietic stem cells) from the bone marrow by administering an effective amount of a human monoclonal antibody or of an scFv antibody or of an scFv-Fc fusion of the invention to a patient in need of such treatment. Those skilled in the art will recognize that the administration of the scFvs of the invention (or of some other antibody fragment) may be preferred over the administration of the monoclonal antibodies and/or scFv-Fc fusions of the invention due to the quick clearance rate of scFvs through the kidneys, as compared to that monoclonal antibodies or scFv-Fc fusions.

The antibodies of the invention can be used alone or in combination with an effective amount of one or more additional mobilizing agents (e.g., G-CSF, GM-CSF, and/or AMD3100) in order to mobilize $CD34^+$ stem cells from the bone marrow. For example, in one embodiment, a preferred additional mobilization agent is AMD3100. Determination of the effective amount of the antibody (or antibody fragment) and/or the one or more additional mobilization agents is within the routine skill of those in the art.

Treatment of Graft-Versus-Host Disease

Graft-versus-host-disease ("GVHD") is a condition that can occur following a bone marrow transplant when the donor's immune cells located in the transplanted marrow make antibodies against the host's (e.g., transplant patient's) tissues and attack the patient's vital organs. GVHD may be acute or chronic, mild or severe. Severe cases can often be life-threatening.

Conventional GVHD treatments consist of suppressing the immune response, without damaging the new marrow. Immune suppressants often used to treat cancer are also carefully used in decreased dosages to suppress or prevent graft-versus-host disease. Treatments for acute GVHD can also include high-dose corticosteroids or antibodies to T cells as a second-line option.

$CD4^+CD25^+$ regulatory T cells ("Tregs") mediate peripheral T-cell homeostasis and have been shown to be essential for the induction of tolerance to alloantigens and inhibition of GVHD. (See Zou et al., Cancer Res 64:8451-55 (2004); Taylor et al., J. Exp. Med. 99:3493-99 (2002); Taylor et al., J. Exp. Med. 193:1311-18 (2001)). Zou et al., have recently provided evidence that CXCR4/SDF-1 signals play an important role in regulating Treg egress from bone marrow and in maintaining homeostatic levels of Tregs in the periphery. (Zou et al., Cancer Res 64:8451-55 (2004), which is incorporated herein by reference in its entirety). Moreover, the administration of G-CSF has been shown to mobilize Tregs from the bone marrow into the periphery by decreasing marrow SDF-1 expression. (See id.; Levesque et al., J. Clin Investig. 11:187-96 (2003); Petit et al., Nat. Immunol. 3:687-94 (2002)).

Thus, blocking SDF-1/CXCR4 signals can reduce the degree of Treg trafficking to the bone marrow. (See Zou et al., Cancer Res 64:8451-55 (2004)). As a result, disruption of the SDF-1/CXCR4 interaction may increase the number of Tregs present in the periphery, thereby increasing the number of Tregs available to inhibit GVHD.

Accordingly, the invention also provides a method of treating or preventing GVHD in a patient suffering from (or as risk of suffering from) GVHD by administering an effective amount of any of the antibodies (or antibody fragments) of the invention (alone or in combination). Moreover, the antibodies and antibody fragments of the invention can be used alone or in combination with an effective amount of one or more mobilizing agents (e.g., G-CSF, GM-CSF, and/or AMD3100) in order to mobilize Tregs from the bone marrow. For example, in one embodiment, a preferred additional mobilization agent is AMD3100. Determination of the effective amount of the antibody (or antibody fragment) and/or the one or more mobilization agents is within the routine skill of those in the art.

Blocking Chemotaxis

Chemotaxis is the phenomenon by which bacteria, other organisms, or single cells of multicellular organisms direct their movements according to certain chemicals in their environment. Some eukaryotic cells, such as immune cells also move to where they need to be by sensing the presence of chemotactic stimuli though the use of 7-transmembrane (or serpentine) heterotrimeric G-protein coupled receptors.

Figure 14:
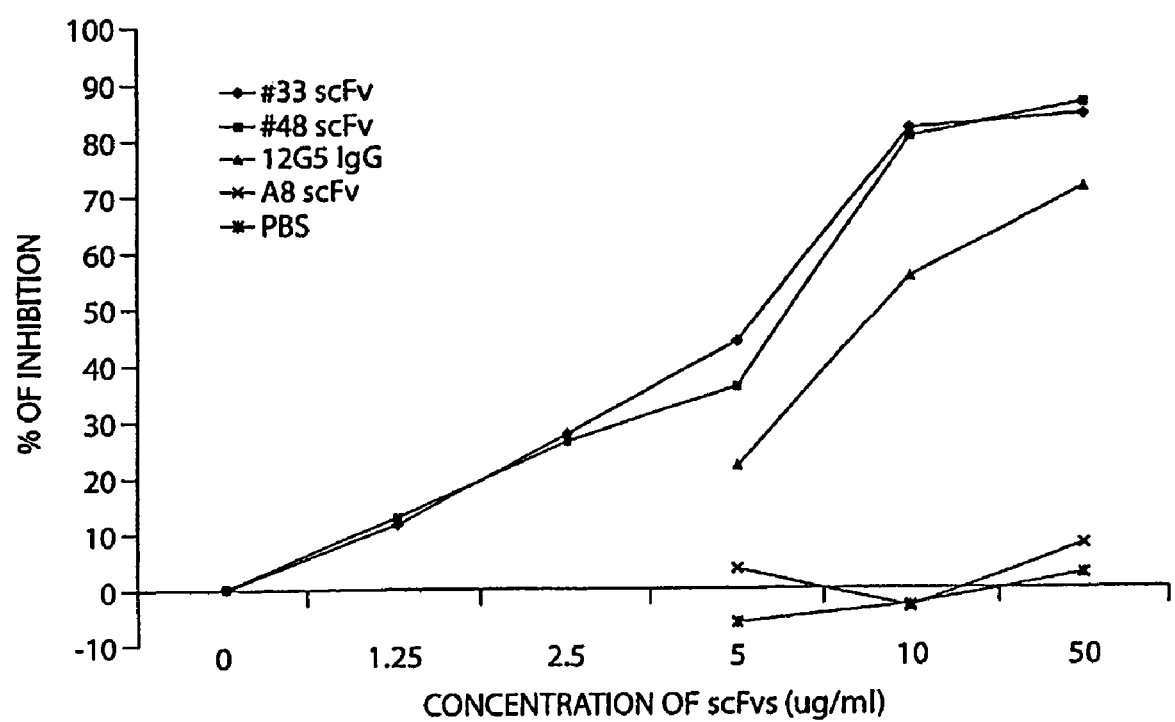
FIG. 14 is a graph showing the effects of scFvs 33 and 48 on SDF-1 mediated chemotaxis of Jurkat T-cells.

Any of the antibodies (or antibody fragments) described herein can be used to block chemotaxis of CXCR4-expressing cells in response to the chemokine SDF-1. (See Tashiro et al., Science 261:600-03 (1993); Nagasawa et al., Nature 382:635-38 (1996)). Specifically, an effective amount of the monoclonal antibodies, scFv antibodies, scFv-Fc fusions, minibodies, and/or diabodies of the invention can be administered to a subject in which blocking of the chemotaxis of CXCR4-expressing cells is desired. For example, CXCR4-expressing cells may include Jurkat T-cells, T-cells, endothelial cells, neural stem cells (see Imitola et al., Proc Natl Acad Sci USA 101(52):18117-22 (2004)), breast cancer cells, and tumor cells. As shown in FIG. 14, scFvs 33 and 48 were able to block SDF-1 mediated chemotaxis of Jurkat T cells.

Determination of the effective amount of the antibody or antibody fragment to be administered is within the routine skill of those in the art.

Inhibition of the Formation of New Tumor Blood Vessels in Cancer Therapy

Ceradini et al. have recently shown that the recruitment of CXCR4-positive progenitor cells to regenerating tissue to aid in the formation of new tumor blood vessels is mediated by hypoxic gradients via HIF-1-induced expression of SDF-1. (See Ceradini et al., Nature Med. 10(8):858-64 (2004)).

Thus, an effective amount of any of the antibodies (or antibody fragments) of the invention can be administered to a patient suffering from a cancer in which hypoxia leads to the local secretion of SDF-1. Such administration can inhibit the formation of new tumor blood vessels by blocking the interaction between SDF-1 and CXCR4, thereby inhibiting the recruitment of endothelial cell precursor cells to aid in the formation of new tumor blood vessels. Cancers in which hypoxia leads to local secretion of SDF-1 include renal cell carcinomas as well as any tumor that becomes hypoxic over time (e.g., any solid tumor). Thus, such methods may provide a means for treating cancers by using the antibodies or antibody fragments of the invention as anti-angiogenic agents. Determination of the effective amount of the antibody (or antibody fragment) to be administered is within the routine skill of those in the art.

Inhibition of Tumor Angiogenesis

Tumor angiogenesis is essential for the growth of primary and metastatic tumors. Tumors and metastases may originate as small avascular masses that induce the development of new blood vessels once they grow to a few millimeters in size. (See Hanahan et al., Cell 86:353-64 (1996); Folkman et al., Cell 87:1153-55 (1996)). However, many studies indicate that tumor antiangiogenic therapy leads to an inhibition of tumor growth rather than to a regression of established tumors. (See Warren et al., J. Clin. Invest. 95:1789-97 (1995); Shaheen et al., Cancer Res. 59:5412-16 (1999)).

Kryczek et al. have recently shown that SDF-1 and vascular endothelial growth factor ("VEGF") form a synergistic angiogenic axis that induces angiogenesis in vivo in ovarian carcinomas. (See Kryczek et al., Cancer Res. 65(2):465-72 (2005), herein incorporated by reference in its entirety). Moreover, Kryczek et al. also noted that preincubation with a neutralizing antibody against CXCR4 completely disabled SDF-1-mediated human vascular endothelial cell ("HUVEC") migration in the presence of VEGF, thereby confirming the involvement of CXCR4. In fact, VEGF sensitized SDF-1-mediated HUVEC migration through the up-regulation of CXCR4. (See id.).

Those skilled in the art will recognize that survival of vascular endothelial cells is critical for forming stable neovascularization. Moreover, hypoxia synchronously triggers both VEGF and SDF-1 production by tumor cells. (See Carmeliet et al., Nature 407:249-57 (2000)). Additionally, as shown by Kryczek et al., SDF-1 and VEGF synergistically promote vascular endothelial cell function, including migration, expansion, and survival. Therefore, in many human tumors, hypoxia may induce VEGF and SDF-1 production, which, in turn, synergistically protect tumor cell or vascular endothelial cell apoptosis from hypoxia in the tumor environment and synergistically promote tumor vascularization and growth.

It is possible that, by depriving tumors of oxygen, certain angiogenesis antagonists or inhibitors may actually promote tumor metastasis by increasing CXCR4 expression. (See Kryczek et al., Cancer Res. 65(2):465-72 (2005)) Thus, agents that block both CXCR4 and VEGF (e.g., any of the antibodies or antibody fragments of the instant invention alone or in conjunction with an anti-VEGF-antibody, such as Avastin™ (Genentech, Inc., South San Francisco, Calif.)) can be used to efficiently treat for human cancers by blocking tumor angiogenesis. Specifically, the invention also provides methods of inhibiting tumor cell angiogenesis in patients suffering from (or as risk of suffering from) cancer by administering an effective amount of any of the antibodies (or antibody fragments) of the invention in conjunction with an anti-VEGF antibody in order to block the synergistic effect of VEGF and SDF-1 on tumor cell angiogenesis. By way of non-limiting example, the cancer may be ovarian carcinoma.

Determination of the effective amount of the antibody (or antibody fragment) of the invention and/or the anti-VEGF antibody to be administered is within the routine skill of those in the art.

The invention will be further described in the following examples, which do not limit the scope of the invention described in the claims.

EXAMPLES

Example 1

Purification of CXCR4 Proteoliposomes

CXCR4-Cf2Th cells were grown to full confluency in 100 mm cell culture dishes. Cells were detached from the dish with 1×.PBS/5 mM EDTA and pelleted in microcentrifuge tubes at $1 \times 10^8$ cells/pellet. The pellet was resuspended in an ice cold buffer containing 100 mM $(NH_4)_2SO_4$, 20 mM Tris pH 7.5, 20% glycerol, 1× Complete (Roche) protease inhibitor cocktail and 1% of either CHAPSO (Anatrace) or Cymal-7 (Anatrace). Resuspended cells were incubated for 5 minutes on ice followed by 25 minutes at 4° C. on a Rotator (Fisher Scientific).

After incubation, cell debris was removed by centrifugation at 14,000×g for 30 minutes at 4° C. The supernatant was transferred to a new microcentrifuge tube and $5 \times 10^8$ 1D4 conjugated M-280 Dynal beads were added. Cell lysate was incubated with beads for 2.5 hours at 4° C. on a Nutator. The tube was then placed in a Dynal MPC-S magnet to remove the beads. The beads were washed two times with ice cold washing buffer (either 1% CHAPSO or Cymal-7, 100 mM $(NH_4)_2SO_4$, 20 mM Tris pH 7.5 and 20% glycerol). After washing, beads prepared with CHAPSO were resuspended in 2.5 ml of ice cold CHAPSO washing buffer containing 1.5 mg 1-Palmitoyl-2-Oleoyl-sn-Glycero-3-Phosphocholine, 0.75 mg 1-Palmitoyl-2-Oleoyl-sn-Glycero-3-Phosphoethanolamine, 0.225 mg 1.2 Dioleoyl-sn-Glycero-3-Phosphate and 0.025 mg Biotinyl-Phosphoethanolamine. Cymal-7 prepared beads were resuspended in ice cold 1% Cymal-5 washing buffer containing the above described lipids.

The solution was then injected into a Slide-A-Lyzer (Pierce, 10 kDMWCO) and dialyzed for 24 hours against washing buffer containing no detergent at 4° C. The samples were dialyzed in a specially designed machine that constantly rotated the Slide-A-Lyzer to prevent settling of the beads. Following dialysis, the paramagnetic proteoliposomes were removed from the Slide-A-Lyzer and washed two times in 1×PBS/2% FBS to remove unbound lipid and any remaining detergent. Proteoliposomes were stored in 1×PBS/2% FBS/0.02% sodium azide for up to two months at 4° C.

Figure 15:
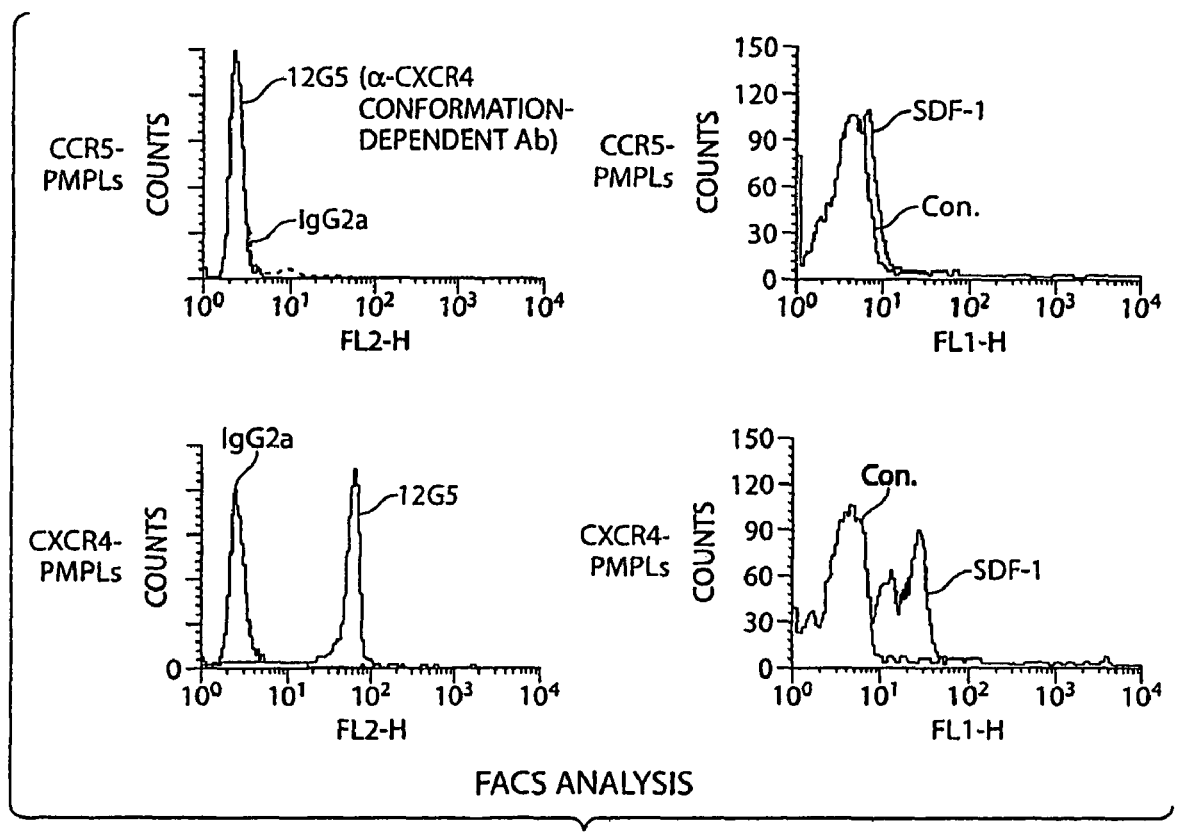
FIG. 15 is a series of FACS analysis graphs demonstrating that CXCR4 proteoliposomes prepared according to the methods of Example 1 are able to bind to the conformationally-sensitive anti-CXCR4 monoclonal antibody 12G5. In addition, FACS analysis also demonstrates that the CXCR4 proteoliposomes are able to bind to the CXCR4 ligand, SDF-1.

Using FACS analysis, CXCR4 proteoliposomes prepared according to this method have been shown to be able to bind to the conformationally-sensitive anti-CXCR4 monoclonal antibody, 12G5, as well as to the CXCR4 ligand, SDF-1. (See FIG. 15). In addition, as shown in FIG. 16B, SDS-PAGE analysis can be performed to characterize and analyze the protein composition of the resulting paramagnetic proteoliposomes.

Example 2

Selection of Phage Library and Screening of Phage Antibodies

Selection Using Wild Type CXCR4 Paramagnetic Proteoliposomes

Two human non-immune scFv libraries (having a total of $2.7 \times 10^{10}$ members) constructed from B-cells of 57 un-immunized donors were used for selection of scFvs against wild type CXCR4 proteoliposomes.

$5 \times 10^{12}$ phage library was blocked in 4% nonfat milk/2% BSA/PBS at RT for 30 mins, and absorption was performed by incubating preblocked library with $3 \times 10^7$ cf2Th cells and $3 \times 10^7$ magnetic beads conjugated with 1D4 antibody for 1 hr at 4° C. Supernatant was collected and incubated with $3 \times 10^7$ human-CXCR4 proteoliposomes prepared as described in Example 1 at 4° C. for 4 hr by end-over-end rotation. Paramagnetic proteoliposomes were washed 15 times by 0.05% Tween-20/PBS to remove non-specifically absorbed phages. Captured phage were eluted by addition of 500 µl 0.1M triethylamine and incubation for 20 min, then neutralized with 500 µl 1M Tris/HCl, pH 6.8. Half of the eluted phage was used to infect an exponentially growing culture of *E. coli* TG1 for amplification and preparation for further round of panning. Three rounds of panning were performed.

A summary of three rounds of antibody-phage panning on human-CXCR4 paramagnetic proteoliposomes is shown in Table 1, supra.

Specific bound phages were detected by adding HRP-conjugated mouse anti-M13 and the system was developed by adding TMB substrate. Absorbance at 450 nm was measured. Clones that bound to CXCR4 proteoliposomes with $A_{450}$ values of >1.0 were scored as positive, whereas negative clones gave values of <0.2. For CXCR4-specific binding clones (e.g., clones 18, 19, 20, 33, and 48), the genes of variable regions of heavy (VH) and light (VL) chain were sequenced and their corresponding amino acid sequences were aligned. (See FIG. 1).

Modified Selection Using Wild Type and Truncated CXCR4 Paramagnetic Proteoliposomes Six stable cell lines were first established. These included wild type CXCR4 and two N-terminal truncations of CXCR4 (ΔN25-CXCR4 and ΔN31-CXCR4) expressed on Cf2Th and 293T cells respectively. These cell lines were named Cf2-X4, Cf2-ΔN25-X4, Cf2-ΔN31-X4, 293T-X4, 293T-ΔN25-X4 and 293T-ΔN31-X4. Wild type CXCR4 and its truncations were made to include a 9-amino-acid tag (C9) at it is Carboxyl-terminal for purification using antibody 1D4, which is a high affinity antibody against C9. The sequences of wild-type, ΔN25-CXCR4 and ΔN31-CXCR4 are shown in FIG. 21.

Figure 22:
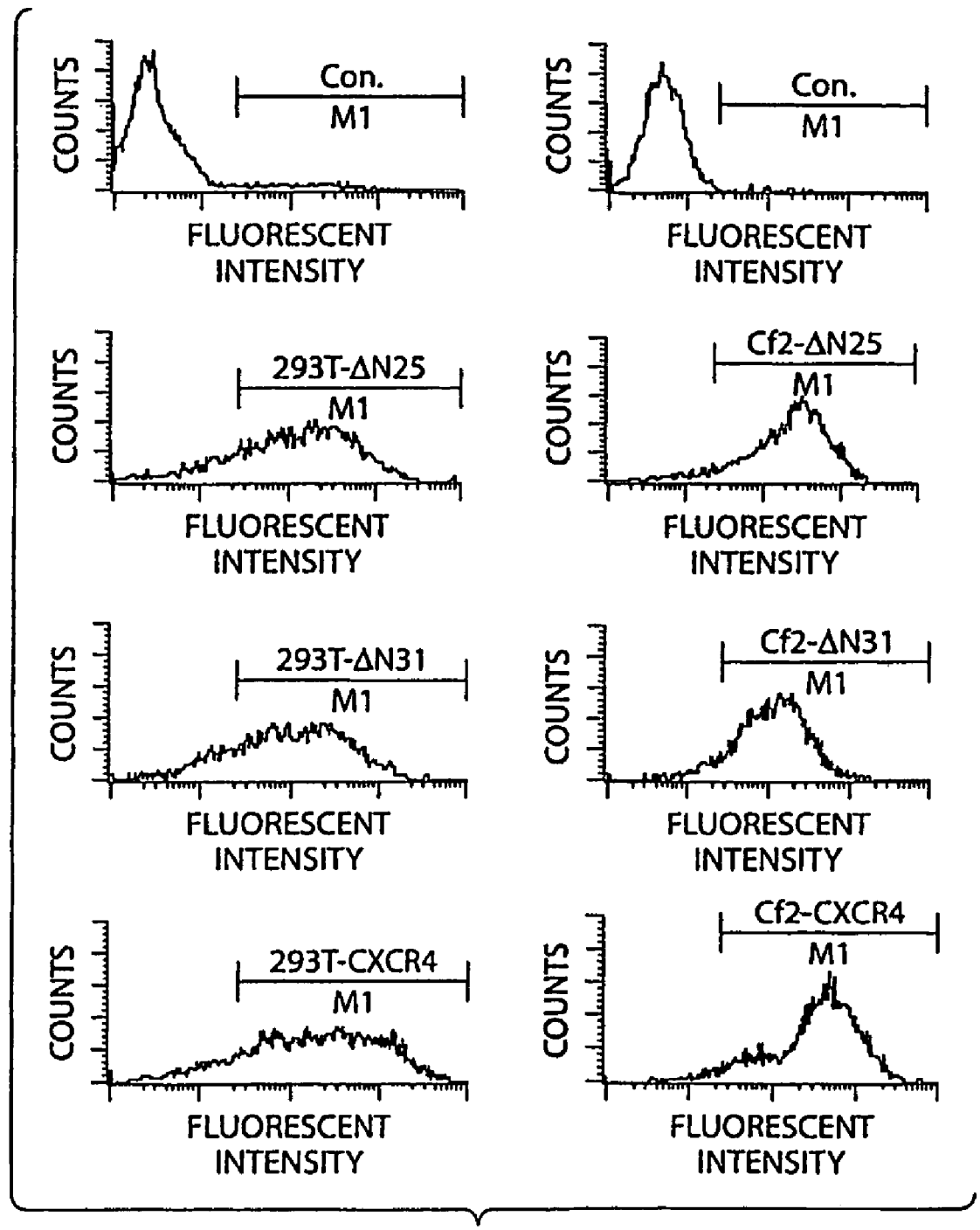
FIG. 22 is a series of FACS analysis graphs demonstrating the expression of wild-type CXCR4, ΔN25-CXCR4, and ΔN31-CXCR4 on Cf2Th and 293T cells.

The existence of stable cell lines expressing CXCR4 and NT deletions of CXCR4 was determined by FACS analysis. As shown in FIG. 22, the NT deletions and wild-type CXCR4 expressed well on both Cf2 and 293T cell surface.

Figure 23:
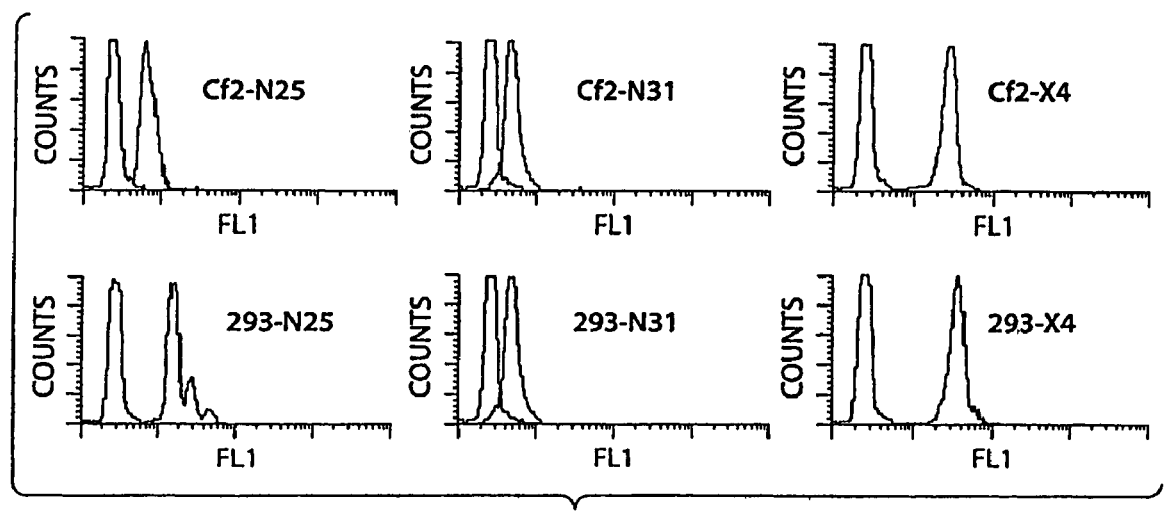
FIG. 23 is a series of FACS analysis graphs demonstrating that the paramagnetic proteoliposomes prepared according to the methods of Example 1, supra presented functional CXCR4s that can be recognized by the conformational CXCR4 antibody 12G5.

These 6 stable cell lines were used to prepare a total of 6 different CXCR4-containing paramagnetic proteoliposomes according to the methods of Example 1, supra. FIG. 23 shows that these paramagnetic proteoliposomes presented functional CXCR4s that can be recognized by conformational CXCR4 antibody 12G5. The right hand peak indicated positive binding of 12G5 on various CXCR4 paramagnetic proteoliposomes. Because the Cf2-N31 and 293-N31 were only weakly recognized, the other 4 paramagnetic proteoliposomes were chosen for the antibody library selection.

Two human non-immune scFv libraries (having a total of $2.7 \times 10^{10}$ members) constructed from B-cells of 57 un-immunized donors were used for selection of scFvs against CXCR4 proteoliposomes.

A total of $1 \times 10^{13}$ of phages from two libraries was blocked in 4% nonfat milk/2% BSA/PBS at RT for 30 mins. These phages were first absorbed with $5 \times 10^7$ Cf2Th cells or 293T cells and $3 \times 10^7$ CCR5 paramagnetic proteoliposomes made in accordance with the methods of Example 1, supra for 1 hr at 4° C. CCR5 is another 7-transmembrane domain protein that was used to subtract the non-CXCR4 antibodies from the libraries. Supernatant was collected and incubated with $3 \times 10^7$ human-CXCR4 proteoliposomes (Cf2-N25, Cf2-X4, 293-N25, 293-X4, respectively) prepared as described in Example 1 at 4° C. for 2 hr by end-over-end rotation. The paramagnetic proteoliposomes were washed 15 times by 0.05% Tween-20/PBS to remove non-specifically bound phages. Captured phage were eluted by addition of 1 ml 0.1M triethylamine and incubation for 20 min, then neutralized with 700 µl 1M Tris/HCl, pH 7.4. Half of the eluted phage was used to infect an exponentially growing culture of *E. coli* TG1 for amplification and preparation for further round of panning.

Two rounds of selection were performed. After the second round of selection, clones were randomly picked up to screen for C12-CXCR4 cell positive clones by FACS analysis. In brief, 500,000 cells were stained with phage-Abs in 96 well plates; the phages and cells were pre-blocked with 2% BSA/PBS before mixing them together; and the bound phages were detected by anti-M13 antibody followed by FITC-anti-Mouse antibody.

A summary of two rounds of antibody library selection on truncated human-CXCR4 paramagnetic proteoliposomes is shown in Table 4. As shown in Table 4, four unique antibodies against CXCR4 were identified using this method. Among these four antibodies, 1N and 5N were very similar to antibody 48, which had been previously identified. As such, they were not characterized further. However, two new anti-CXCR4 antibodies (2N and 6R) were characterized.

The genes of variable regions of heavy (VH) and light (VL) chain were sequenced and their corresponding amino acid sequences were aligned. (See FIG. 1).

TABLE 4

| | Paramagnetic Proteoliposome | 1st round selection | | 2nd round selection | | Positive clones after 2nd round selection (positive clone number/ total screened cone) | Unique Clones (Name) |
|---|---|---|---|---|---|---|---|
| | | Input phage number | Eluted phage number | Input phage number | Eluted phage number | | |
| 1 | Cf2-X4 | 5 × 10e12 | 3.6 × 10e5 | 2 × 10e12 | 1.2 × 10e5 | 5/192 | 3 (1N, 2N, 5N) |
| 2 | Cf2-ΔN25-X4 | 5 × 10e12 | 8.2 × 10e5 | 2 × 10e12 | 1.0 × 10e5 | 0/192 | 0 |
| 3 | 293T-X4 | 5 × 10e12 | 3 × 10e5 | 2 × 10e12 | 3.5 × 10e5 | 1/192 | 1 (6R) |
| 4 | 293T-ΔN25-X4 | 5 × 10e12 | 3.4 × 10e5 | 2 × 10e12 | 4 × 10e5 | 5/384 | 1 (2N) |

Example 3

Expression and Purification of scFvs, Whole Human IgG1s and scFv-Fc Fusions

Those skilled in the art will recognize that the VH and VL fragments of the identified scFvs can be rebuilt either as a human IgG1 molecule or as an scFv-Fc fusion. Specifically, the VH and VL gene fragments of seven CXCR4-specific scFvs (#2N, 6R, 18, 19, 20, 33, and 48) were cloned into prokaryotic expressing vector pSyn1. All scFvs contain a His-6 tag that allows purification by immobilized metal affinity chromatography (IMAC). The CXCR4-binding activity of purified soluble scFvs were confirmed by FACS. The FITC conjugated 9E10 or PE conjugated 9E10 antibody (which recognizes the c-myc tag that is fused with scFvs) was used to detect the bound scFvs on the cell surface.

FACS analysis of two of the identified anti-CXCR4 scFvs (e.g. scFv 33 and scFv 48) demonstrated that these scFvs specifically bind to CXCR4, but did not bind to the closely related chemokine receptors CCR5, CXC1, CXCR2, GPR15, CXCR6. (See FIGS. 4 and 6). FACS analysis also demonstrated that scFvs 33, 48, X18, X19, and X20 specifically bind to CXCR4, but did not bind to the CCR5 or to the Cf2Th cell, which does not express CXCR4. (See FIG. 24). In addition, these five scFvs (33, 48, X18, X19, and X20) could compete with 12G5 for binding to CXCR4 on the cell surface. (See FIG. 25).

For expression of the scFv-Fc, the VH-linker-VL genes of these clones were cloned into pcDNA3.1-Hinge vector which contains Fc portion of human antibody IgG1. This vector allows us to express antibodies in the scFv-Fc format. The scFv-Fcs were expressed by transiently transfecting 293T cells, and antibodies were purified from cell culture supernatants by protein A Sepharose beads.

For production of whole human IgG1, the VH and VL gene fragments of the scFv were separately subcloned into human IgG1 lambda light chain expression vector TCAE6. (See Reff et al., Blood 83:435-45 (1994)). IgG1 was expressed in 293T cells by transient transfection or stable expressing CHO cell line and purified by protein A sepharose affinity chromatography.

Protocols for the Preparation of scFvs from *E. coli*:
Sample Preparation:
1. Grow up 1 liter of bacterials (clone 18(22C1) and 92(33B3) were transformed in XLI-Blue) in big flask in the medium of 2YTGAT (Glucose: 0.05-0.1%, (crucial), Amp: 100 μg/ml, Tet: 12.5 μg/ml, Tet is not necessary)
2. Grow to OD$_{600}$=0.9 (at this point, the glucose is consumed, the addition of IPTG will result in induction of expression from the lac promoter)
3. Induce expression of scFvs with 250-500 μM IPTG (5 ml of 100 mM)
4. Incubate overnight at 25° C.
5. Spin down the induced bacterial at 6000 rpm for 15 min
6. Resuspend pellet in 1/20 (50 ml) the original volume of cold PBS containing cocktail protease inhibitor (Roche)
7. Sonicate the culture for 3 min (nine cycles of 20 sec on, 10 sec off) in a 200 ml small beaker. For 400 ml culture sonicate for 2 min in 25 ml tube
8. Spin down the cell debris at 12000 g for 20 min at 4° C.
9. Spin the supernatant again at 12000 rpm for 5 mins
10. Adjust pH with 1M Tris.Cl (pH 8.0) to neutral. Precipitate the proteins in 50% (NH4)$_2$SO$_4$. Place the protein solution on magnetic stirrer and stir the solution slowly when ASA (ASA: saturated ammonium sulfate, 4.1M, 761 g/1 L H$_2$O) is added, drop by drop until 50 ml ASA is added. Leave at 4° C. for several hours or overnight
11. Spin down at 14000 rpm for 20 min. Discard the supernatant completely. Dissolve the pellet into 10 ml Buffer A (PBS/0.5MNaCl) containing 10 mM Imidazole IMAC:
1. Prepare a column of Chelating Sepharose, 1-2 ml of resin per 1 L of flask culture. Fill a PD-10 column with 1 ml of resin
2. Wash the column with 5× gel volumes of water
3. Charge the column with Ni$^{2+}$ by loading 0.7 gel volume of 0.1 M NiCl$_2$ or NiSO$_4$; seal the column with the top cap and the bottom cap; and incubate with gentle end-over-end rotation for 5 mins at RT Open the bottom cap. Wash the excess of ions with 5 bed volumes of water
4. Equilibrate with 5× gel volumes of Buffer A
5. Load sample and incubate for 30 mins at RT with end-over-end rotation
6. Wash with 20 ml gel volumes of 20 mM Imidazole Buffer A. Collect the flow-through.
7. Wash with 20 ml of 60 mM Imidazole Buffer A
8. Elute with 5 ml 100 mM Imidazole Buffer A
9. Elute with 10 ml 500 mM Imidazole Buffer A. (Avoid dilution by collecting the eluate in 1 ml fraction)
10. Thoroughly dialyze the eluates against PBS. Separate Eluate 8 and 9. Because fraction 9 is purer than fraction 8, fraction 9 is used to do further biological studies Example 4:

Saturation Binding Analysis of Identified Antibodies

Jurkat and Cf2.Th-CXCR4 cells were prepared for culturing with different concentrations of antibodies. Clones 2N-Fc, 6R-Fc, 18-Fc, 19-Fc, 20-Fc, 33-Fc, 48-Fc and murine monoclonal antibody 12G5 were added to the cells in the following concentrations: 0.5, 2.5, 10, and 25 μg/ml. (See FIGS. 9A-D). The cells were then washed two times with 0.5% BSA/PBS/0.02% NaN3.

Next, FITC-labeled secondary antibodies were added to the cells and were allowed to incubate at 4° C. for 30 minutes.

The cells were then washed again two times with 0.5% BSA/PBS/0.02% NaN3. Following the second wash, FACS analysis was performed.

Results of these saturation binding studies are provided in FIGS. 9A-F.

Example 5

Epitope Mapping 293T cells were transfected with CXCR2/CXCR4 chimeric mutants and other N-terminal deletions (see Tables 2 and 3, supra). Thirty six hours after transfection, the cells were harvested. The scFv-Fc fusions of the invention (e.g., X-Fc) along with monoclonal antibody 12G5 and control antibodies were added to the cells and allowed to incubate for 1 hour. The cells were then washed two times with 0.5% BSA/PBS/0.02% NaN3.

Next, FITC-labeled secondary antibodies were added to the cells and were allowed to incubate at 4° C. for 30 minutes. The cells were then washed again two times with 0.5% BSA/PBS/0.02% NaN3. Following the second wash, FACS analysis was performed.

Example 6

Prevention of T-tropic X4 HIV-1 Infection

One day before viral infection, cf2ThCD4CXCR4 cells were seeded in 96-well flat-bottom Opaque/Black Tissue Culture Plate (Becton Dickinson) at 6000 cell/well. On the next day, supernatant was absorbed and 50 µl DMEM medium was added to each well with or without CXCR4-specific scFvs or control antibodies at the concentration indicated. After incubation at 37° C. for 30 mins, single round luciferase reporter pseudotype viruses were added to cells. After another two-hour incubation, antibodies and viruses were washed out and the cells were cultured with new total DMEM medium for 48 hrs at 37° C., 5% CO2. Luciferase activity were measured by EG&G Berthold Microplate Luminometer LB. Results are shown in FIGS. 10 and 11.

Example 7

Blocking Chemotaxis

Jurkat cells were collected with 0.5% EDTA/PBS and washed twice with chemotaxis buffer (0.1% BSA/RPMI 1640 medium). 200,000 cells were resuspended in 100 µl chemotaxis buffer with or without CXCR4 specific scFvs or control antibodies and incubated at 37° C. for 30 min. Cells solution were transferred to the upper well of Corning Costar Transwell (6.5 mm diameter, 5.0 µm pore size) which lower well containing 50 ng/ml human SDF-1α in 0.6 ml chemotaxis buffer.

Figure 7:
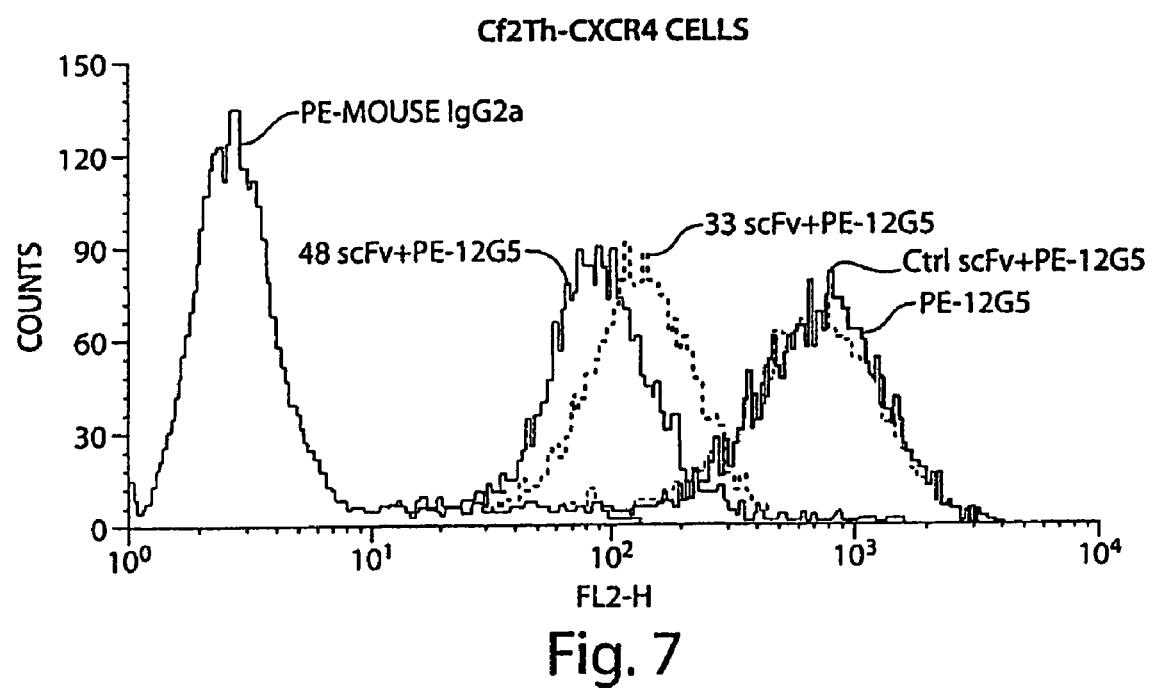
FIG. 7 is a FACS scan analysis graph, which demonstrates that scFv clones 33 and 48 compete with the neutralizing anti-CXCR4 monoclonal antibody, 12G5 for binding to CXCR4.

After incubation for 4 hrs at 37° C., cells in lower well were collected and cell number was counted. For each concentration, duplicate samples were tested. Percentage of inhibition was calculated as the following formula: % of Inhibition=100×(1−average cell number under treatment of scFvs or IgG/average cells number without treatment). Results for scFv clones 33 and 48 are shown in FIG. 7.

Example 8

Effects of Hypoxia on CXCR4 Expression on Breast Cancer Cells

To evaluate the effects of hypoxia on CXCR4 expression on breast cancer cells, several breast cancer cells were treated under both hypoxic conditions (1% $O_2$) and normal tissue culture conditions (in parallel) for 12 hours.

In one experiment, the cells were then harvested and the 12G5, 33 and 48 antibodies were added to the cells. Following incubation, the cells were washed two times with 0.5% BSA/PBS/0.02% NaN3. Next, FITC-labeled secondary antibodies were added to the cells and were allowed to incubate at 4° C. for 30 minutes. The cells were then washed again two times with 0.5% BSA/PBS/0.02% NaN3. Following the second wash, FACS analysis was performed.

Figure 17:
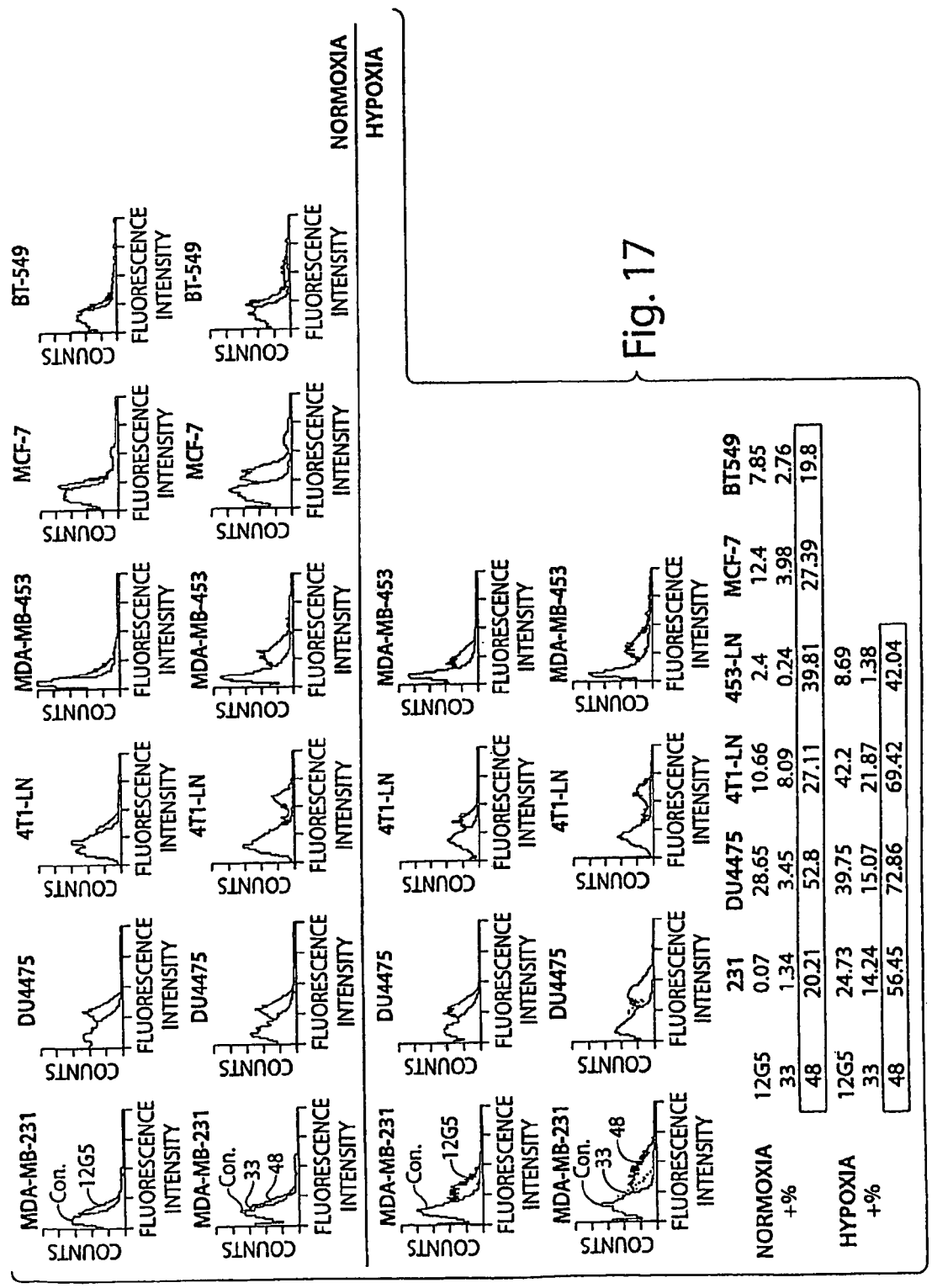
FIG. 17 is a series of FACS analysis graphs demonstrating the effects of hypoxia on CXCR4 expression on breast cancer cells.
Figure 18:
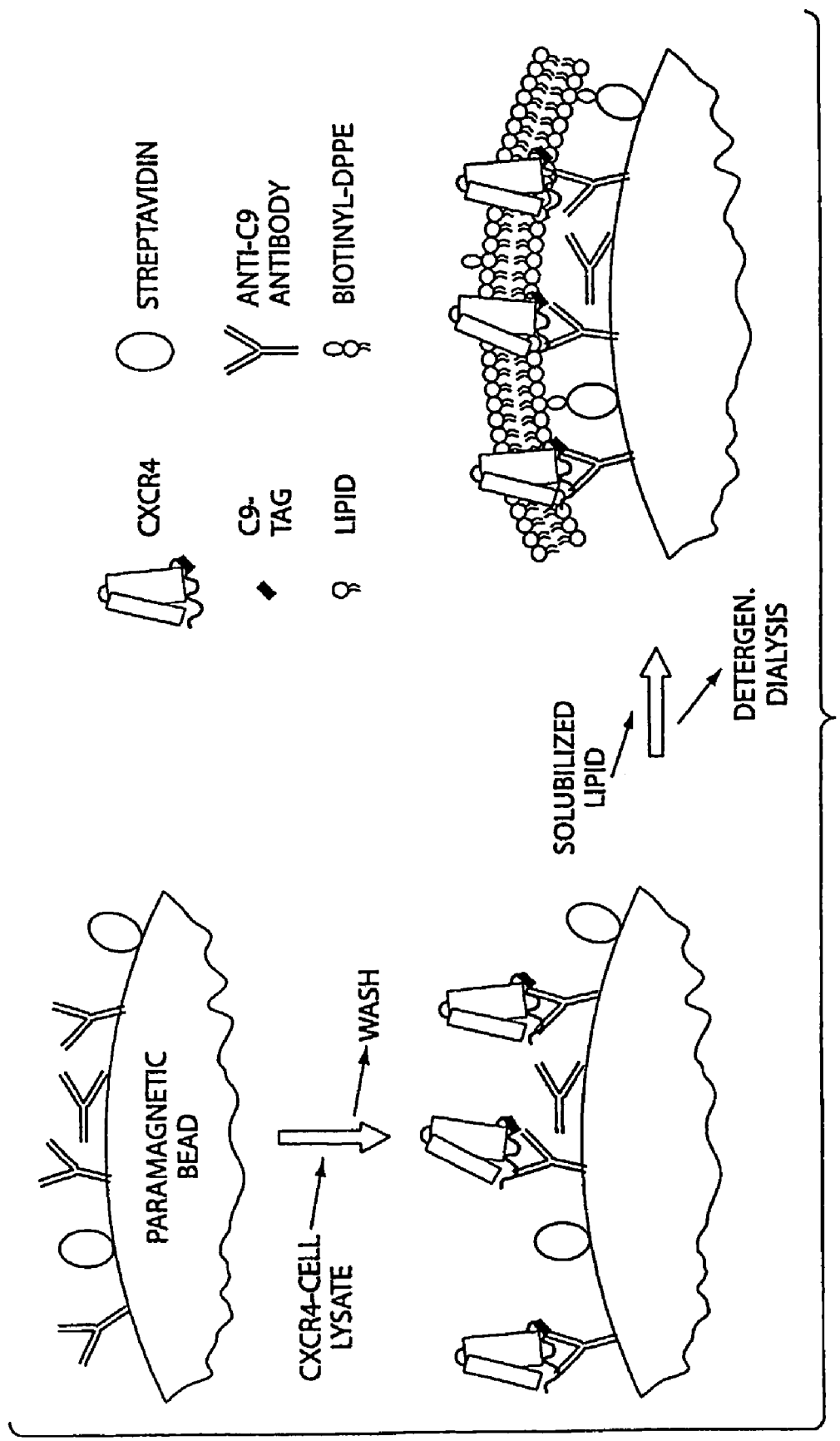
FIG. 18 is a schematic detailing the preparation of CXCR4-containing paramagnetic proteoliposomes.

The results of this experiment are presented in FIG. 17, which shows that hypoxic conditions (i.e., oxygen tension conditions), increases the cell surface expression of CXCR4.

Example 9

Evaluation of the Effect of the Anti-CXCR4 Antibody 48-Fc in Nude Mice Model of Breast Cancer One of the human CXCR4 antibodies disclosed herein (48-Fc) has been tested in an experimental metastasis model in nude mice. Nude mice were injected with tumor cells MDA-MB-231 (which is luciferized using a stably expressed luciferase gene to enable tracking of metastasized cells using a Xenogen imaging system) through tail vein. Three study groups were examined, and each group had 5 mice. The 3 groups were the non-treatment group, the treatment with normal human IgG1 control, and the 48-Fc treatment group.

Following the injection of the tumor cells, antibody 48-Fc and a control antibody (Normal human IgG1) were also injected intraperitoneally (IP) on the same day. The mice were monitored for metastasis by periodically imaging the mice (twice a week), and antibodies were administered twice a week by IP injection at a dose of 20 mg/kg of mice. After 6 weeks, mice were euthanized and lung tissues were taken and sent for histological study.

Both Xenogen imaging result and histological result indicated that 48-Fc treatment might have inhibited the lung metastasis of tumor cells. (See FIGS. 26A-D and 27). More thorough (and better controlled) experiments are currently underway to further confirm this result. This further in vivo data obtained will show whether the 48-Fc antibody has any effect on breast cancer growth and metastasis.

The other CXCR4 antibodies disclosed herein have not yet been tested in vivo. However, they will be tested in the future using the experimental methods outlined herein.

Other Embodiments

Although particular embodiments have been disclosed herein in detail, this has been done by way of example for purposes of illustration only, and is not intended to be limiting with respect to the scope of the appended claims, which follow. In particular, it is contemplated by the inventors that various substitutions, alterations, and modifications may be made to the invention without departing from the spirit and scope of the invention as defined by the claims. Other aspects, advantages, and modifications considered to be within the scope of the following claims. The claims presented are representative of the inventions disclosed herein. Other, unclaimed inventions are also contemplated. Applicants reserve the right to pursue such inventions in later claims.

We claim:

1. A human monoclonal antibody or an scFv antibody, which binds to the chemokine receptor CXCR4 and has a heavy chain with three CDRs comprising the amino acid sequences SYGIS (SEQ ID NO:29), WISAYNGNTNYAQKLQG (SEQ ID NO:30), and DTPGIAARRYYYYGMDV (SEQ ID NO:31), respectively, and a light chain with three CDRs comprising the amino acid sequences QGDSLRKFFAS (SEQ ID NO:32), GKNSRPS (SEQ ID NO:33), and NSRDSRDNHQV (SEQ ID NO:34), respectively.

2. The human monoclonal antibody or scFv antibody of claim 1, wherein the monoclonal antibody comprises a heavy chain variable region comprising the amino acid sequence of SEQ ID NO: 4 and a light chain variable region comprising the amino acid sequence of SEQ ID NO: 12.

3. The human monoclonal antibody of claim 1, wherein said monoclonal antibody blocks the function of SDF-1.

4. The scFv antibody of claim 1, wherein said scFv antibody blocks the function of SDF-1.

5. A composition comprising the human monoclonal antibody or scFv antibody of claim 1, and a carrier.

6. A kit comprising, in one or more containers, the composition of claim 5.

7. A method of reducing X4-tropic HIV-1 infection, the method comprising administering to a subject in need thereof an effective amount of a pharmaceutical composition of the human monoclonal antibody of claim 1, prior to the manifestation of symptoms characteristic of X4-tropic HIV-1 infection.

8. A fusion protein comprising an anti-CXCR4 antibody fragment fused to a human protamine protein or fragment thereof, wherein the anti-CXCR4 antibody fragment comprises a.) a heavy chain variable region comprising the amino acid sequence of SEQ ID NO: 4 and a light chain variable region comprising the amino acid sequence of SEQ ID NO:12; or b.) a heavy chain with three CDRs comprising the amino acid sequences SYGIS (SEQ ID NO:29), WISAYNGNTNYAQKLQG (SEQ ID NO:30), and DTPGIAARRYYYYGMDV (SEQ ID NO:31) respectively and a light chain with three CDRs comprising the amino acid sequences QGDSLRKFFAS (SEQ ID NO:32), GKNSRPS (SEQ ID NO:33), and NSRDSRDNHQV (SEQ ID NO:34) respectively; and wherein said anti-CXCR4 antibody fragment specifically binds to a CXCR4-expressing cell and wherein said human protamine protein binds to an siRNA molecule.

* * * * *

UNITED STATES PATENT AND TRADEMARK OFFICE
CERTIFICATE OF CORRECTION

PATENT NO. : 8,329,178 B2
APPLICATION NO. : 11/883258
DATED : December 11, 2012
INVENTOR(S) : Marasco et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1052 days.

Signed and Sealed this
Fifth Day of November, 2013

Teresa Stanek Rea
*Deputy Director of the United States Patent and Trademark Office*

SEQUENCE LISTING

<160> NUMBER OF SEQ ID NOS: 74

<210> SEQ ID NO 1
<211> LENGTH: 112
<212> TYPE: PRT
<213> ORGANISM: Homo sapiens

<400> SEQUENCE: 1

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Lys Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Gly Asp Val Trp Gly Gln Gly Thr Thr Val Thr Val Ser Ser
            100                 105                 110

<210> SEQ ID NO 2
<211> LENGTH: 121
<212> TYPE: PRT
<213> ORGANISM: Homo sapiens

<400> SEQUENCE: 2

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Val Ser Ser Leu Arg Ala Glu Asp Thr Ala Val Tyr Tyr Cys
                85                  90                  95

Val Arg Asp Leu Val Ala Ala Gly Thr Ala Phe Asp Ile Trp Gly
            100                 105                 110

Gln Gly Thr Thr Val Thr Val Ser Ser
        115                 120

<210> SEQ ID NO 3
<211> LENGTH: 120
<212> TYPE: PRT
<213> ORGANISM: Homo sapiens

<400> SEQUENCE: 3

Gln Val Gln Leu Gln Ser Gly Pro Gly Leu Val Lys Pro Ser Gln
1               5                   10                  15

Thr Leu Ser Leu Thr Cys Ala Val Ser Gly Asp Ser Val Ser Ser Asn
            20                  25                  30

Phe Val Ala Trp Asn Trp Ile Arg Gln Ser Pro Ser Arg Gly Leu Glu

```
                35                  40                  45
Trp Leu Gly Arg Thr Tyr Tyr Arg Ser Arg Trp Tyr Asn Asp Tyr Ala
 50                  55                  60

Val Ser Val Gln Ser Arg Ile Arg Val Thr Pro Asp Thr Ser Lys Asn
 65                  70                  75                  80

Gln Phe Ser Leu His Leu Asp Ser Val Thr Pro Glu Asp Thr Ala Val
                 85                  90                  95

Tyr Tyr Cys Ala Arg Gly Gln His Ser Gly Phe Asp Phe Trp Gly Gln
            100                 105                 110

Gly Thr Leu Val Thr Val Ser Ser
            115                 120

<210> SEQ ID NO 4
<211> LENGTH: 126
<212> TYPE: PRT
<213> ORGANISM: Homo sapiens

<400> SEQUENCE: 4

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
             35                  40                  45

Gly Trp Ile Ser Ala Tyr Asn Gly Asn Thr Asn Tyr Ala Gln Lys Leu
 50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Asp Thr Pro Gly Ile Ala Ala Arg Tyr Tyr Tyr Tyr Tyr Gly
            100                 105                 110

Met Asp Val Trp Gly Gln Gly Thr Thr Val Thr Val Ser Ser
            115                 120                 125

<210> SEQ ID NO 5
<211> LENGTH: 121
<212> TYPE: PRT
<213> ORGANISM: Homo sapiens

<400> SEQUENCE: 5

Gln Val Gln Leu Val Gln Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Pro Met His Trp Val Arg Gln Ala Pro Gly Lys Gly Leu Glu Trp Met
             35                  40                  45

Thr Val Ile Ser Ser Asp Gly Arg Asn Lys Tyr Tyr Pro Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Val Tyr Tyr Cys
                 85                  90                  95

Ala Arg Gly Gly Tyr His Asp Phe Trp Ser Gly Pro Asp Tyr Trp Gly
            100                 105                 110

Gln Gly Thr Leu Val Thr Val Ser Ser
            115                 120
```

<210> SEQ ID NO 6
<211> LENGTH: 127
<212> TYPE: PRT
<213> ORGANISM: Homo sapiens

<400> SEQUENCE: 6

Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Val Ser Gly Ile Thr Ile Phe Gly Gly Lys Trp Arg
            100                 105                 110

Ser Pro Asp Val Trp Gly Gln Gly Thr Thr Val Thr Val Ser Ser
        115                 120                 125

<210> SEQ ID NO 7
<211> LENGTH: 126
<212> TYPE: PRT
<213> ORGANISM: Homo sapiens

<400> SEQUENCE: 7

Gln Val Thr Leu Lys Glu Ser Gly Gly Gly Val Val Gln Pro Gly Arg
1               5                   10                  15

Ser Leu Arg Leu Ser Cys Ala Ala Ser Gly Phe Thr Phe Thr Asn Tyr
            20                  25                  30

Gly Leu His Trp Val Arg Gln Ala Pro Gly Lys Gly Leu Glu Trp Val
        35                  40                  45

Ala Val Ile Ser His Asp Gly Thr Lys Lys Tyr Tyr Ala Asp Ser Val
    50                  55                  60

Lys Gly Arg Phe Thr Ile Ser Arg Asp Ser Glu Asn Thr Leu Tyr
65                  70                  75                  80

Leu Gln Met Asn Ser Leu Arg Pro Glu Asp Ser Ala Leu Tyr Tyr Cys
                85                  90                  95

Ala Arg Asp Gly Gly Tyr Cys Ser Gly Gly Arg Cys Tyr Ser Tyr Gly
            100                 105                 110

Met Asp Val Trp Gly Gln Gly Thr Thr Val Thr Val Ser Ser
        115                 120                 125

<210> SEQ ID NO 8
<211> LENGTH: 122
<212> TYPE: PRT
<213> ORGANISM: Homo sapiens

<400> SEQUENCE: 8

Gln Val Gln Leu Val Gln Ser Gly Gly Gly Val Val Leu Pro Gly Arg
1               5                   10                  15

Ser Leu Arg Leu Ser Cys Val Ala Ser Gly Phe Thr Phe Arg Arg Tyr
            20                  25                  30

Gly Met His Trp Val Arg Gln Ala Pro Gly Lys Gly Leu Glu Trp Val

-continued

```
                35                  40                  45
Ser Leu Ile Ser Tyr Asp Gly Ser Lys Thr Phe Tyr Gly Glu Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ala Thr Val Thr Thr Asp Gly Tyr Tyr Tyr Met Asp Val Trp
            100                 105                 110

Gly Lys Gly Thr Thr Val Thr Val Ser Ser
            115                 120

<210> SEQ ID NO 9
<211> LENGTH: 89
<212> TYPE: PRT
<213> ORGANISM: Homo sapiens

<400> SEQUENCE: 9

Gln Ser Val Leu Thr Gln Pro Pro Ser Val Ser Pro Gly Gln Thr Val
 1               5                  10                  15

Thr Ile Ser Cys Gly Ser Val Ser Trp Tyr Gln Gln Pro Gly Ala
             20                  25                  30

Pro Lys Leu Leu Ile Tyr Asn Arg Pro Ser Gly Ile Pro Asp Arg Phe
             35                  40                  45

Ser Gly Ser Lys Ser Gly Asn Thr Ala Ser Leu Thr Ile Thr Gly Leu
 50                  55                  60

Gln Ala Glu Asp Ala Glu Tyr Tyr Cys Ser Trp Asp Val Phe Gly
 65                  70                  75                  80

Gly Gly Thr Lys Leu Thr Val Leu Gly
                 85

<210> SEQ ID NO 10
<211> LENGTH: 111
<212> TYPE: PRT
<213> ORGANISM: Homo sapiens

<400> SEQUENCE: 10

Gln Pro Val Leu Thr Gln Pro Arg Ser Val Ser Gly Ser Pro Gly Gln
 1               5                  10                  15

Ser Val Thr Ile Ser Cys Thr Gly Thr Ile Ser Asp Val Gly Gly His
             20                  25                  30

Asn Phe Val Ser Trp Tyr Gln Gln Asn Pro Gly Lys Ala Pro Lys Leu
             35                  40                  45

Ile Ile Phe Glu Val Thr Lys Arg Pro Ala Gly Val Pro Asp Arg Phe
 50                  55                  60

Ser Gly Ser Lys Ser Gly Asn Thr Ala Ser Leu Thr Val Ser Gly Leu
 65                  70                  75                  80

Gln Ala Glu Asp Glu Gly Tyr Tyr Cys Ser Ser Tyr Gly Gly Ser
                 85                  90                  95

Asn Asp Val Ile Phe Gly Gly Gly Thr Lys Leu Ser Val Leu Gly
            100                 105                 110

<210> SEQ ID NO 11
<211> LENGTH: 111
<212> TYPE: PRT
<213> ORGANISM: Homo sapiens

<400> SEQUENCE: 11
```

-continued

Gln Ser Val Leu Thr Gln Pro Pro Ser Val Ser Lys Gly Leu Arg Gln
1               5                   10                  15

Thr Ala Thr Leu Thr Cys Thr Gly Asn Ser Asn Val Gly Asn Gln
            20                  25                  30

Gly Ala Ala Trp Leu Gln Gln His Gln Gly His Pro Pro Lys Leu Leu
        35                  40                  45

Ser Tyr Arg Asn Asn Asn Arg Pro Ser Gly Ile Ser Glu Arg Phe Ser
    50                  55                  60

Ala Ser Arg Ser Gly Asn Thr Ala Ser Leu Thr Ile Thr Gly Leu Gln
65                  70                  75                  80

Pro Glu Asp Glu Ala Asp Tyr Tyr Cys Ser Ala Trp Asp Asn Arg Leu
                85                  90                  95

Lys Thr Tyr Val Phe Gly Thr Gly Gly Lys Val Thr Val Leu Gly
            100                 105                 110

<210> SEQ ID NO 12
<211> LENGTH: 109
<212> TYPE: PRT
<213> ORGANISM: Homo sapiens

<400> SEQUENCE: 12

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Lys Phe Phe Ala
            20                  25                  30

Ser Trp Tyr Gln Gln Lys Pro Gly Gln Ala Pro Val Leu Val Ile Tyr
        35                  40                  45

Gly Lys Asn Ser Arg Pro Ser Gly Ile Pro Asp Arg Phe Ser Gly Ser
    50                  55                  60

Asn Ser Arg Asn Thr Ala Ser Leu Thr Ile Thr Gly Ala Gln Ala Glu
65                  70                  75                  80

Asp Glu Gly Asp Tyr Tyr Cys Asn Ser Arg Asp Ser Arg Asp Asn His
                85                  90                  95

Gln Val Phe Gly Ala Gly Thr Lys Val Thr Val Leu Ser
            100                 105

<210> SEQ ID NO 13
<211> LENGTH: 108
<212> TYPE: PRT
<213> ORGANISM: Homo sapiens

<400> SEQUENCE: 13

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Asn Thr Asn
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln His Tyr Gly Ser Ser Pro Leu
                85                  90                  95

Thr Phe Gly Gly Gly Thr Lys Leu Glu Ile Lys Arg
            100                 105

```
<210> SEQ ID NO 14
<211> LENGTH: 107
<212> TYPE: PRT
<213> ORGANISM: Homo sapiens

<400> SEQUENCE: 14

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Lys Ser His Asn Thr Ala Tyr Leu Thr Ile Thr Gly Ala Gln Ala Glu
65                  70                  75                  80

Asp Glu Ala Asp Tyr Phe Cys Asn Ser Arg Ser Gly Ser Gln Arg Val
                85                  90                  95

Phe Gly Gly Gly Thr Lys Leu Thr Val Leu Gly
            100                 105

<210> SEQ ID NO 15
<211> LENGTH: 111
<212> TYPE: PRT
<213> ORGANISM: Homo sapiens

<400> SEQUENCE: 15

Gln Ser Val Leu Thr Gln Pro Pro Ser Ala Ser Gly Thr Pro Gly Gln
1               5                   10                  15

Arg Val Thr Ile Ser Cys Ser Gly Ser Arg Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Thr Asn Asn Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Leu Ser Phe Asp Ser Ser Leu
                85                  90                  95

Thr Ser Tyr Val Phe Gly Thr Gly Thr Lys Val Thr Val Leu Gly
            100                 105                 110

<210> SEQ ID NO 16
<211> LENGTH: 112
<212> TYPE: PRT
<213> ORGANISM: Homo sapiens

<400> SEQUENCE: 16

Gln Ser Val Leu Thr Gln Pro Pro Ser Ala Ser Gly Thr Pro Gly Gln
1               5                   10                  15

Arg Val Thr Ile Ser Cys Ser Gly Ser Arg Ser Asn Ile Gly Gly Asn
            20                  25                  30

Thr Val Asn Trp Tyr Gln Gln Leu Pro Gly Thr Ala Pro Lys Leu Leu
        35                  40                  45

Ile Tyr Ala Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80
```

Ser Glu Asp Glu Ala Asp Tyr Tyr Cys Ala Ala Trp Asp Asp Asn Leu
                85                  90                  95

Ser Gly His Val Val Phe Gly Gly Gly Thr Lys Leu Thr Val Leu Arg
            100                 105                 110

<210> SEQ ID NO 17
<211> LENGTH: 5
<212> TYPE: PRT
<213> ORGANISM: Homo sapiens

<400> SEQUENCE: 17

Ser Tyr Gly Met His
1               5

<210> SEQ ID NO 18
<211> LENGTH: 17
<212> TYPE: PRT
<213> ORGANISM: Homo sapiens

<400> SEQUENCE: 18

Val Ile Ser Tyr Asp Gly Ser Asn Lys Tyr Tyr Ala Asp Ser Val Lys
1               5                   10                  15
Gly

<210> SEQ ID NO 19
<211> LENGTH: 12
<212> TYPE: PRT
<213> ORGANISM: Homo sapiens

<400> SEQUENCE: 19

Asp Leu Val Ala Ala Ala Gly Thr Ala Phe Asp Ile
1               5                   10

<210> SEQ ID NO 20
<211> LENGTH: 14
<212> TYPE: PRT
<213> ORGANISM: Homo sapiens

<400> SEQUENCE: 20

Thr Gly Thr Ile Ser Asp Val Gly Gly His Asn Phe Val Ser
1               5                   10

<210> SEQ ID NO 21
<211> LENGTH: 7
<212> TYPE: PRT
<213> ORGANISM: Homo sapiens

<400> SEQUENCE: 21

Glu Val Thr Lys Arg Pro Ala
1               5

<210> SEQ ID NO 22
<211> LENGTH: 10
<212> TYPE: PRT
<213> ORGANISM: Homo sapiens

<400> SEQUENCE: 22

Ser Ser Tyr Gly Gly Ser Asn Asp Val Ile
1               5                   10

<210> SEQ ID NO 23
<211> LENGTH: 7
<212> TYPE: PRT
<213> ORGANISM: Homo sapiens

```
<400> SEQUENCE: 23

Ser Asn Phe Val Ala Trp Asn
1               5

<210> SEQ ID NO 24
<211> LENGTH: 18
<212> TYPE: PRT
<213> ORGANISM: Homo sapiens

<400> SEQUENCE: 24

Arg Thr Tyr Tyr Arg Ser Arg Trp Tyr Asn Asp Tyr Ala Val Ser Val
1               5                   10                  15

Gln Ser

<210> SEQ ID NO 25
<211> LENGTH: 8
<212> TYPE: PRT
<213> ORGANISM: Homo sapiens

<400> SEQUENCE: 25

Gly Gln His Ser Gly Phe Asp Phe
1               5

<210> SEQ ID NO 26
<211> LENGTH: 13
<212> TYPE: PRT
<213> ORGANISM: Homo sapiens

<400> SEQUENCE: 26

Thr Gly Asn Ser Asn Asn Val Gly Asn Gln Gly Ala Ala
1               5                   10

<210> SEQ ID NO 27
<211> LENGTH: 7
<212> TYPE: PRT
<213> ORGANISM: Homo sapiens

<400> SEQUENCE: 27

Arg Asn Asn Asn Arg Pro Ser
1               5

<210> SEQ ID NO 28
<211> LENGTH: 11
<212> TYPE: PRT
<213> ORGANISM: Homo sapiens

<400> SEQUENCE: 28

Ser Ala Trp Asp Asn Arg Leu Lys Thr Tyr Val
1               5                   10

<210> SEQ ID NO 29
<211> LENGTH: 5
<212> TYPE: PRT
<213> ORGANISM: Homo sapiens

<400> SEQUENCE: 29

Ser Tyr Gly Ile Ser
1               5

<210> SEQ ID NO 30
<211> LENGTH: 17
<212> TYPE: PRT
<213> ORGANISM: Homo sapiens

<400> SEQUENCE: 30
```

Trp Ile Ser Ala Tyr Asn Gly Asn Thr Asn Tyr Ala Gln Lys Leu Gln
1               5                   10                  15

Gly

<210> SEQ ID NO 31
<211> LENGTH: 17
<212> TYPE: PRT
<213> ORGANISM: Homo sapiens

<400> SEQUENCE: 31

Asp Thr Pro Gly Ile Ala Ala Arg Arg Tyr Tyr Tyr Tyr Gly Met Asp
1               5                   10                  15

Val

<210> SEQ ID NO 32
<211> LENGTH: 11
<212> TYPE: PRT
<213> ORGANISM: Homo sapiens

<400> SEQUENCE: 32

Gln Gly Asp Ser Leu Arg Lys Phe Phe Ala Ser
1               5                   10

<210> SEQ ID NO 33
<211> LENGTH: 7
<212> TYPE: PRT
<213> ORGANISM: Homo sapiens

<400> SEQUENCE: 33

Gly Lys Asn Ser Arg Pro Ser
1               5

<210> SEQ ID NO 34
<211> LENGTH: 11
<212> TYPE: PRT
<213> ORGANISM: Homo sapiens

<400> SEQUENCE: 34

Asn Ser Arg Asp Ser Arg Asp Asn His Gln Val
1               5                   10

<210> SEQ ID NO 35
<211> LENGTH: 5
<212> TYPE: PRT
<213> ORGANISM: Homo sapiens

<400> SEQUENCE: 35

Ser Tyr Pro Met His
1               5

<210> SEQ ID NO 36
<211> LENGTH: 17
<212> TYPE: PRT
<213> ORGANISM: Homo sapiens

<400> SEQUENCE: 36

Val Ile Ser Ser Asp Gly Arg Asn Lys Tyr Tyr Pro Asp Ser Val Lys
1               5                   10                  15

Gly

<210> SEQ ID NO 37
<211> LENGTH: 12
<212> TYPE: PRT

<213> ORGANISM: Homo sapiens

<400> SEQUENCE: 37

Gly Gly Tyr His Asp Phe Trp Ser Gly Pro Asp Tyr
1               5                   10

<210> SEQ ID NO 38
<211> LENGTH: 11
<212> TYPE: PRT
<213> ORGANISM: Homo sapiens

<400> SEQUENCE: 38

Arg Ala Ser Gln Ser Val Asn Thr Asn Leu Ala
1               5                   10

<210> SEQ ID NO 39
<211> LENGTH: 7
<212> TYPE: PRT
<213> ORGANISM: Homo sapiens

<400> SEQUENCE: 39

Gly Ala Ser Ser Arg Ala Thr
1               5

<210> SEQ ID NO 40
<211> LENGTH: 9
<212> TYPE: PRT
<213> ORGANISM: Homo sapiens

<400> SEQUENCE: 40

Gln His Tyr Gly Ser Ser Pro Leu Thr
1               5

<210> SEQ ID NO 41
<211> LENGTH: 5
<212> TYPE: PRT
<213> ORGANISM: Homo sapiens

<400> SEQUENCE: 41

Ser Tyr Ala Met Ser
1               5

<210> SEQ ID NO 42
<211> LENGTH: 17
<212> TYPE: PRT
<213> ORGANISM: Homo sapiens

<400> SEQUENCE: 42

Asn Ile Lys Gln Asp Gly Ser Glu Lys Tyr Tyr Val Asp Ser Val Lys
1               5                   10                  15

Gly

<210> SEQ ID NO 43
<211> LENGTH: 18
<212> TYPE: PRT
<213> ORGANISM: Homo sapiens

<400> SEQUENCE: 43

Asp Gln Val Ser Gly Ile Thr Ile Phe Gly Gly Lys Trp Arg Ser Pro
1               5                   10                  15

Asp Val

<210> SEQ ID NO 44
<211> LENGTH: 11

```
<212> TYPE: PRT
<213> ORGANISM: Homo sapiens

<400> SEQUENCE: 44

Gln Gly Asp Ser Leu Arg Ser Tyr Tyr Ala Ser
1               5                   10

<210> SEQ ID NO 45
<211> LENGTH: 7
<212> TYPE: PRT
<213> ORGANISM: Homo sapiens

<400> SEQUENCE: 45

Gly Lys Asn Asn Arg Pro Ser
1               5

<210> SEQ ID NO 46
<211> LENGTH: 9
<212> TYPE: PRT
<213> ORGANISM: Homo sapiens

<400> SEQUENCE: 46

Asn Ser Arg Ser Gly Ser Gln Arg Val
1               5

<210> SEQ ID NO 47
<211> LENGTH: 5
<212> TYPE: PRT
<213> ORGANISM: Homo sapiens

<400> SEQUENCE: 47

Asn Tyr Gly Leu His
1               5

<210> SEQ ID NO 48
<211> LENGTH: 17
<212> TYPE: PRT
<213> ORGANISM: Homo sapiens

<400> SEQUENCE: 48

Val Ile Ser His Asp Gly Thr Lys Lys Tyr Tyr Ala Asp Ser Val Lys
1               5                   10                  15

Gly

<210> SEQ ID NO 49
<211> LENGTH: 17
<212> TYPE: PRT
<213> ORGANISM: Homo sapiens

<400> SEQUENCE: 49

Asp Gly Gly Tyr Cys Ser Gly Arg Cys Tyr Ser Tyr Gly Met Asp
1               5                   10                  15

Val

<210> SEQ ID NO 50
<211> LENGTH: 13
<212> TYPE: PRT
<213> ORGANISM: Homo sapiens

<400> SEQUENCE: 50

Ser Gly Ser Arg Ser Asn Ile Gly Ser Asn Thr Val Asn
1               5                   10

<210> SEQ ID NO 51
```

```
<211> LENGTH: 7
<212> TYPE: PRT
<213> ORGANISM: Homo sapiens

<400> SEQUENCE: 51

Thr Asn Asn Gln Arg Pro Ser
1               5

<210> SEQ ID NO 52
<211> LENGTH: 11
<212> TYPE: PRT
<213> ORGANISM: Homo sapiens

<400> SEQUENCE: 52

Leu Ser Phe Asp Ser Ser Leu Thr Ser Tyr Val
1               5                   10

<210> SEQ ID NO 53
<211> LENGTH: 5
<212> TYPE: PRT
<213> ORGANISM: Homo sapiens

<400> SEQUENCE: 53

Arg Tyr Gly Met His
1               5

<210> SEQ ID NO 54
<211> LENGTH: 17
<212> TYPE: PRT
<213> ORGANISM: Homo sapiens

<400> SEQUENCE: 54

Leu Ile Ser Tyr Asp Gly Ser Lys Thr Phe Tyr Gly Glu Ser Val Lys
1               5                   10                  15

Gly

<210> SEQ ID NO 55
<211> LENGTH: 13
<212> TYPE: PRT
<213> ORGANISM: Homo sapiens

<400> SEQUENCE: 55

Ala Thr Val Thr Thr Asp Gly Tyr Tyr Tyr Met Asp Val
1               5                   10

<210> SEQ ID NO 56
<211> LENGTH: 13
<212> TYPE: PRT
<213> ORGANISM: Homo sapiens

<400> SEQUENCE: 56

Ser Gly Ser Arg Ser Asn Ile Gly Gly Asn Thr Val Asn
1               5                   10

<210> SEQ ID NO 57
<211> LENGTH: 7
<212> TYPE: PRT
<213> ORGANISM: Homo sapiens

<400> SEQUENCE: 57

Ala Asn Asn Gln Arg Pro Ser
1               5

<210> SEQ ID NO 58
<211> LENGTH: 12
```

```
<212> TYPE: PRT
<213> ORGANISM: Homo sapiens

<400> SEQUENCE: 58

Ala Ala Trp Asp Asp Asn Leu Ser Gly His Val Val
1               5                   10

<210> SEQ ID NO 59
<211> LENGTH: 3
<212> TYPE: PRT
<213> ORGANISM: Homo sapiens

<400> SEQUENCE: 59

Glu Leu Arg
1

<210> SEQ ID NO 60
<211> LENGTH: 38
<212> TYPE: PRT
<213> ORGANISM: Homo sapiens

<400> SEQUENCE: 60

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
            20                  25                  30

Asn Ala Asn Phe Asn Lys
            35

<210> SEQ ID NO 61
<211> LENGTH: 38
<212> TYPE: PRT
<213> ORGANISM: Macaca mulatta

<400> SEQUENCE: 61

Met Glu Gly Ile Ser Ile Tyr Thr Ser Asp Asn Tyr Thr Glu Glu Met
1               5                   10                  15

Gly Ser Gly Asp Tyr Asp Ser Ile Lys Glu Pro Cys Phe Arg Glu Glu
            20                  25                  30

Asn Ala Asn Phe Asn Arg
            35

<210> SEQ ID NO 62
<211> LENGTH: 38
<212> TYPE: PRT
<213> ORGANISM: Mus musculus

<400> SEQUENCE: 62

Met Glu Pro Ile Ser Ile Tyr Thr Ser Asp Asn Tyr Ser Glu Glu Val
1               5                   10                  15

Gly Ser Gly Asp Tyr Asp Ser Asn Lys Glu Pro Cys Phe Asp Glu Glu
            20                  25                  30

Asn Val His Phe Asn Arg
            35

<210> SEQ ID NO 63
<211> LENGTH: 14
<212> TYPE: PRT
<213> ORGANISM: Homo sapiens

<400> SEQUENCE: 63

Asp Ala Val Ala Asn Trp Tyr Phe Gly Asn Phe Leu Cys Lys
1               5                   10
```

```
<210> SEQ ID NO 64
<211> LENGTH: 14
<212> TYPE: PRT
<213> ORGANISM: Macaca mulatta

<400> SEQUENCE: 64

Asp Ala Val Ala Asn Trp Tyr Phe Gly Asn Phe Leu Cys Lys
1               5                   10

<210> SEQ ID NO 65
<211> LENGTH: 14
<212> TYPE: PRT
<213> ORGANISM: Mus musculus

<400> SEQUENCE: 65

Asp Ala Met Ala Asp Trp Tyr Phe Lys Asn Phe Leu Cys Lys
1               5                   10

<210> SEQ ID NO 66
<211> LENGTH: 27
<212> TYPE: PRT
<213> ORGANISM: Homo sapiens

<400> SEQUENCE: 66

Asn Val Ser Glu Ala Asp Asp Arg Tyr Ile Cys Asp Arg Phe Tyr Pro
1               5                   10                  15

Asn Asp Leu Trp Val Val Val Phe Gln Phe Gln
            20                  25

<210> SEQ ID NO 67
<211> LENGTH: 27
<212> TYPE: PRT
<213> ORGANISM: Macaca mulatta

<400> SEQUENCE: 67

Ser Val Ser Glu Ala Asp Asp Arg Tyr Ile Cys Asp Arg Phe Tyr Pro
1               5                   10                  15

Asn Asp Leu Trp Val Val Val Phe Gln Phe Gln
            20                  25

<210> SEQ ID NO 68
<211> LENGTH: 30
<212> TYPE: PRT
<213> ORGANISM: Mus musculus

<400> SEQUENCE: 68

Asp Val Ser Gln Gly Asp Ile Ala Gln Gly Arg Tyr Ile Cys Asp Arg
1               5                   10                  15

Leu Tyr Pro Asp Ser Leu Trp Met Val Val Phe Gln Phe Gln
            20                  25                  30

<210> SEQ ID NO 69
<211> LENGTH: 21
<212> TYPE: PRT
<213> ORGANISM: Homo sapiens

<400> SEQUENCE: 69

Asp Ser Phe Ile Leu Leu Glu Ile Ile Lys Gln Gly Cys Glu Phe Glu
1               5                   10                  15

Asn Thr Val His Lys
            20
```

```
<210> SEQ ID NO 70
<211> LENGTH: 21
<212> TYPE: PRT
<213> ORGANISM: Macaca mulatta

<400> SEQUENCE: 70

Asp Ser Phe Ile Leu Leu Glu Ile Ile Lys Gln Gly Cys Glu Phe Glu
1               5                   10                  15

Asn Thr Val His Lys
            20

<210> SEQ ID NO 71
<211> LENGTH: 21
<212> TYPE: PRT
<213> ORGANISM: Mus musculus

<400> SEQUENCE: 71

Asp Ser Phe Ile Leu Leu Gly Val Ile Lys Gln Gly Cys Asp Phe Glu
1               5                   10                  15

Ser Ile Val His Lys
            20

<210> SEQ ID NO 72
<211> LENGTH: 365
<212> TYPE: PRT
<213> ORGANISM: Homo sapiens

<400> SEQUENCE: 72

Met Glu Gly Ile Ser Ile Tyr Thr Ser Asp Asn Tyr Thr Glu Met
1               5                   10                  15

Gly Ser Gly Asp Tyr Asp Ser Met Lys Glu Pro Cys Phe Arg Glu Glu
                20                  25                  30

Asn Ala Asn Phe Asn Lys Ile Phe Leu Pro Thr Ile Tyr Ser Ile Ile
            35                  40                  45

Phe Leu Thr Gly Ile Val Gly Asn Gly Leu Val Ile Leu Val Met Gly
        50                  55                  60

Tyr Gln Lys Lys Leu Arg Ser Met Thr Asp Lys Tyr Arg Leu His Leu
65                  70                  75                  80

Ser Val Ala Asp Leu Leu Phe Val Ile Thr Leu Pro Phe Trp Ala Val
                85                  90                  95

Asp Ala Val Ala Asn Trp Tyr Phe Gly Asn Phe Leu Cys Lys Ala Val
                100                 105                 110

His Val Ile Tyr Thr Val Asn Leu Tyr Ser Ser Val Leu Ile Leu Ala
            115                 120                 125

Phe Ile Ser Leu Asp Arg Tyr Leu Ala Ile Val His Ala Thr Asn Ser
        130                 135                 140

Gln Arg Pro Arg Lys Leu Leu Ala Glu Lys Val Val Tyr Val Gly Val
145                 150                 155                 160

Trp Ile Pro Ala Leu Leu Leu Thr Ile Pro Asp Phe Ile Phe Ala Asn
                165                 170                 175

Val Ser Glu Ala Asp Asp Arg Tyr Ile Cys Asp Arg Phe Tyr Pro Asn
                180                 185                 190

Asp Leu Trp Val Val Val Phe Gln Phe Gln His Ile Met Val Gly Leu
            195                 200                 205

Ile Leu Pro Gly Ile Val Ile Leu Ser Cys Tyr Cys Ile Ile Ile Ser
        210                 215                 220

Lys Leu Ser His Ser Lys Gly His Gln Lys Arg Lys Ala Leu Lys Thr
225                 230                 235                 240
```

```
Thr Val Ile Leu Ile Leu Ala Phe Phe Ala Cys Trp Leu Pro Tyr Tyr
            245                 250                 255

Ile Gly Ile Ser Ile Asp Ser Phe Ile Leu Glu Ile Ile Lys Gln
        260                 265                 270

Gly Cys Glu Phe Glu Asn Thr Val His Lys Trp Ile Ser Ile Thr Glu
            275                 280                 285

Ala Leu Ala Phe Phe His Cys Cys Leu Asn Pro Ile Leu Tyr Ala Phe
            290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
                325                 330                 335

His Ser Ser Val Ser Thr Glu Ser Glu Ser Ser Ser Phe His Ser Ser
            340                 345                 350

Gly Thr Glu Thr Ser Gln Val Ala Pro Ala Leu Glu Ser
            355                 360                 365

<210> SEQ ID NO 73
<211> LENGTH: 341
<212> TYPE: PRT
<213> ORGANISM: Homo sapiens

<400> SEQUENCE: 73

Met Glu Pro Cys Phe Arg Glu Glu Asn Ala Asn Phe Asn Lys Ile Phe
1               5                   10                  15

Leu Pro Thr Ile Tyr Ser Ile Ile Phe Leu Thr Gly Ile Val Gly Asn
            20                  25                  30

Gly Leu Val Ile Leu Val Met Gly Tyr Gln Lys Lys Leu Arg Ser Met
        35                  40                  45

Thr Asp Lys Tyr Arg Leu His Leu Ser Val Ala Asp Leu Leu Phe Val
    50                  55                  60

Ile Thr Leu Pro Phe Trp Ala Val Asp Ala Val Ala Asn Trp Tyr Phe
65                  70                  75                  80

Gly Asn Phe Leu Cys Lys Ala Val His Val Ile Tyr Thr Val Asn Leu
                85                  90                  95

Tyr Ser Ser Val Leu Ile Leu Ala Phe Ile Ser Leu Asp Arg Tyr Leu
            100                 105                 110

Ala Ile Val His Ala Thr Asn Ser Gln Arg Pro Arg Lys Leu Leu Ala
        115                 120                 125

Glu Lys Val Val Tyr Val Gly Val Trp Ile Pro Ala Leu Leu Leu Thr
    130                 135                 140

Ile Pro Asp Phe Ile Phe Ala Asn Val Ser Glu Ala Asp Asp Arg Tyr
145                 150                 155                 160

Ile Cys Asp Arg Phe Tyr Pro Asn Asp Leu Trp Val Val Val Phe Gln
                165                 170                 175

Phe Gln His Ile Met Val Gly Leu Ile Leu Pro Gly Ile Val Ile Leu
            180                 185                 190

Ser Cys Tyr Cys Ile Ile Ile Ser Lys Leu Ser His Ser Lys Gly His
        195                 200                 205

Gln Lys Arg Lys Ala Leu Lys Thr Thr Val Ile Leu Ile Leu Ala Phe
    210                 215                 220

Phe Ala Cys Trp Leu Pro Tyr Tyr Ile Gly Ile Ser Ile Asp Ser Phe
225                 230                 235                 240

Ile Leu Leu Glu Ile Ile Lys Gln Gly Cys Glu Phe Glu Asn Thr Val
                245                 250                 255
```

```
His Lys Trp Ile Ser Ile Thr Glu Ala Leu Ala Phe Phe His Cys Cys
            260                 265                 270

Leu Asn Pro Ile Leu Tyr Ala Phe Leu Gly Ala Lys Phe Lys Thr Ser
            275                 280                 285

Ala Gln His Ala Leu Thr Ser Val Ser Arg Gly Ser Ser Leu Lys Ile
            290                 295                 300

Leu Ser Lys Gly Lys Arg Gly His Ser Ser Val Ser Thr Glu Ser
305                 310                 315                 320

Glu Ser Ser Ser Phe His Ser Ser Gly Thr Glu Thr Ser Gln Val Ala
                    325                 330                 335

Pro Ala Leu Glu Ser
            340

<210> SEQ ID NO 74
<211> LENGTH: 334
<212> TYPE: PRT
<213> ORGANISM: Homo sapiens

<400> SEQUENCE: 74

Glu Asn Ala Asn Phe Asn Lys Ile Phe Leu Pro Thr Ile Tyr Ser Ile
1               5                   10                  15

Ile Phe Leu Thr Gly Ile Val Gly Asn Gly Leu Val Ile Leu Val Met
            20                  25                  30

Gly Tyr Gln Lys Lys Leu Arg Ser Met Thr Asp Lys Tyr Arg Leu His
            35                  40                  45

Leu Ser Val Ala Asp Leu Leu Phe Val Ile Thr Leu Pro Phe Trp Ala
        50                  55                  60

Val Asp Ala Val Ala Asn Trp Tyr Phe Gly Asn Phe Leu Cys Lys Ala
65              70                  75                  80

Val His Val Ile Tyr Thr Val Asn Leu Tyr Ser Ser Val Leu Ile Leu
                85                  90                  95

Ala Phe Ile Ser Leu Asp Arg Tyr Leu Ala Ile Val His Ala Thr Asn
            100                 105                 110

Ser Gln Arg Pro Arg Lys Leu Leu Ala Glu Lys Val Val Tyr Val Gly
            115                 120                 125

Val Trp Ile Pro Ala Leu Leu Leu Thr Ile Pro Asp Phe Ile Phe Ala
        130                 135                 140

Asn Val Ser Glu Ala Asp Asp Arg Tyr Ile Cys Asp Arg Phe Tyr Pro
145             150                 155                 160

Asn Asp Leu Trp Val Val Phe Gln Phe Gln His Ile Met Val Gly
                165                 170                 175

Leu Ile Leu Pro Gly Ile Val Ile Leu Ser Cys Tyr Cys Ile Ile Ile
            180                 185                 190

Ser Lys Leu Ser His Ser Lys Gly His Gln Lys Arg Lys Ala Leu Lys
            195                 200                 205

Thr Thr Val Ile Leu Ile Leu Ala Phe Phe Ala Cys Trp Leu Pro Tyr
        210                 215                 220

Tyr Ile Gly Ile Ser Ile Asp Ser Phe Ile Leu Leu Glu Ile Ile Lys
225             230                 235                 240

Gln Gly Cys Glu Phe Glu Asn Thr Val His Lys Trp Ile Ser Ile Thr
                245                 250                 255

Glu Ala Leu Ala Phe Phe His Cys Cys Leu Asn Pro Ile Leu Tyr Ala
            260                 265                 270

Phe Leu Gly Ala Lys Phe Lys Thr Ser Ala Gln His Ala Leu Thr Ser
            275                 280                 285
```

-continued

```
Val Ser Arg Gly Ser Ser Leu Lys Ile Leu Ser Lys Gly Lys Arg Gly
    290             295             300

Gly His Ser Ser Val Ser Thr Glu Ser Glu Ser Ser Ser Phe His Ser
305             310             315             320

Ser Gly Thr Glu Thr Ser Gln Val Ala Pro Ala Leu Glu Ser
        325             330
```